US007846906B2

(12) United States Patent
Dobie et al.

(10) Patent No.: US 7,846,906 B2
(45) Date of Patent: *Dec. 7, 2010

(54) MODULATION OF GROWTH HORMONE RECEPTOR EXPRESSION AND INSULIN-LIKE GROWTH FACTOR EXPRESSION

(75) Inventors: Kenneth Dobie, Carlsbad, CA (US); Ravi Jain, Carlsbad, CA (US)

(73) Assignees: Isis Pharmaceuticals, Inc., Carlsbad, CA (US); Antisense Therapeutics Limited, Toorak, Victoria (AU)

( * ) Notice: Subject to any disclaimer, the term of this patent is extended or adjusted under 35 U.S.C. 154(b) by 58 days.

This patent is subject to a terminal disclaimer.

(21) Appl. No.: 10/547,239

(22) PCT Filed: Feb. 27, 2004

(86) PCT No.: PCT/US2004/005896

§ 371 (c)(1),
(2), (4) Date: Aug. 25, 2005

(87) PCT Pub. No.: WO2004/078922

PCT Pub. Date: Sep. 16, 2004

(65) Prior Publication Data

US 2006/0178325 A1    Aug. 10, 2006

Related U.S. Application Data

(60) Provisional application No. 60/451,455, filed on Feb. 28, 2003, provisional application No. 60/490,230, filed on Jul. 25, 2003.

(51) Int. Cl.
*A61K 31/70* (2006.01)
*A01N 43/04* (2006.01)
*C07H 21/02* (2006.01)
*C07H 21/04* (2006.01)

(52) U.S. Cl. ........................ 514/44; 536/23.1; 536/24.3; 536/24.31; 536/24.33

(58) Field of Classification Search ........................ None
See application file for complete search history.

(56) References Cited

U.S. PATENT DOCUMENTS

| 5,057,417 | A  | * | 10/1991 | Hammonds et al. ......... 435/69.1 |
| 5,801,154 | A  |   | 9/1998  | Baracchini et al. |
| 5,861,244 | A  |   | 1/1999  | Wang et al. |
| 5,968,748 | A  | * | 10/1999 | Bennett et al. .................. 435/6 |
| 6,172,216 | B1 | * | 1/2001  | Bennett et al. .............. 536/24.5 |
| 6,228,642 | B1 | * | 5/2001  | Baker et al. ................. 435/375 |
| 6,582,908 | B2 |   | 6/2003  | Fodor et al. |
| 6,670,461 | B1 | * | 12/2003 | Wengel et al. .............. 536/23.1 |
| 2001/0053519 | A1 |   | 12/2001 | Fodor et al. |
| 2003/0228597 | A1 |   | 12/2003 | Cowsert et al. |
| 2003/0232438 | A1 | * | 12/2003 | Dobie et al. ................. 435/375 |
| 2004/0241651 | A1 |   | 12/2004 | Olek et al. |

FOREIGN PATENT DOCUMENTS

| WO | WO 9726270  |   | 7/1997  |
| WO | WO 9965928  |   | 12/1999 |
| WO | WO 0116312  |   | 3/2001  |
| WO | WO 0177384  |   | 10/2001 |
| WO | WO 0210449  |   | 2/2002  |
| WO | WO0210449   | * | 2/2002  |
| WO | WO 0226796  |   | 4/2002  |

OTHER PUBLICATIONS

Branch, 1998, TIBS, pp. 45-50.*
Florini et al. Endocrine Review, vol. 17, No. 5, pp. 481-517.*
Jen et al. 2000, Stem Cells, vol. 18, pp. 307-319.*
Opalinska et al. 2002, Nature Reviews: Drug Discovery, vol. 1, p. 503-514.*
Chirila et al. 2002, Biomaterials, vol. 23, pp. 321-342.*
Schiavone et al. 2004, Current Pharmaceutical Design, vol. 10, pp. 769-784.*
Pellegrini et al. (J. Neurosci. 1996, 16, 8140-8148; see IDS).*
GenBank Accession No. NM_000163.1, Nov. 5, 2002.*
Hammond, et al., Feb. 2000, *Natural*, vol. 2, pp. 110-119.
Elbashir, May 2001, *Nature*, vol. 411, pp. 494-498.
Clemmons, D. R., "IGF Binding Proteins: Regulation of Cellular Actions," *Growth Regulation* (1992) 2:80-87.
Rechler, M. M. et al., "Insulin-like Growth Factor Binding Proteins: Gene Structure and Expression," *Growth Regulation* (1992) 2:55-68.
Beaudry, A. et al., In Vitro Selection of a Novel Nuclease-Resistant RNA Phosphodiesterase, Chemistry & Biology, May 2000, pp. 323-334, vol. 7.
Chen, N.-Y. et al., A Growth Hormone Antagonist Protects Mice Against Streptozotocin Induced Glomerulosclerosis Even in the Presence of Elevated Levels of Glucose and Glycated Hemoglobin, Endocrinology, Aug. 5, 1996, pp. 5163-5165, vol. 137.
Coschigano, K. et al., Assessment of Growth Parameters and Life Span of GHR/BP Gene-Disrupted Mice, Endocrinology, Feb. 14, 2000, pp. 2608-2613, vol. 141.
Flyvbjerg, A. et al., Inhibitory Effect of a Growth Hormone Receptor Antagonist (G120K-PEG) on Renal Enlargement, Glomerular Hypertrophy, and Urinary Albumin Excretion in Experimental Diabetes in Mice, Diabetes, 1999, pp. 377-382, vol. 48.
Francisco, et al., A Class of Highly Polymorphic Tetranucleotide Repeats for Canine Genetic Mapping, Mamm. Genome, GenBank Accession No. L78573.1, Nov. 29, 1996.

(Continued)

*Primary Examiner*—Janet Epps-Smith
(74) *Attorney, Agent, or Firm*—Isis Pharmaceuticals, Inc. Patent Dept.

(57) ABSTRACT

Compounds, compositions and methods are provided for modulating the expression of growth hormone receptor and/or insulin like growth factor-I (IGF-I). The compositions comprise oligonucleotides, targeted to nucleic acid encoding growth hormone receptor. Methods of using these compounds for modulation of growth hormone receptor expression and for diagnosis and treatment of disease associated with expression of growth hormone receptor and/or insulin-like growth factor-I are provided. Diagnostic methods and kits are also provided.

35 Claims, No Drawings

OTHER PUBLICATIONS

Friend, K et al., The Growth Hormone Receptor Antagonist Pegvisomant Exhibits Antitumor Activity in Multiple Preclinical Tumor Models, Proceedings of the 200 NCI-EORTC-AACR Symposium, Nov. 2000,.vol. 6 Supplement.

Friend, K., Cancer and the Potential Place for Growth Hormone Receptor Antagonist Therapy, Growth Hormone & IGF Research 2001, pp. S121-S123, Supplement A.

Grant, M., The Efficacy of Octreotide in the Therapy of Severe Nonproliferative and Early Proliferative Diabetic Retinopathy, Diabetes Care, Apr. 2000, pp. 504-509, vol. 23.

GronbæK, H. et al., Inhibitory Effects of Octreotide on Renal and Glomerular Growth in Early Experimental Diabetes in Mice, Journal of Endocrinology, 2002, pp. 637-643, vol. 172.

Higgins, R. et al., Somatostatin Analogs Inhibit Neonatal Retinal Neovascularization, Exp. Eye Res, 2002, pp. 553-559, vol. 74.

Karpeisky A., et al., Highly Efficient Synthesis of 2-0-Amino Nucleotides and their Incorporation in Hammerhead Ribozymes, Tetrahedron Letters, Mar. 5, 1998, pp. 1131-1134, vol. 39.

Landau, D. et al., A Novel Somatostatin Analogue Prevents Early Renal Complications in the Nonobese Diabetic Mouse, Kidney International, 2001, pp. 505-512, vol. 60.

LeRoith, D. et al., Molecular and Cellular Aspects of the Insulin-Like Growth Factor I Receptor, Endocrine Reviews, 1995, pp. 143-163, vol. 16.

Mertani H C et al., "In situ gene expression of growth hormone (GH) receptor and GH binding protein in adult male rat tissues", Molecular and Cellular Endocrinology, 1995, pp. 47-61.

Paran, D. et al., A Pilot Study of a Long Acting Somatostatin Analogue for the Treatment of Refractory Rheumatoid Arthritis, Ann. Rheum. Dis., 2001, pp. 888-891, vol. 60.

Paran D. et al., Probable Adverse Effects of Long Term Use of Somatostatin Analogues in Patients with RA, Ann Rheum Dis., 2001, pp. 1117, vol. 61.

Pellegrini, E. et al., Central Administration of a Growth Hormone (GH) Receptor mRNA Antisense Increases GH Pulsatility and Decreases Hypothalamic Somatostatin Expression in Rats, Journal of Neuroscience, Dec. 15, 1996, pp. 8140-8148, vol. 16.

Rubin, R. et al., Biology of Disease-Insuling-Like Growth Factor-I Receptor: Its Role in Cell Proliferation, Apoptosis, and Tumorigenicity, Laboratory Investigation, 1995, pp. 311-331, vol. 73.

Segev, Y. et al., Growth Hormone Receptor Antagonism Prevents Early Renal Changes in Nonobese Diabetic Mice, J. Am., Soc. Nephrol., 1999, pp. 2374-2381, vol. 10.

Serri, O. et al., Somatostatin Analogue, Octreotide, Reduces Increased Glomerular Filtration Rate and Kidney Size in Insulin-Dependent Diabetes, JAMA, Feb. 20, 1991, pp. 888-892, vol. 265.

Sjögren, K. et al., Liver-Derived Insulin-Like Growth Factor I (IGF-I) is the Principal Source of IGF-I in Blood But is Not Required for Postnatal Body Growth in Mice, Proc. Natl. Acad. Sci. USA, Jun. 1999, pp. 7088-792, vol. 96.

Smith, L. et al., Essential Role of Growth Hormone in Ischemia-Induced Retinal Neovascularization, Science, Jun. 13, 1997, pp. 1706-1709, vol. 276.

Tachas G et al., "A GH receptor anit-sense oligonucleotide inhibits hepatic GH receptor expression, 1 GF-I production and body weight gain in normal mice," Journal of Endocrinology, Apr. 2006, pp. 147-154.

Trainer, P. et al., Treatment of Acromegaly with the Growth Hormone Receptor Antagonist Pegvisomant, The New England Journal of Medicine, Apr. 20, 2000, pp. 1171-1177, vol. 342.

Turnley, A. et al., Suppressor of Cytokine Signaling 2 Regulates Neuronal Differentiation by Inhibiting Growth Hormone Signaling, Nature Neuroscience, Nov. 2002, pp. 1155-1162, vol. 5.

Ullrich, A., et al., Insulin-like Growth Factor I Receptor Primary Structure: Comparision with Insulin Receptor Suggests Structural Determinants that Define Functional Specificity, EMBO J., Jul. 18, 1986, pp. 2503-2512, vol. 5.

Van Der Lely, A., et al., Long-Term Treatment of Acromegaly with Pegvisomant, A Growth Hormone Receptor Antagonist, The Lancet, Nov. 24, 2001, pp. 1754-1759, vol. 358.

Van Neck, J., et al., Dose-Response Effects of a New Growth Hormone Receptor Antagonist (B2036-PEG) on Circulating, Hepatic and Renal Expression of the Growth Hormone/Insulin-Like Growth Factor System in Adult Mice, Journal of Endocrinology, 2000, pp. 295-303, vol. 167.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

New England BioLabs. Inc. Catalogue (1998): 121,284.

Reynolds et al., Rational siRNA design for RNA interference, 2004, Nature Biotechnology, vol. 22, pp. 326-330.

Agrawal et al. Antisense therapeutics: it is as simple as complementary base recognition? Molecule Medicine Today. Feb. 2000, vol. 6, pp. 72-81.

Fuh et al. Rational Design of Potent Antagonists to the Human Growth hormone Receptor. SCIENCE, Jun. 1992, vol. 256, pp. 1677-1680.

Hammond et al. Post-Transcriptional Gene Silencing by Double-Stranded DNA. NATURE. Feb. 2001, vol. 2, pp. 110-119.

Yoshizato et al. GenBank Accession No. NM_000163.

Restriction Requirement from U.S. Appl. No. 10/789,526, dated Oct. 3, 2005.

Office Action from U.S. Appl. No. 10/789,526, dated Jun. 13, 2006.

Office Action from U.S. Appl. No. 10/789,526, dated Nov. 28, 2006.

Final Office Action from U.S. Appl. No. 10/789,526, dated Jun. 28, 2007.

Office Action from U.S. Appl. No. 10/789,526, dated Jan. 9, 2008.

Office Action from U.S. Appl. No. 10/789,526, dated Jul. 24, 2008.

Final Office Action from U.S. Appl. No. 10/789,526, dated Dec. 31, 2008.

Supplementary European Search Report from EP Application No. 04 71 5642, dated Jul. 12, 2007.

International Search Report from PCT/US04/05896, dated Sep. 20, 2006.

International Preliminary Report on Patentability from PCT/US04/005896, dated. Oct. 26, 2006.

Restriction Requirement from U.S. Appl. No. 10/927,466, dated Dec. 22, 2006.

Office Action from U.S. Appl. No. 10/927,466, dated Jun. 18, 2007.

Final Office Action from U.S. Appl. No. 10/927,466, dated Feb. 13, 2008.

Office Action from U.S. Appl. No. 10/927,466, dated Oct. 30, 2008.

Crooke et al., "Basic Principles of Antisense Therapeutics" Antisense Research and Application (1998) Chapter 1:1-50.

Sanghvi et al; "Heterocyclic Base Modifications in Nucleic Acids and Their Applications in Antisense Oligonucleotides" Antisense Research and Applications (1993) pp. 273-288.

* cited by examiner

MODULATION OF GROWTH HORMONE RECEPTOR EXPRESSION AND INSULIN-LIKE GROWTH FACTOR EXPRESSION

CROSS REFERENCE TO RELATED APPLICATIONS

This application is the National Stage of International Application No. PCT/US2004/005896 filed Feb. 27, 2004, which claims the benefit of U.S. patent application Ser. No. 10/789,526, filed Feb. 26, 2004, and claims the benefit of U.S. Provisional Application No. 60/451,455, filed Feb. 28, 2003, and U.S. Provisional Application No. 60/490,230, filed Jul. 25, 2003, the entire disclosures of which are hereby incorporated by reference in their entirety for all purposes.

FIELD OF THE INVENTION

The present invention provides compositions and methods for modulating the expression of growth hormone receptor. In particular, this invention relates to compounds, particularly oligonucleotide compounds, which, in preferred embodiments, hybridize with nucleic acid molecules encoding growth hormone receptor. Such compounds are shown herein to modulate the expression of growth hormone receptor and also to modulate the expression of insulin-like growth factor 1 (IGF-I) to animal and human equivalent therapeutic levels which are relevant to the treatment of diseases including acromegaly, gigantism, age-related macular degeneration, diabetic retinopathy, diabetic nephropathy, diabetes, and growth hormone and IGF-I dependent tumors. The growth hormone receptor modulating effects are also relevant to the treatment of arthritis and other conditions involving growth hormone receptor and/or growth hormone/insulin-like growth factor-I axis. Similarly, antisense compounds directed to any one or more of the targets in the growth hormone/insulin-like growth factor-I axis, including growth hormone, growth hormone receptor, IGF-I and IGF-I receptor, can be used in the treatment of the same conditions.

BACKGROUND OF THE INVENTION

Growth hormone, released by the pituitary, is a member of a cascade of hormones that regulate growth of the body and its organs. Secretion of growth hormone into the bloodstream is followed by binding to growth hormone receptor (GHR) on many cell and organ types. Growth hormone signaling is mediated by this interaction. Growth hormone signaling causes the production of another hormone, insulin-like growth factor-I (IGF-I or IGF-1), which is produced in the liver, adipose tissue and kidney and secreted into the bloodstream. About 75% of serum IGF-I is produced in the liver in response to growth hormone stimulation. Many disorders are caused by and/or associated with elevated growth hormone levels and/or elevated IGF-I levels in plasma and/or tissues including acromegaly, gigantism, retinopathy, macular degeneration, nephropathy, diabetes and cancers. This role of IGF-I in mediating many growth hormone effects is well recognized and the interrelationship is referred to as the growth hormone/insulin-like growth factor-I axis. In a normal feedback loop, IGF-I also causes the production of growth hormone by the pituitary to be reduced.

Growth hormone is produced and secreted by a set of specialized cells in the anterior pituitary. Growth hormone has direct and indirect effects on many tissues, such as stimulating bone and soft tissue growth and influencing carbohydrate, protein, and lipid metabolism. Direct biological activities of growth hormone include receptor binding, internalization of the hormone/receptor complex, and activation of proteins involved in signal transduction.

Protein and RNA transcripts for receptors of growth hormone (GHR) have been detected in many of the tissues influenced by the hormone. It was determined that a single molecule of growth hormone binds sequentially to two receptor molecules, forming an active complex. This complex, in turn, signals stimulation of other genes, including IGF-I. IGF-I, produced and secreted by the liver and other target tissues, mediates some of the indirect effects of growth hormone on growth and development. Other intracellular events occurring after the growth hormone/growth hormone receptor interaction include activation of tyrosine kinases such as Janus kinase 2 (Jak-2), which leads to phosphorylation and activation of other proteins including signal transducer and activator of transcription 5A and 5B (STAT 5A and 5B) and mitogen activated protein (MAP) kinase that, in turn, activate other proteins and genes.

The cDNA encoding the growth hormone receptor has been cloned from many species. The receptor consists of an extracellular hormone-binding region (exons 2-7), a single membrane spanning region (exon 8), and an intracellular region (exons 9-10). There are also multiple alternative 5' untranslated regions which are alternative first exons of the gene, in both the human and mouse transcripts. Growth hormone receptor has no intrinsic kinase domain, but the intracellular region plays a major role in the signal transduction process. A truncated form of the receptor, known as growth hormone binding protein (GHBP), lacks the transmembrane and intracellular regions of growth hormone receptor and is secreted into the serum. The truncated protein is produced by one of two different processes, depending on the animal species. In mice and rats, alternative splicing of growth hormone receptor precursor messenger RNA replaces the transmembrane and intracellular regions with a very short hydrophilic tail (encoded by exon 8A; 15, 16). In humans, cows, and pigs (among others), no alternative RNA splicing is apparent but instead the GHBP is produced by proteolysis of the growth hormone receptor. The function of the binding protein appears to be to modulate the level of circulating growth hormone.

Growth hormone receptor is expressed in many organs and tissues including liver, adipose tissue, muscle, cartilage, bone, tooth, kidney, eye, cardiovascular system, gut, reproductive organs, skin, brain, endocrine system and immune system.

The three-dimensional structure of the extracellular domain of growth hormone receptor has been established. It consists of two modules, each of about 100 amino acids, arranged as two sandwiches each with seven strands of beta-sheet. The secreted form of the extracellular domain of growth hormone receptor is the GHBP.

The growth hormone receptor is biologically responsive to growth hormone stimulation. JAK2 is the primary effector molecule for growth hormone receptor signaling. JAK2 is activated post growth hormone receptor dimerisation. When the growth hormone dimerizes its receptors, the JAKs are brought close together, and with proper alignment transphosporylate each other, leading to full activation. The intracellular targets for the JAKs include tyrosine residues in the receptor cytoplasmic domain itself, which in turn activate SH2 domains (STATS, Shc and SHP2). These may go on to activate the MAP kinase pathway, which regulates cell proliferation. JAK2 also phosphorylates and activates other signaling molecules, such as IRS-1 and -2 and phosphatidyl 3-inositol kinase, which are important parts of the insulin signaling mechanism and may account for the insulin-like actions of growth hormone. Activated JAK2 also phosphorylates STATS, and when activated, is involved in the transcription of a number of genes.

Growth hormone receptor activation leads to many actions in many organs including the following outcomes in the following organs:

Liver: Increased secretion of insulin-like growth factor-I, synthesis of plasma proteins, regulation of nitrogen balance enzymes, increased carbohydrate synthesis/storage, and increased fat breakdown; Adipose Tissue: Breakdown of fat stores; Muscle: Increased protein synthesis, decreased protein breakdown; Cartilage: Increased height by increasing proliferation and differentiation of chondrocytes in growth plate; Bone & Tooth: Increased turnover of tissue, both synthesis and breakdown; Kidney: Increased sodium, bicarbonate and water retention; Eye: increased retinal neovascularization; Cardiovascular: Hypertrophy, increased contractility, stroke volume, cardiac output; Gut: Hypertrophy, increased amino acid, sodium, calcium, phosphate and B12 uptake; Reproductive System: Increased sperm production and motility, increased accessory gland secretion in male, increased number of follicles and ovulation rate, increased follicular maturation rate, increased milk production; Skin: Increased skin thickness and strength, increased hair growth and thickness; Brain: Increased neuron proliferation and connectivity prenatally, increased myelin formation, improved long-term memory; Endocrine System: Increased insulin synthesis and secretion, increased adrenal steroidogenesis; Immune System: Increased immune cell proliferation, increased killing by monocytes, macrophages and NK cells, increased antibody production.

Downstream from growth hormone receptor in the growth hormone signaling pathway are IGF-I and IGF-I receptor. The insulin-like growth factors (IGFs) are important in proliferation. In particular, IGF-I and IGF-2 are ubiquitous polypeptides each with potent mitogenic effects on a broad range of cells. Molecules of the insulin-like growth factor type are also known as "progression factors" promoting "competent" cells through DNA synthesis. The insulin-like growth factors act through a common receptor known as the Type I receptor or IGF-IR, which is tyrosine kinase linked.

Particular proteins, referred to as insulin-like growth factor binding proteins (IGFBPs), appear to be involved in autocrine/paracrine regulation of tissue insulin-like growth factor availability (Rechler and Brown, *Growth Regulation*, 1992, 2, 55-68). Six IGFBPs have so far been identified. The exact effects of the IGFBPs are not clear and observed effects in vitro have been inhibitory or stimulatory depending on the experimental method employed (Clemmons, *Growth Regn.* 1992, 2, 80,). There is some evidence, however, that certain IGFBPs are involved in targeting insulin-like growth factor-I to its cell surface receptor. Also expression of IGFBP-3 is regulated by growth hormone (Karen et al, supra).

The IGF-IR is a tyrosine kinase linked cell surface receptor (Ullrich et al., *EMBO J.* 1986, 5, 2503-2512,) that regulates cell division, transformation and apoptosis in many cell types (LeRoith et al., *Endocr. Rev.*, 1995, 16, 143-163; Rubin and Baserga, *Laboratory Investigation*, 1995, 73, 311-331).

If feedback regulation of growth hormone production is lost and the pituitary continues to release aberrant amounts of growth hormone, the level of insulin-like growth factor-I continues to rise, leading to bone growth and organ enlargement. The excess growth hormone also causes changes in sugar and lipid metabolism, which may lead to diabetes. Defects in the growth hormone signalling pathway often lead to abnormalities of stature and body and/or organ size. Mutations in the growth hormone receptor gene result in extreme short stature (Laron's syndrome). Excessive production of growth hormone can lead to acromegaly or gigantism.

Acromegaly and gigantism are related growth disorders wherein growth hormone excess, sometimes caused by pituitary tumor, causes progressive cosmetic disfigurement and systemic organ manifestations. It affects 40-50 per million people worldwide with about 15,000 sufferers in each of the US and Europe and an annual incidence of about 4-5 per million. It is initially characterized by abnormal growth of the hands and feet and bony changes in the facial features. Patients have reduced quality of life with overgrowth of the jaw, enlargement of hands and feet, deepening of the voice, thickening of skin, offensive body odor, articular cartilage problems, hyperphosphatemia, peripheral neuropathies, higher blood pressure, diabetes, heart disease, and cancer, and have a reduced life expectancy if untreated. The mortality rate is about twice that of the normal population due to cardiorespiratory and cardiovascular diseases, diabetes and neoplasia, particularly colon cancer. The goal of current treatment is to reverse the effects of the hypersecretion of growth hormone and normalize production of IGF-I which is elevated by about 50% in these patients. When effective, treatment moderates disease symptoms and disease-associated mortality.

Gigantism, the disease of excess growth hormone in children, is a rare disorder. In gigantism, excessive linear growth occurs whilst epiphyseal growth plates are open during childhood with growth hormone excess caused via a benign pituitary tumor. In both gigantism and acromegaly, all growth parameters are affected, although not necessarily symmetrically. Many of the growth related outcomes are mediated by elevated levels of serum IGF-I. Serum blood levels of IGF-I are elevated by about 50% in patients and reduction of serum IGF-I is used to monitor treatment success.

Treatments for acromegaly and gigantism involve the ability to lower the elevated IGF-I in plasma. This may be achieved by surgical removal and radiation therapy of the benign pituitary tumor but this is effective in only 50% of patients. Dopamine agonists such as bromocriptine mesylate or cabergoline may be dosed orally which is convenient but they only reduce growth hormone production and associated IGF-I sufficiently in 10% of cases. They also produce significant gastrointestinal and central side effects in 20-30% of patients. Also used in treatment of acromegaly are the somatostatin analogues such as Sandostatin or octreotide, which inhibit the release of growth hormone releasing hormone (GHRH) from the hypothalamus, and/or pituitary and thereby reducing production of growth hormone in the pituitary. This compound is effective in 60-65% patients with acromegaly but it must be injected under the skin every 8 hours or intramuscularly for effective treatment.

Recently a growth hormone receptor antagonist, Trovert, also known as Somavert, Pegvisomant and B2036-PEG, was shown in clinical trials to be effective in 90-95% of patients. Clinical trial experience to date shows a 10% drop-out rate and adverse effects such as liver dysfunction. Trovert is a growth hormone molecule with a 9 amino acid substitution with 4-5 pegylations to increase half life. Like all modified proteins it is immunogenic, with antibodies being made to Trovert within 1 month of dosing. This can impact Trovert's short and long term utility and makes dosing difficult to predict. Trovert was initially dosed once per month by subcutaneous (sc) administration, but current clinical practice suggests dosing will need to be once/day sc. Trovert interferes with growth hormone binding to its receptor but not the Growth Hormone Binding Protein (GHBP) fragment of the growth hormone receptor. GHBP binds growth hormone prolonging its action, which can be disadvantageous in conditions involving excess growth hormone and/or excess IGF-I. Pegylation may also impact on Trovert's long term safety profile.

Diabetes and its life threatening complications such as diabetic retinopathy and nephropathy are also disorders associated with growth hormone and/or IGF-I levels. First line treatment of these conditions involves controlling hyperglycemia. Drugs that control diabetes reduce the incidence of nephropathy by 60% and also reduce the incidence of retinopathy. However, about half of all diabetics are unaware of disease and therefore remain untreated, so diabetic nephropathy and retinopathy are likely to remain a major condition requiring other treatments. In retinopathy surgical ablative treatments such as laser pan-retinal photocoagulation are used but these remain incompletely effective and destroy retinal tissue, causing partial vision field loss. In type I diabetics ACE and AII inhibitors decrease albuminuria excretion by acting on the kidney and in Type II diabetics the same inhibitors act locally on kidney and also decrease blood pressure to reduce the risk of death from kidney failure by another 50%. However, 20-30% of patients remain resistant to treatment with current glycemic control drugs and ACE drugs. There is thus a need for better treatments.

The underlying cause of diabetes, diabetic retinopathy and diabetic nephropathy may be insulin related hyperglycemia, but growth hormone and/or insulin-like growth factor-I excess is also important. Octreotide inhibitors of GHRH that decrease production of pituitary growth hormone, reducing systemic levels of growth hormone and IGF-I, and/or modulating local tissue levels show potential in the clinic. A study with octreotide by Grant et al., *Diabetes Care*, 2000, 2, 504-9) reducing sIGF-1 by 51% at maximally tolerated doses of octreotide 5000 µg/day sc reduced the need for laser surgery in retinopathy patients to 1 patient out of 22 rather than 9/22 in placebo in a 15 month study. Also ocular disease was reduced to 27% vs placebo of 42% bordering on significance (P 0.06). Three human studies using octreotide at levels that reduced sIGF1 45%, about 20% and about 10% respectively were at least partly effective in clinical trials of nephropathy. The outcome reported by Serin et al. (*JAMA*, 1991, 265, 888-92) with 11 patients used high doses of octreotide in a 12 week study that reduced serum IGF-I by 45%. At the time it was stated to be the best effect observed on reducing glomerular filtration rate with a 22-33% reduction relative to placebo. This dose, however, was near maximally tolerated doses of octreotide.

Animal pathology model studies with octreotide and Trovert also support the view that agents that modulate the growth hormone/insulin-like growth factor-I axis are beneficial in the treatment of these diabetic conditions. Growth hormone and its receptor are implicated in the induction of glomerular hypertrophy and sclerosis in partial nephrectomy and diabetic nephropathy with somatostatin inhibitors octreotide and PTR-3173 (Groenbaek et al., *J. Endocrinol.*, 2002, 172, 637-643 and Landau et al, *Kidney International*, 2001, 60, 505-512) and growth hormone receptor antagonist, G120K-PEG, a weaker version of Trovert, preventing complications in type I and Type II diabetic mice (Chen et al, *Endocrinology*, 1996, 137, 11, 5136-5165; Flyvbjerg et al, *Diabetes*, 1999, 40, 377-382, and Segev et al., *J. Am. Soc. Nephrol.* 1999, 10, 2374-81). Growth hormone and its receptor are implicated in the induction of retinal neovascularization through IGF-I with somatostatin inhibitors octreotide and growth hormone receptor antagonist MK678, inhibiting retinal neovascularization in mice. MK678 reduction of neovascularization correlated with low serum IGF-I (Smith et al, *Science*, 1997, 276, 1706-9). Oxygen induced retinopathy in the mouse was also responsive to octreotide as reported by Higgins et al., *Exp Eye Res*, 2002, 74, 553-9.

Macular degeneration is also associated with elevated growth hormone and/or IGF-I levels. Age-related macular degeneration (AMD) is caused by deterioration of the central part of the retina, the macula, resulting in loss of detailed vision. Wet AMD, the less common form, is caused by leakage from new blood vessels growing behind the retina. The growth hormone/IGF-I axis is involved in formation of new blood vessels relevant to this condition and to diabetic retinopathy.

Various cancers are also associated with aberrant growth hormone and/or IGF-I levels. Reduction of serum IGF-I by 20-50% using Trovert decreased tumor volume in breast cancer in animal models and helped in colon cancer, liver metastasis, and meningiomas (Friend et al, *Proceedings 11th NCI EORTC. AACR Symposium and Friend, Growth Horm. IGF Res.*, Jun. 11, 2001 Suppl A: S121-3). The incidence of breast, colon, prostate, and lung cancer is increased in individuals in the high normal range of serum IGF-I. There have been no clinical studies with Trovert in cancers. However, octreotide is indicated for gastro-pancreatic cancers.

Other conditions that may be associated with elevated growth hormone and/or IGF-I levels include rheumatoid arthritis. A pilot clinical study showed octreotide was useful for the treatment of active refractory rheumatoid arthritis in a subset of patients (Paran et al., *Ann. Rheum. Dis.*, 2001, 60, 888-91. with comments and authors' reply in *Ann. Rheum. Dis.*, 2002, 61, 1117).

Longevity may also be improved with modulation of growth hormone receptor (Coschigano et al., *Endocrinology*, 2000, 141, 2608-2613). There was a significant increase in lifespan of nearly a year in double knockout animals with low levels of IGF-I and high levels of growth hormone.

Another application to modifying levels of growth hormone and/or IGF-I via the growth hormone receptor may enable stem cell differentiation towards neural cell production as growth hormone inhibits neuronal differentiation of neural progenitor cells (Turnley et al., *Nature Neuroscience*, 7 Oct. 2002, published online). Other applications will be known to those skilled in the art.

Although the underlying roles in various disease or conditions may be different, the above conditions arise at least in part from incorrect levels of expression of local and/or systemic growth factors growth hormone and IGF-I and/or their receptors growth hormone receptor and IGF-IR. In these situations, dopamine agonists, somatostatin antagonists, and growth hormone receptor antagonists targeting the proteins have been used and/or shown potential.

While a range of treatments have been developed for agents that modify the growth hormone-insulin-like growth factor axis, and growth hormone receptor and IGF-IR, none is completely effective and/or free of adverse side effects. Moreover, there is potential disadvantages in the routes and/or frequencies of administration that can affect compliance.

It is therefore an object of the present invention to provide novel products and compositions wherein one or more of the above problems and limitations are ameliorated.

In the last decade, there have been reports of the use of antisense oligonucleotides to explore gene function and several reports in the development of nucleic acid based drugs. Antisense oligonucleotides inhibit mRNA translation via a number of alternative ways including destruction of the target mRNA through RNase H recruitment, or interference with RNA processing, nuclear export, folding or ribosome scanning.

Pellegrini et al. attempted to block growth hormone receptor synthesis in the central nervous system by infusing intracerebroventricularly an antisense 18-mer oligonucleotide complementary to a portion of the coding sequence of the rat growth hormone receptor mRNA overlapping the translation initiation codon. J. Neurosci. 1996, 16, 8140-8148.

The current invention as exemplified herein for the first time, demonstrates that an antisense oligonucleotide targeted specifically to the growth hormone receptor reduces a clinical parameter of growth hormone activity, namely serum insulin-like growth factor-I. Importantly, our antisense studies teach the ability to use antisense to growth hormone receptor to reduce serum insulin-like growth factor-I by similar degrees required for the clinical treatment of gigantism or acromegaly. Serum insulin-like growth factor-I levels are elevated in acromegaly patients and reduced at human therapeutic Trovert doses by 50% in both 12 week studies (Trainer et al, The New England J of Med Apr. 20, 2000) which show a decrease by 1.3 to 2 fold, and in long term greater than 1 year studies as reported by van der Lely et al., Lancet Nov. 24, 2001: 358 (9295) 1754-1759.

Similar levels of reduction of serum insulin-like growth factor-I are also reported with octreotide in 15 month clinical trials of diabetic retinopathy (Grant et al, Supra) and in clinical trials in diabetic nephropathy (Serri et al, supra). Similar levels of reduction of 20-50% is also sufficient to prevent the growth of certain cancer in animal models (Friend, supra).

The present invention teaches for the first time that growth hormone receptor antisense can achieve human and animal equivalent therapeutic outcomes. It teaches that antisense to the mRNA of one component of the growth hormone/insulin-like growth factor-I axis, namely growth hormone receptor, can affect another parameter in the axis, e.g., IGF-I. Importantly, it teaches that antisense targeting any other target in the growth hormone/insulin-like growth factor-I axis is potentially capable of achieving therapeutic levels in conditions dependent on excess growth hormone or insulin-like growth factor-I levels.

SUMMARY OF THE INVENTION

The present invention is directed to compounds, especially nucleic acid and nucleic acid-like oligomers, which are targeted to a nucleic acid encoding growth hormone receptor, and which modulate growth hormone signaling or the growth hormone/insulin-like growth factor-I axis, particularly the expression of growth hormone receptor and/or insulin-like growth factor-I. Further provided are methods of screening for modulators of growth hormone receptor and/or insulin-like growth factor-I and methods of modulating the expression of growth hormone receptor and/or insulin-like growth factor-I in cells, tissues or animals comprising contacting said cells, tissues or animals with one or more of the compounds or compositions of the invention. Diagnostic methods and kits are also provided. Methods of treating an animal, particularly a human, suspected of having or being prone to a disease or condition associated with growth hormone signaling or the growth hormone/insulin-like growth factor-I axis, particularly the expression of growth hormone receptor and/or insulin-like growth factor-I, are also set forth herein.

DETAILED DESCRIPTION OF THE INVENTION

A. Overview of the Invention

The present invention employs compounds, preferably oligonucleotides and similar species for use in modulating the function or effect of nucleic acid molecules encoding growth hormone receptor. This is accomplished by providing oligonucleotides which specifically hybridize with one or more nucleic acid molecules encoding growth hormone receptor. As used herein, the terms "target nucleic acid" and "nucleic acid molecule encoding growth hormone receptor" have been used for convenience to encompass DNA encoding growth hormone receptor, RNA (including pre-mRNA and mRNA or portions thereof (including both coding and noncoding regions), transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of growth hormone receptor. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes growth hormone receptor.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding growth hormone receptor, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5' UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3' UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

In mouse, rat and monkey, growth hormone binding protein, which is the soluble shortened form of growth hormone receptor, is produced by alternative splicing of the growth hormone receptor primary transcript. In some embodiments it may be preferred to target regions of the transcript which are present in both the growth hormone receptor transcript and in the shorter growth hormone binding protein transcript. In other embodiments it may be preferable to target regions of the mRNA which are only present in the longer growth hormone receptor transcript. In humans, cows, and pigs (among others), no alternative RNA splicing is apparent but instead the shorter growth hormone binding protein is produced by proteolysis of the growth hormone receptor. It will be understood that in the context of this invention, "nucleic acid encoding growth hormone receptor" thus includes nucleic acid encoding growth hormone binding protein."

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The growth hormone receptor mRNA has alternative 5' untranslated regions and one or more of these may be preferred for targeting.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of growth hormone receptor. "Modulators" are those compounds that decrease or increase the expression of a nucleic acid molecule encoding growth hormone receptor and which comprise at least an 8-nucleobase portion which is complementary to a preferred target segment. The screening method comprises the steps of contacting a preferred target segment of a nucleic acid molecule encoding growth hormone receptor with one or more candidate modulators, and selecting for one or more candidate modulators which decrease or increase the expression of a nucleic acid molecule encoding growth hormone receptor.

Once it is shown that the candidate modulator or modulators are capable of modulating (e.g. either decreasing or increasing) the expression of a nucleic acid molecule encoding growth hormone receptor, the modulator may then be employed in further investigative studies of the function of growth hormone receptor, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between growth hormone receptor and a disease state, phenotype, or condition. These methods include detecting or modulating growth hormone receptor comprising contacting a sample, tissue, cell, or organism with the compounds of the present invention, measuring the nucleic acid or protein level of growth hormone receptor and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Riochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The compounds of the invention are useful for research and diagnostics, because these compounds hybridize to nucleic acids encoding growth hormone receptor. For example, oligonucleotides that are shown to hybridize with such efficiency and under such conditions as disclosed herein as to be effective growth hormone receptor inhibitors will also be effective primers or probes under conditions favoring gene amplification or detection, respectively. These primers and probes are useful in methods requiring the specific detection of nucleic acid molecules encoding growth hormone receptor and in the amplification of said nucleic acid molecules for detection or for use in further studies of growth hormone receptor. Hybridization of the antisense oligonucleotides, particularly the primers and probes, of the invention with a nucleic acid encoding growth hormone receptor can be detected by means known in the art. Such means may include conjugation of an enzyme to the oligonucleotide, radiolabelling of the oligonucleotide or any other suitable detection means. Kits using such detection means for detecting the level of growth hormone receptor in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals.

The compounds of the present invention have been shown to reduce expression of growth hormone receptor and to reduce levels of IGF-I. These compounds are therefore believed to be useful for prevention, delay or treatment of conditions associated with growth hormone receptor or with the growth hormone/insulin-like growth factor-I axis, including acromegaly, gigantism, age-related macular degeneration, diabetic retinopathy, diabetic nephropathy, diabetes, arthritis and growth hormone and IGF-I dependent tumors.

For therapeutics, an animal, preferably a human, suspected of having a disease or disorder which can be treated by modulating the expression of growth hormone receptor is treated by administering antisense compounds in accordance with this invention. For example, in one non-limiting embodiment, the methods comprise the step of administering to the animal in need of treatment, a therapeutically effective amount of a growth hormone receptor inhibitor. The growth hormone receptor inhibitors of the present invention effectively inhibit the activity of the growth hormone receptor protein or inhibit the expression of the growth hormone receptor protein. In one embodiment, the activity or expression of growth hormone receptor in an animal is inhibited by about 10%. Preferably, the activity or expression of growth hormone receptor in an animal is inhibited by about 30%. More preferably, the activity or expression of growth hormone receptor in an animal is inhibited by 45% or more.

For example, the reduction of the expression of growth hormone receptor may be measured in serum, adipose tissue, liver or any other body fluid, tissue or organ of the animal. Preferably, the cells contained within said fluids, tissues or organs being analyzed contain a nucleic acid molecule encoding growth hormone receptor protein and/or the growth hormone receptor protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2, 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ONH$_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$$CH_2$$OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-O$CH_2$$CH_2$$CH_2$$NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 21-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$, group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications, pages* 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents. Sodium is a suitable pharmaceutical salt, particularly for oligonucleotide compounds.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Also preferred antisense compounds are those capable of oral administration such as the 2'MOE antisense compounds and morpholino phosphorodiamidates. This provides further convenience for users relative to growth hormone receptor compounds in the prior art. Preferred compounds in the treatment of some conditions will be those that distribute broadly and thus capable of both local and/or systemic effects via the liver. It will be understood however, that in other conditions distribution to fewer organs may be preferred.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intra-thecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially. Particularly preferred combinations comprise Octreotide, Trovert and/or other inhibitor(s) or antagonists of growth hormone, insulin-like growth factor-I, IGFBP-3, growth hormone receptor or insulin-like growth factor1 receptor.

Compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

Preferred antisense oligonucleotides are made with chemistries capable of low frequency of dosing, i.e., once a day, once a week or less often. Particularly preferred antisense chemistries are those used herein which may be dosed once every second day and able to be dosed at least once per week sc, if not less frequently at once per month, based on the observations of antisense of the same class. This is less frequently than Trovert in same animal model, which was dosed every day, and less frequently than current clinical experience with Trovert. This provides enormous convenience for treatment of this chronic condition which may potentially improve compliance.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyluridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleotide. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand,.* 1990, 44, 639-641; Reddy, M. P., et al., *Tetrahedrom Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound.

Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH₄OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methylchimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Growth Hormone Receptor In accordance with the present invention, a series of nucleic acid duplexes comprising the antisense compounds of the present invention and their complements can be designed to target growth hormone receptor. In one embodiment these nucleic acid duplexes are double-stranded RNA compounds (small interfering RNAs or siRNAs). In general, active sites for RNase H-dependent antisense oligonucleotides predict active sites for siRNA (Vickers et al., 2003, *J. Biol Chem.* 278, 7108-7118). In one embodiment of the invention, the nucleobase sequence of the antisense strand of the duplex comprises at least a portion of an oligonucleotide sequence shown in Table 1. Alternatively, a new "gene walk" in which a series of dsRNAs targeted to growth hormone receptor are synthesized and tested may be used.

The ends of the dsRNA strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The duplex may be a unimolecular or bimolecular duplex; i.e, the two strands may be connected to each other directly or by means of a linker, or may be separate molecules.

By way of example, a duplex comprising an antisense strand having the sequence CGAGAGGCGGACGGGACCG and having a two-nucleobase overhang of deoxythymidine (dT) would have the following structure:

In another embodiment, a duplex comprising an antisense strand having the same sequence CGAGAGGCGGACGG-GACCG may be prepared with blunt ends (no single stranded overhang) as shown:

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate growth hormone receptor expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

MCF7:

The human breast carcinoma cell line MCF-7 was obtained from the American Type Culture Collection (Manassas, Va.). MCF-7 cells were routinely cultured in DMEM low glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 65-75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μl of OPTI-MEM™-1 containing 3.75 μg/mL LIPOFECTIN™ (a 1:1 (w/w) liposome formulation of the cationic lipid N-[1-(2,3-dioleyloxy)propyl]-n,n,n-trimethylammonium chloride (DOTMA) and dioleoyl photidylethanolamine (DOPE) in membrane filtered water) (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Growth Hormone Receptor Expression

Antisense modulation of growth hormone receptor expression can be assayed in a variety of ways known in the art. For example, growth hormone receptor mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of growth hormone receptor can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to growth hormone receptor can be identified and obtained from a variety of sources, such as the MSRS catalog of antibodies (Aerie Corporation, Birmingham, Mich.), or can be prepared via conventional monoclonal or polyclonal antibody generation methods well known in the art.

Reduction in expression of growth hormone receptor may also be indirectly measured by measuring decreases in insulin-like growth factor-I in serum or other bodily fluid, tissues or organs.

Example 11

Design of Phenotypic Assays and In Vivo Studies for the Use of Growth Hormone Receptor Inhibitors Phenotypic Assays Once growth hormone receptor inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of growth hormone receptor in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with growth hormone receptor inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the growth hormone receptor inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or growth hormone receptor inhibitor. Furthermore, to prevent the doctors from being biased in treatments, they are not informed as to whether the medication they are administering is a growth hormone receptor inhibitor or a placebo. Using this randomization approach, each volunteer has the same chance of being given either the new treatment or the placebo.

Volunteers receive either the growth hormone receptor inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding growth hormone receptor or growth hormone receptor protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and growth hormone receptor inhibitor treatment. In general, the volunteers treated with placebo have little or no response to treatment, whereas the volunteers treated with the growth hormone receptor inhibitor show positive trends in their disease state or condition index at the conclusion of the study.

Example 12

RNA Isolation

Poly(A)+mRNA Isolation

Poly(A)+mRNA was isolated according to Miura et al., (*Clin. Chem.*, 1996, 42, 1758-1764). Other methods for poly (A)+mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIA-VAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIA-VAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Growth Hormone Receptor mRNA Levels

Quantitation of growth hormone receptor mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5× PCR buffer minus $MgCl_2$, 6.6 mM $MgCl_2$, 375 µM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human growth hormone receptor were designed to hybridize to a human growth hormone receptor sequence, using published sequence information (GenBank accession number NM_000163.1, incorporated herein as SEQ ID NO:4). For human growth hormone receptor the PCR primers were:

forward primer: GATGTCCCAATGTGACATGCA (SEQ ID NO: 5)

reverse primer: AAGTAGGCATTGTCCATAAGGAAGTT (SEQ ID NO: 6) and the PCR probe was: FAM-CCGGAAATGGTCTCACTCT-GCCAAGA-TAMRA (SEQ ID NO: 7) where FAM is the fluorescent dye and TAMRA is the quencher dye. For human GAPDH the PCR primers were:

forward primer: GAAGGTGAAGGTCGGAGTC SEQ ID NO:8)

reverse primer: GAAGATGGTGATGGGATTTC (SEQ ID NO:9) and the

PCR probe was: 5' JOE-CAAGCTTCCCGTTCTCAGCC-TAMRA 3' (SEQ ID NO: 10) where JOE is the fluorescent reporter dye and TAMRA is the quencher dye.

Probes and primers to mouse growth hormone receptor were designed to hybridize to a mouse growth hormone receptor sequence, using published sequence information (GenBank accession number NM_010284.1, incorporated herein as SEQ ID NO:11). For mouse growth hormone receptor the PCR primers were:

forward primer: TTGACGAAATAGTGCAACCTGATC (SEQ ID NO:12)

reverse primer: CGAATCCCGGTCAAACTAATG (SEQ ID NO: 13) and the

PCR probe was: FAM-CATTGGCCTCAACTGGACTT-TACTAA-TAMRA (SEQ ID NO: 14) where FAM is the fluorescent reporter dye and TAMRA is the quencher dye. For mouse GAPDH the PCR primers were:
forward primer: GGCAAATTCAACGGCACAGT(SEQ ID NO:15)
reverse primer: GGGTCTCGCTCCTGGAAGAT(SEQ ID NO:16) and the
PCR probe was: 5' JOE-AAGGCCGAGAATGGGAAGCT-TGTCATC-TAMRA 3' (SEQ ID NO: 17) where JOE is the fluorescent reporter dye and TAMRA is the quencher dye.

Example 14

Northern Blot Analysis of Growth Hormone Receptor mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human growth hormone receptor, a human growth hormone receptor specific probe was prepared by PCR using the forward primer GATGTCCCAATGTGACAT-GCA (SEQ ID NO: 5) and the reverse primer AAGTAG-GCATTGTCCATAAGGAAGTT (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse growth hormone receptor, a mouse growth hormone receptor specific probe was prepared by PCR using the forward primer TTGACGAAATAGTGCAACCTGATC (SEQ ID NO: 12) and the reverse primer CGAATCCCGGT-CAAACTAATG (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Growth Hormone Receptor Expression by Chimeric Phosphorothioate Oligonucleotides Having 2'-MOE Wings and a Deoxy Gap In accordance with the present invention, a series of antisense compounds were designed to target different regions of the human growth hormone receptor RNA, using published sequences (GenBank accession number NM_000163.1, incorporated herein as SEQ ID NO: 4, and the complement of positions 468085 to 502183 of the sequence with GenBank accession number NT_006702.8, incorporated herein as SEQ ID NO: 18). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2$^1$-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human growth hormone receptor mRNA levels by quantitative real-time PCR as described in other examples herein. Data are averages from three experiments in which MCF7 cells were treated with the antisense oligonucleotides of the present invention. The positive control for each datapoint is identified in the table by sequence ID number. If present, "N.D." indicates "no data".

TABLE 1

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 227452 | Coding | 4 | 332 | tcagggcattctttccattc | 79 | 19 | 1 |
| 227453 | Coding | 4 | 337 | cataatcagggcattctttc | 52 | 20 | 1 |
| 227464 | Coding | 4 | 947 | cctttaatctttggaactgg | 58 | 21 | 1 |
| 227468 | Coding | 4 | 1079 | tcatcaatatctagctcaat | 62 | 22 | 1 |
| 227469 | Coding | 4 | 1124 | cttagaagtctgtctgtgtc | 63 | 23 | 1 |
| 227475 | Coding | 4 | 1514 | cctgctggtgtaatgtcgct | 68 | 24 | 1 |
| 227480 | Coding | 4 | 1724 | atgtaaatgtcctcttggtt | 66 | 25 | 1 |

TABLE 1-continued

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 227481 | Coding | 4 | 1729 | tggtgatgtaaatgtcctct | 45 | 26 | 1 |
| 227482 | Coding | 4 | 1734 | ttctgtggtgatgtaaatgt | 53 | 27 | 1 |
| 227483 | Coding | 4 | 1739 | aggctttctgtggtgatgta | 75 | 28 | 1 |
| 227484 | Coding | 4 | 1744 | tggtaaggctttctgtggtg | 63 | 29 | 1 |
| 227488 | Coding | 4 | 1922 | agttggtctgtgctcacata | 86 | 30 | 1 |
| 227489 | Coding | 4 | 1927 | tgttcagttggtctgtgctc | 75 | 31 | 1 |
| 227490 | Coding | 4 | 1936 | gcatgattttgttcagttgg | 67 | 32 | 1 |
| 227499 | 3'UTR | 4 | 2656 | tataaagggctttgtaaaa | 14 | 33 | 1 |
| 227500 | 3'UTR | 4 | 4043 | catagcagcaaagtagcaga | 69 | 34 | 1 |
| 227501 | 3'UTR | 4 | 4183 | gctattttggctatagaaa | 64 | 35 | 1 |
| 227502 | 3'UTR | 4 | 4197 | gattgaggtatttagctatt | 56 | 36 | 1 |
| 272302 | Start Codon | 4 | 31 | gatccatacctgtaggacct | 60 | 37 | 1 |
| 272303 | Start Codon | 4 | 36 | ccagagatccatacctgtag | 55 | 38 | 1 |
| 272304 | Coding | 4 | 115 | tgctaaggatagctgctgtg | 48 | 39 | 1 |
| 272305 | Coding | 4 | 160 | ttgtctttaggcctggatta | 68 | 40 | 1 |
| 272306 | Coding | 4 | 170 | ttagaagaatttgtctttag | 13 | 41 | 1 |
| 272307 | Coding | 4 | 185 | gtgaatttaggctccttaga | 55 | 42 | 1 |
| 272308 | Coding | 4 | 274 | gctgtatgggtcctaggttc | 57 | 43 | 1 |
| 272309 | Coding | 4 | 362 | taacagctgttttccccagc | 85 | 44 | 1 |
| 272310 | Coding | 4 | 439 | tttcatccactgtaccacca | 76 | 45 | 1 |
| 272311 | Coding | 4 | 468 | ttgcactatttcatcaacag | 47 | 46 | 1 |
| 272312 | Coding | 4 | 480 | gggtggatctggttgcacta | 57 | 47 | 1 |
| 272313 | Coding | 4 | 564 | attgcgtggtgcttcccatc | 77 | 48 | 1 |
| 272314 | Coding | 4 | 652 | tagggtccatcattttccat | 56 | 49 | 1 |
| 272315 | Coding | 4 | 684 | caatgagtacactggaactg | 53 | 50 | 1 |
| 272316 | Coding | 4 | 752 | aactcgccataatttccaga | 64 | 51 | 1 |
| 272317 | Coding | 4 | 857 | agcccaaatattccaaagat | 65 | 52 | 1 |
| 272318 | Coding | 4 | 913 | tcagcattttaatcctttgc | 55 | 53 | 1 |
| 272319 | Coding | 4 | 979 | attttccttccttgaggaga | 67 | 54 | 1 |
| 272320 | Coding | 4 | 1000 | agattgtgttcacctcctct | 70 | 55 | 1 |
| 272321 | Coding | 4 | 1053 | aacccaagagtcatcactgt | 64 | 56 | 1 |
| 272322 | Coding | 4 | 1084 | ctggctcatcaatatctagc | 84 | 57 | 1 |
| 272323 | Coding | 4 | 1110 | tgtgtctgattcctcagtct | 67 | 58 | 1 |
| 272324 | Coding | 4 | 1236 | tatgtcattggcattgaaat | 53 | 59 | 1 |

TABLE 1-continued

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 272325 | Coding | 4 | 1302 | aaggcataagagatctgctt | 66 | 60 | 1 |
| 272326 | Coding | 4 | 1420 | actcagctccttcagtagga | 77 | 61 | 1 |
| 272327 | Coding | 4 | 1560 | ggacatccctgccttattct | 60 | 62 | 1 |
| 272328 | Coding | 4 | 1623 | ggcattgtccataaggaagt | 85 | 63 | 1 |
| 272329 | Coding | 4 | 1651 | acttttggcatctgcctca | 63 | 64 | 1 |
| 272330 | Coding | 4 | 1656 | gatgcacttttggcatctg | 47 | 65 | 1 |
| 272331 | Coding | 4 | 1861 | cagtcgcattgagtatgagg | 67 | 66 | 1 |
| 272332 | Coding | 4 | 1884 | ctctttgtcaggcaagggca | 75 | 67 | 1 |
| 272333 | Coding | 4 | 1913 | gtgctcacatagccacatga | 72 | 68 | 1 |
| 272334 | Stop Codon | 4 | 1949 | aagaaaggctaaggcatgat | 61 | 69 | 1 |
| 272335 | 3'UTR | 4 | 1973 | aaatacgtagctcttgggaa | 47 | 70 | 1 |
| 272336 | 3'UTR | 4 | 2196 | caatcactgctactaaacag | 69 | 71 | 1 |
| 272337 | 3'UTR | 4 | 2249 | aaacatagccattcaatgct | 39 | 72 | 1 |
| 272338 | 3'UTR | 4 | 2337 | gtgctatggtttgcattcaa | 78 | 73 | 1 |
| 272339 | 3'UTR | 4 | 2454 | gttttacatatccaaactat | 72 | 74 | 1 |
| 272340 | 3'UTR | 4 | 2853 | catcaaccaagatttggtga | 69 | 75 | 1 |
| 272341 | 3'UTR | 4 | 2988 | gaggctatagatcttatctc | 65 | 76 | 1 |
| 272342 | 3'UTR | 4 | 3271 | tagtgagaaagaaagtttct | 45 | 77 | 1 |
| 272343 | 3'UTR | 4 | 3765 | aatgctctcaagaatgatgt | 48 | 78 | 1 |
| 272344 | 3'UTR | 4 | 3980 | acactcaattctagcttttc | 60 | 79 | 1 |
| 272345 | 3'UTR | 4 | 4011 | catctattacaaataacatg | 24 | 80 | 1 |
| 272346 | 3'UTR | 4 | 4057 | ctcttggagaaaaccatagc | 67 | 81 | 1 |
| 272347 | 3'UTR | 4 | 4097 | tctacactgatgatacttta | 62 | 82 | 1 |
| 272348 | 3'UTR | 4 | 4120 | cacagctttgaattgaatta | 57 | 83 | 1 |
| 272349 | 3'UTR | 4 | 4133 | agtcttccaaacacacagct | 68 | 84 | 1 |
| 272350 | 3'UTR | 4 | 4156 | aggctgttgtgaaatagtaa | 67 | 85 | 1 |
| 272351 | 3'UTR | 4 | 4170 | atagaaatgttgtcaggctg | 57 | 86 | 1 |
| 272352 | 3'UTR | 4 | 4218 | ccaaaatgacattctgagac | 77 | 87 | 1 |
| 272353 | 3'UTR | 4 | 4245 | ataatggcttatgtggccac | 72 | 88 | 1 |
| 272354 | intron: | 18 | 2571 | agttatgtgaccctgattga | 65 | 89 | 1 |
| 272355 | intron: exon junction | 18 | 6418 | ttgagtgttcctaaaatgaa | 24 | 90 | 1 |
| 272356 | intron | 18 | 8405 | atggaggctggaggttcaaa | 63 | 91 | 1 |
| 272357 | intron: exon junction | 18 | 22712 | tagggtccatcttcaagac | 62 | 92 | 1 |

TABLE 1-continued

Inhibition of human growth hormone receptor mRNA levels by
chimeric phosphorothioate oligonucleotides having 2'-MOE
wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 272358 | intron | 18 | 25543 | tctccagatagaatctaaac | 53 | 93 | 1 |
| 272359 | intron | 18 | 29755 | tccaaatattctggtacttt | 72 | 94 | 1 |
| 272360 | exon: intron junction | 18 | 29935 | tattagttaccttgaggaga | 0 | 95 | 1 |
| 272361 | intron: exon junction | 18 | 30267 | attttccttcctagaaaata | 10 | 96 | 1 |

As shown in Table 1, SEQ ID NOs 19, 20, 21, 22, 23, 24, 25, 26, 27, 28, 29, 30, 31, 32, 34, 35, 36, 37, 38, 39, 40, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 73, 74, 75, 76, 77, 78, 79, 81, 82, 83, 84, 85, 86, 87, 88, 89, 91, 92, 93 and 94 demonstrated at least 45% inhibition of human growth hormone receptor expression in this assay and are therefore preferred. More preferred are SEQ ID NOs 30, 44 and 57.

ISIS 272322 (SEQ ID NO: 57) is targeted to exon 10, a region which appears in all growth hormone receptor transcripts. Compounds targeted to exon 10 are therefore preferred embodiments of the invention. Exon 3, reported to be alternatively spliced in the human transcript(s), may also be a preferred target region.

The target regions to which the preferred antisense sequences of Table 2 are complementary are herein referred to as "preferred target segments" and are therefore preferred for targeting by compounds of the present invention. These preferred target segments are shown in Table 3. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

Example 16

Antisense Inhibition of Mouse Growth Hormone Receptor Expression by Chimeric Phosphorothioate Oligonucleotides Having 2'-MOE Wings and a Deoxy Gap In accordance with the present invention, a second series of antisense compounds were designed to target different regions of the mouse growth hormone receptor RNA, using published sequences (GenBank accession number NM_010284.1, incorporated herein as SEQ ID NO: 11, a variant of GenBank accession number AF120480.2 with an alternative splice site from exon 1B:exon 2, incorporated herein as SEQ ID NO: 97, a variant of GenBank accession number AF120480.2 with an alternative splice site at from exon 1C:exon 2, incorporated herein as SEQ ID NO: 98, a variant of GenBank accession number AF120480.2 with an alternative splice site from exon 1D:exon 2, incorporated herein as SEQ ID NO: 99, and a sequence derived from GenBank accession numbers AF120480.2 and AC073753.1, representing a genomic sequence, incorporated herein as SEQ ID NO: 100). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse growth hormone receptor mRNA levels by quantitative real-time PCR as described in other examples herein. Data are averages from three experiments in which b.END cells were treated with the antisense oligonucleotides of the present invention. The positive control for each datapoint is identified in the table by sequence ID number. If present, "N.D." indicates "no data".

TABLE 2

Inhibition of mouse growth hormone receptor mRNA levels by
chimeric phosphorothioate oligonucleotides having 2'-MOE
wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 227443 | 5'UTR | 11 | 5 | tgcttggcagctcgtgggtt | 0 | 101 | 1 |
| 227444 | 5'UTR | 11 | 16 | atggctgcgcctgcttggca | 53 | 102 | 1 |

TABLE 2-continued

Inhibition of mouse growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 227445 | Start Codon | 11 | 221 | tacctgagacctcggagttt | 69 | 103 | 1 |
| 227446 | Start Codon | 11 | 232 | acaaagatccatacctgaga | 87 | 104 | 1 |
| 227447 | Coding | 11 | 300 | gctggtgtagcctcacttcc | 77 | 105 | 1 |
| 227448 | Coding | 11 | 313 | tttgccaagagtagctggtg | 60 | 106 | 1 |
| 227449 | Coding | 11 | 391 | acgacacttggtgaatcgag | 69 | 107 | 1 |
| 227450 | Coding | 11 | 495 | tggctttcccttttagcata | 71 | 108 | 1 |
| 227451 | coding | 11 | 520 | atgagcaattcttgcagctt | 49 | 109 | 1 |
| 227454 | Coding | 11 | 590 | agttgaagtaacagctgttt | 69 | 110 | 1 |
| 227455 | Coding | 11 | 620 | agtagggtatccaaatggag | 43 | 111 | 1 |
| 227456 | Coding | 11 | 717 | gtccagttgaggccaatggg | 97 | 112 | 1 |
| 227457 | Coding | 11 | 812 | gaattatccatcccttcaga | 67 | 113 | 1 |
| 227458 | Coding | 11 | 832 | gtactgaatttcatactcca | 75 | 114 | 1 |
| 227459 | Coding | 11 | 975 | ctgaactcgctgtacttttc | 60 | 115 | 1 |
| 227460 | Coding | 11 | 1041 | aactggatatcttcttcaca | 43 | 116 | 1 |
| 227461 | Coding | 11 | 1084 | tgctactccaaatattccaa | 75 | 117 | 1 |
| 227462 | Coding | 11 | 1115 | gctttgaaaatataactaca | 31 | 118 | 1 |
| 227463 | Coding | 11 | 1137 | atcagcatcttaatcctttg | 39 | 119 | 1 |
| 227465 | Coding | 11 | 1190 | tgagaagatctggatcaatc | 51 | 120 | 1 |
| 227466 | Coding | 11 | 1245 | ttgtagttatcatgaatgcc | 50 | 121 | 1 |
| 227467 | Coding | 11 | 1265 | catcattgtagaagtcgggt | 33 | 122 | 1 |
| 227470 | Coding | 11 | 1388 | ctccaaggataccagctgat | 82 | 123 | 1 |
| 227471 | Coding | 11 | 1530 | aggcacaagagatcagcttc | 52 | 124 | 1 |
| 227472 | Coding | 11 | 1579 | agagccaagggaagcatcat | 42 | 125 | 1 |
| 227473 | Coding | 11 | 1710 | aagtcaatgtttgccagtga | 71 | 126 | 1 |
| 227474 | Coding | 11 | 1730 | tgtcgcttacttgggcataa | 68 | 127 | 1 |
| 227476 | Coding | 11 | 1837 | gtaattttcttggcagggcg | 41 | 128 | 1 |
| 227477 | Coding | 11 | 1850 | cactgttcatgctgtaattt | 61 | 129 | 1 |
| 227478 | Coding | 11 | 1878 | tttttggcatctgactcaca | 68 | 130 | 1 |
| 227479 | Coding | 11 | 1947 | atgtcctcttggttaaagct | 59 | 131 | 1 |
| 227485 | Coding | 11 | 2044 | cgtggtgtagtctgggacag | 45 | 132 | 1 |
| 227486 | Coding | 11 | 2054 | cggtgtgaaccgtggtgtag | 39 | 133 | 1 |
| 227487 | Coding | 11 | 2106 | tcaggcaaaggcaaagcagt | 44 | 134 | 1 |
| 227491 | Stop codon | 11 | 2182 | taggaaaggctactgcatga | 65 | 135 | 1 |

TABLE 2-continued

Inhibition of mouse growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 227492 | 3'UTR | 11 | 2239 | taaaacatagttttggttta | 7 | 136 | 1 |
| 227493 | 3'UTR | 11 | 2253 | tcccaacacagatttaaaac | 51 | 137 | 1 |
| 227494 | 3'UTR | 11 | 2517 | caaaagccacctgattgttt | 56 | 138 | 1 |
| 227495 | 3'UTR | 11 | 2527 | tcctgaactgcaaaagccac | 47 | 139 | 1 |
| 227496 | 3'UTR | 11 | 2537 | gcattcaatttcctgaactg | 51 | 140 | 1 |
| 227497 | 3'UTR | 11 | 2637 | taaatgttttgcatatccaa | 77 | 141 | 1 |
| 227498 | 3'UTR | 11 | 2824 | ttgtaaaaatctaacttgtt | 49 | 142 | 1 |
| 227503 | exon:exon junction | 97 | 197 | tacctgagaccccagttcat | 24 | 143 | 1 |
| 227504 | exon:exon junction | 98 | 23 | tacctgagaccccgcgcagc | 34 | 144 | 1 |
| 227505 | exon:exon junction | 99 | 61 | tacctgagacccacaagcgg | 39 | 145 | 1 |
| 227506 | exon:intron junction | 100 | 4352 | cctccagtacctcggagttt | 69 | 146 | 1 |
| 227507 | intron:exon junction | 100 | 4865 | gtccttgctccaggttagca | 89 | 147 | 1 |
| 227508 | exon:intron junction | 100 | 5071 | ttccactcaccccagttcat | 51 | 148 | 1 |
| 227509 | intron:exon junction | 100 | 5153 | gcagttctatcagaactttg | 82 | 149 | 1 |
| 227510 | intron | 100 | 5196 | ctccagacgtgacccgactc | 64 | 150 | 1 |
| 227511 | exon:intron junction | 100 | 5264 | ccacgcacccacaagcggat | 71 | 151 | 1 |
| 227512 | intron | 100 | 6350 | taacctatggtgactatgtc | 36 | 152 | 1 |
| 227513 | intron:exon junction | 100 | 7123 | tacctgagacctgcaagaca | 40 | 153 | 1 |
| 227514 | intron | 100 | 9753 | atgctcacgtcagctattgg | 43 | 154 | 1 |
| 227515 | exon:intron junction | 100 | 13932 | aaattcttacttgtccccag | 37 | 155 | 1 |
| 227516 | intron:exon junction | 100 | 17200 | ttggctttccctggaggttc | 57 | 156 | 1 |
| 227517 | exon:intron junction | 100 | 17224 | cttcactaaccttgcagctt | 63 | 157 | |
| 227518 | exon:intron junction | 100 | 24259 | cacggcttacctatttcgtc | 6 | 158 | |

TABLE 2-continued

Inhibition of mouse growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 227519 | exon: intron junction | 100 | 37843 | tcacacctacctttgctgct | 44 | 159 | |
| 227520 | intron: exon junction | 100 | 40862 | catcttaatccttggaaaca | 42 | 160 | 2 |

As shown in Table 2, SEQ ID NOs 102, 103, 104, 105, 106, 107, 108, 110, 112, 113, 114, 115, 117, 120, 121, 123, 124, 126, 127, 129, 130, 131, 135, 137, 138, 140, 141, 146, 147, 148, 149, 150, 151, 156 and 157 demonstrated at least 50% inhibition of mouse growth hormone receptor expression in this experiment and are therefore preferred. More preferred are SEQ ID NOs 104, 147, and 149.

ISIS 227446, 227507 and 227509 (SEQ ID NO: 104, 147 and 149) were subjected to dose-response studies. All three compounds showed good dose responses with IC50s of approximately 25 nM, 12.5 nM and 12.5 nM, respectively.

The target regions to which the preferred antisense sequences of Table 2 are complementary are herein referred to as "preferred target segments" and are therefore preferred for targeting by compounds of the present invention. These preferred target segments are shown in Table 3. The sequences represent the reverse complement of the preferred antisense compounds shown in Table 2. "Target site" indicates the first (5'-most) nucleotide number on the particular target nucleic acid to which the oligonucleotide binds. Also shown in Table 3 is the species in which each of the preferred target segments was found.

TABLE 3

Sequence and position of preferred target segments identified in growth hormone receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 144070 | 4 | 332 | gaatggaaagaatgccctga | 19 | H. sapeins | 161 |
| 144071 | 4 | 337 | gaaagaatgccctgattatg | 20 | H. sapeins | 162 |
| 144082 | 4 | 947 | ccagttccaaagattaaagg | 21 | H. sapeins | 163 |
| 144086 | 4 | 1079 | attgagctagatattgatga | 22 | H. sapeins | 164 |
| 144087 | 4 | 1124 | gacacagacagacttctaag | 23 | H. sapeins | 165 |
| 144093 | 4 | 1514 | agcgacattacaccagcagg | 24 | H. sapeins | 166 |
| 144098 | 4 | 1724 | aaccaagaggacatttacat | 25 | H. sapeins | 167 |
| 144099 | 4 | 1729 | agaggacatttacatcacca | 26 | H. sapeins | 168 |
| 144100 | 4 | 1734 | acatttacatcaccacagaa | 27 | H. sapeins | 169 |
| 144101 | 4 | 1739 | tacatcaccacagaaagcct | 28 | H. sapeins | 170 |
| 144102 | 4 | 1744 | caccacagaaagccttacca | 29 | H. sapeins | 171 |
| 144106 | 4 | 1922 | tatgtgagcacagaccaact | 30 | H. sapeins | 172 |
| 144107 | 4 | 1927 | gagcacagaccaactgaaca | 31 | H. sapeins | 173 |
| 144108 | 4 | 1936 | ccaactgaacaaaatcatgc | 32 | H. sapeins | 174 |
| 144118 | 4 | 4043 | tctgctactttgctgctatg | 34 | H. sapeins | 175 |
| 144119 | 4 | 4183 | tttctatagccaaaaatagc | 35 | H. sapeins | 176 |
| 144120 | 4 | 4197 | aatagctaaatacctcaatc | 36 | H. sapeins | 177 |
| 188518 | 4 | 31 | aggtcctacaggtatggatc | 37 | H. sapeins | 178 |

TABLE 3-continued

Sequence and position of preferred target segments identified in growth hormone receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 188519 | 4 | 36 | ctacaggtatggatctctgg | 38 | H. sapeins | 179 |
| 188520 | 4 | 115 | cacagcagctatccttagca | 39 | H. sapeins | 180 |
| 188521 | 4 | 160 | taatccaggcctaaagacaa | 40 | H. sapeins | 181 |
| 188523 | 4 | 185 | tctaaggagcctaaattcac | 42 | H. sapeins | 182 |
| 188524 | 4 | 274 | gaacctaggacccatacagc | 43 | H. sapeins | 183 |
| 188525 | 4 | 362 | gctggggaaaacagctgtta | 44 | H. sapeins | 184 |
| 188526 | 4 | 439 | tggtggtacagtggatgaaa | 45 | H. sapeins | 185 |
| 188527 | 4 | 468 | ctgttgatgaaatagtgcaa | 46 | H. sapeins | 186 |
| 188528 | 4 | 480 | tagtgcaaccagatccaccc | 47 | H. sapeins | 187 |
| 188529 | 4 | 564 | gatgggaagcaccacgcaat | 48 | H. sapeins | 188 |
| 188530 | 4 | 652 | atggaaaatgatggaccta | 49 | H. sapeins | 189 |
| 188531 | 4 | 684 | cagttccagtgtactcattg | 50 | H. sapeins | 190 |
| 188532 | 4 | 752 | tctggaaattatggcgagtt | 51 | H. sapeins | 191 |
| 188533 | 4 | 857 | atctttggaatatttgggct | 52 | H. sapeins | 192 |
| 188534 | 4 | 913 | gcaaaggattaaaatgctga | 53 | H. sapeins | 193 |
| 188535 | 4 | 979 | tctcctcaaggaaggaaaat | 54 | H. sapeins | 194 |
| 188536 | 4 | 1000 | agaggaggtgaacacaatct | 55 | H. sapeins | 195 |
| 188537 | 4 | 1053 | acagtgatgactcttgggtt | 56 | H. sapeins | 196 |
| 188538 | 4 | 1084 | gctagatattgatgagccag | 57 | H. sapeins | 197 |
| 188539 | 4 | 1110 | agactgaggaatcagacaca | 58 | H. sapeins | 198 |
| 188540 | 4 | 1236 | atttcaatgccaatgacata | 59 | H. sapeins | 199 |
| 188541 | 4 | 1302 | aagcagatctcttatgcctt | 60 | H. sapeins | 200 |
| 188542 | 4 | 1420 | tcctactgaaggagctgagt | 61 | H. sapeins | 201 |
| 188543 | 4 | 1560 | agaataaggcagggatgtcc | 62 | H. sapeins | 202 |
| 188544 | 4 | 1623 | acttccttatggacaatgcc | 63 | H. sapeins | 203 |
| 188545 | 4 | 1651 | tgaggcagatgccaaaaagt | 64 | H. sapeins | 204 |
| 188546 | 4 | 1656 | cagatgccaaaaagtgcatc | 65 | H. sapeins | 205 |
| 188547 | 4 | 1861 | cctcatactcaatgcgactg | 66 | H. sapeins | 206 |
| 188548 | 4 | 1884 | tgcccttgcctgacaaagag | 67 | H. sapeins | 207 |
| 188549 | 4 | 1913 | tcatgtggctatgtgagcac | 68 | H. sapeins | 208 |
| 188550 | 4 | 1949 | atcatgccttagccttctt | 69 | H. sapeins | 209 |
| 188551 | 4 | 1973 | ttcccaagagctacgtattt | 70 | H. sapeins | 210 |
| 188552 | 4 | 2196 | ctgtttagtagcagtgattg | 71 | H. sapeins | 211 |
| 188554 | 4 | 2337 | ttgaatgcaaaccatagcac | 73 | H. sapeins | 212 |
| 188555 | 4 | 2454 | atagtttggatatgtaaaac | 74 | H. sapeins | 213 |
| 188556 | 4 | 2853 | tcaccaaatcttggttgatg | 75 | H. sapeins | 214 |

TABLE 3-continued

Sequence and position of preferred target segments identified in growth hormone receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 188557 | 4 | 2988 | gagataagatctatagcctc | 76 | H. sapeins | 215 |
| 188558 | 4 | 3271 | agaaactttctttctcacta | 77 | H. sapeins | 216 |
| 188559 | 4 | 3765 | acatcattcttgagagcatt | 78 | H. sapeins | 217 |
| 188560 | 4 | 3980 | gaaaagctagaattgagtgt | 79 | H. sapeins | 218 |
| 188562 | 4 | 4057 | gctatggttttctccaagag | 81 | H. sapeins | 219 |
| 188563 | 4 | 4097 | taaagtatcatcagtgtaga | 82 | H. sapeins | 220 |
| 188564 | 4 | 4120 | taattcaattcaaagctgtg | 83 | H. sapeins | 221 |
| 188565 | 4 | 4133 | agctgtgtgtttggaagact | 84 | H. sapeins | 222 |
| 188566 | 4 | 4156 | ttactatttcacaacagcct | 85 | H. sapeins | 223 |
| 188567 | 4 | 4170 | cagcctgacaacatttctat | 86 | H. sapeins | 224 |
| 188568 | 4 | 4218 | gtctcagaatgtcattttgg | 87 | H. sapeins | 225 |
| 188569 | 4 | 4245 | gtggccacataagccattat | 88 | H. sapeins | 226 |
| 188570 | 18 | 2571 | tcaatcagggtcacataact | 89 | H. sapeins | 227 |
| 188572 | 18 | 8405 | tttgaacctccagcctccat | 91 | H. sapeins | 228 |
| 188573 | 18 | 22712 | gtcttgaaagatggaccta | 92 | H. sapeins | 229 |
| 188574 | 18 | 25543 | gtttagattctatctggaga | 93 | H. sapeins | 230 |
| 188575 | 18 | 29755 | aaagtaccagaatatttgga | 94 | H. sapeins | 231 |
| 144062 | 11 | 16 | tgccaagcaggcgcagccat | 102 | M. musculus | 232 |
| 144063 | 11 | 221 | aaactccgaggtctcaggta | 103 | M. musculus | 233 |
| 144064 | 11 | 232 | tctcaggtatggatctttgt | 104 | M. musculus | 234 |
| 144065 | 11 | 300 | ggaagtgaggctacaccagc | 105 | M. musculus | 235 |
| 144066 | 11 | 313 | caccagctactcttggcaaa | 106 | M. musculus | 236 |
| 144067 | 11 | 391 | ctcgattcaccaagtgtcgt | 107 | M. musculus | 237 |
| 144068 | 11 | 495 | tatgctaaaagggaaagcca | 108 | M. musculus | 238 |
| 144072 | 11 | 590 | aaacagctgttacttcaact | 110 | M. musculus | 239 |
| 144074 | 11 | 717 | cccattggcctcaactggac | 112 | M. musculus | 240 |
| 144075 | 11 | 812 | tctgaagggatggataattc | 113 | M. musculus | 241 |
| 144076 | 11 | 832 | tggagtatgaaattcagtac | 114 | M. musculus | 242 |
| 144077 | 11 | 975 | gaaaagtacagcgagttcag | 115 | M. musculus | 243 |
| 144079 | 11 | 1084 | ttggaatatttggagtagca | 117 | M. musculus | 244 |
| 144083 | 11 | 1190 | gattgatccagatcttctca | 120 | M. musculus | 245 |
| 144084 | 11 | 1245 | ggcattcatgataactacaa | 121 | M. musculus | 246 |
| 144088 | 11 | 1388 | atcagctggtatccttggag | 123 | M. musculus | 247 |
| 144089 | 11 | 1530 | gaagctgatctcttgtgcct | 124 | M. musculus | 248 |
| 144091 | 11 | 1710 | tcactggcaaacattgactt | 126 | M. musculus | 249 |
| 144092 | 11 | 1730 | ttatgcccaagtaagcgaca | 127 | M. musculus | 250 |

TABLE 3-continued

Sequence and position of preferred target segments identified in growth hormone receptor.

| SITE ID | TARGET SEQ ID NO | TARGET SITE | SEQUENCE | REV COMP OF SEQ ID | ACTIVE IN | SEQ ID NO |
|---|---|---|---|---|---|---|
| 144095 | 11 | 1850 | aaattacagcatgaacagtg | 129 | M. musculus | 251 |
| 144096 | 11 | 1878 | tgtgagtcagatgccaaaaa | 130 | M. musculus | 252 |
| 144097 | 11 | 1947 | agctttaaccaagaggacat | 131 | M. musculus | 253 |
| 144109 | 11 | 2182 | tcatgcagtagcctttccta | 135 | M. musculus | 254 |
| 144111 | 11 | 2253 | gttttaaatctgtgttggga | 137 | M. musculus | 255 |
| 144112 | 11 | 2517 | aaacaatcaggtggcttttg | 138 | M. musculus | 256 |
| 144114 | 11 | 2537 | cagttcaggaaattgaatgc | 140 | M. musculus | 257 |
| 144115 | 11 | 2637 | ttggatatgcaaaacattta | 141 | M. musculus | 258 |
| 144124 | 100 | 4352 | aaactccgaggtactggagg | 146 | M. musculus | 259 |
| 144125 | 100 | 4865 | tgctaacctggagcaaggac | 147 | M. musculus | 260 |
| 144126 | 100 | 5071 | atgaactggggtgagtggaa | 148 | M. musculus | 261 |
| 144127 | 100 | 5153 | caaagttctgatagaactgc | 149 | M. musculus | 262 |
| 144128 | 100 | 5196 | gagtcgggtcacgtctggag | 150 | M. musculus | 263 |
| 144129 | 100 | 5264 | atccgcttgtgggtgcgtgg | 151 | M. musculus | 264 |
| 144134 | 100 | 17200 | gaacctccagggaaagccaa | 156 | M. musculus | 265 |
| 144135 | 100 | 17224 | aagctgcaaggttagtgaag | 157 | M. musculus | 266 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of growth hormone receptor.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 17

Western Blot Analysis of Growth Hormone Receptor Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to growth hormone receptor is used, with a radiolabeled or fluorescently labeled secondary antibody directed against the primary antibody species. Bands are visualized using a PHOSPHORIMAGER™ (Molecular Dynamics, Sunnyvale Calif.).

Example 18

Reduction of Serum IGF-I in Animals After Treatment with Antisense to Growth Hormone Receptor—1 Week Pilot Study Forty male Balb/C(a) mice weighing 9 to 10 g were placed into cages, 4 animals per cage, and allowed to assimilate into their environment with new littermates ~1 week prior (Day −7) to the commencement of 1 week study. Mice of this age would be at their maximum growth rate. Their body weights were measured and recorded every second day during this period. When mice weighed 11 g (day −2), a blood sample was collected under anesthesia as described below, and a serum IGF-I assay was performed to determine pre-treatment values and to aid in the assigning of mice to treatment groups in order to reduce animal variability. To obtain the blood sample, the animals were anaesthetized with pentobarbital (50 mg/kg i.p.) and non-fasting blood samples collected exactly 5 minutes later from the retrobulbar plexus through heparinized capillary tubes under light ether anesthesia. The 40 animals were placed into five groups with each group having a similar weight average and similar IGF-I average concentration for the trial.

Animals (n=8/group) were designated to the following five treatment groups:

Control—saline (once every 2 days)

ASO (Antisense to growth hormone receptor)—ISIS 227446 (SEQ ID NO: 104) (3 and 30 mg/kg once every 2 days)

Mismatch (negative control oligonucleotide)—ISIS 261303 (SEQ ID NO: 267, 8-base mismatch to ISIS 227446) (30 mg/kg once every 2 days)

Octreotide—(25 µg/kg/twice per day)

Saline, antisense, mismatch control and octreotide samples were prepared, and coded for blinding. Animals were given a subcutaneous dose of saline every second day, and mismatch control or antisense with administration on days 0, 2, 4, 6. Animals were given twice daily doses of 25 µg octreotide. Animals were housed 4 per cage, for the duration of one week. They had access to a pre-determined quantity of standard mouse food and water at all times throughout the experiment. They were housed in a quiet, temperature- and humidity-maintained environment for the entirety of the study. At day 0 and before treatment on each day or second day, the animals had their body weight and food intake measured, enabling the correct dose of agent to be administered. The animals were monitored closely for any changes in fur, skin, eye, locomotion or other changes in behavior. No problems were observed. Every second day from day −7 to day 7 body weight and food intake were measured.

On day 7, one day after the last dose of antisense, and/or after the last octreotide dose, the animals were anaesthetized with pentobarbital (50 mg/kg i.p.) and non-fasting blood samples collected exactly 5 minutes later from the retrobulbar plexus through heparinized capillary tubes under light ether anesthesia (as on day −7 and 0).

At day −2 and day 7, serum IGP-I measurement was done by radioimmunoassay. The results are shown in Table 4. Serum IGF-I level is the most widely used measure of growth hormone biological activity in human therapy. It is used to measure the efficacy of growth hormone antagonist treatments like Trovert, which block cells' responsiveness to excess growth hormone, and dopamine agonists and octreotide somatostatin antagonist drugs that block growth hormone secretion from the pituitary.

TABLE 4

Effect of antisense inhibitor of growth hormone receptor on serum insulin-like growth factor-I levels

|  | IGF-I (ng/ml) Day −2 | IGF-I (ng/ml) Day 7 | % IGF-I reduction* |
|---|---|---|---|
| Saline Control | 217.09 ± 42.61 | 102.64 ± 31.64 | 0 |
| Octreotide | 199.72 ± 44.47 | 114.34 ± 41.36 | — |
| ASO 3 mg/kg | 216.23 ± 78.14 | 129.63 ± 33.76 | — |
| ASO 30 mg/kg | 181.84 ± 71.32 | 56.95 ± 10.34 | 44.51 |
| Mismatch 30 mg/kg | 184.87 ± 55.6 | 81.1 ± 19.16 | 20.98 |

*Percent reduction in serum IGF-I at day 7 compared to saline control at day 7.

As shown in Table 4, the growth hormone receptor antisense compound, ISIS 227446 (SEQ ID NO: 104, dosed subcutaneously at 30 mg/kg every second day for one week, produced a statistically significant and specific reduction of serum IGF-I to 55% of the control (saline) group. By t-test the antisense 30 mg/kg was significantly different from the saline control (p<0.005) and the mismatch control (p<0.01). The mismatch control was not statistically different from the saline control (p>0.05). There was no effect at 3 mg/kg. The 45% reduction in serum IGF-I levels in our study using 30 mg/kg antisense every second day is comparable to that achieved using 10 mg/kg daily Trovert (Van Neck et al., *J. Endocrinol.*, 2000, 167, 295-303).

The negative control 8-nucleotide mismatch oligonucleotide ISIS 261303 (SEQ ID NO: 267), reduced serum IGF-I by 21% compared to the control saline group, however, this reduction was not statistically significant (with p >0.05). Octreotide, 2 doses per day at 25 µg each had no effect on serum IGF-I levels at day 7. The non-effect obtained with octreotide is consistent with data reported by Groenbaek et al *J. Endocrinol.*, 2002, 172, 637-643) using this dose and twice this dose at day 7 in diabetic animals. In diabetic animals two 50 kg doses of octreotide per day for two weeks are required to reduce sIGF-I levels.

Thus an antisense inhibitor of growth hormone receptor has now been demonstrated to specifically reduce serum insulin-like growth factor-I levels by 45% compared to control. Reduction of serum insulin-like growth factor-I by similar levels using octreotide or Trovert, are clinically relevant in the treatment of diseases including acromegaly, gigantism, age-related macular degeneration, diabetic retinopathy, diabetic nephropathy, diabetes, and growth hormone and IGF-I-dependent tumors as outlined supra. Thus antisense therapy is believed to be therapeutically useful for treatment of conditions associated with the growth hormone/insulin-like growth factor-I axis.

The serum remaining following the insulin-like growth factor-1 assay was isolated and stored at −80° C. The whole liver was removed rapidly for weighing and snap-frozen in labelled aluminum parcels by submersion in liquid-nitrogen. Kidney and spleen were also snap frozen in liquid nitrogen and stored at −80° C. in the freezer. The carcass was weighed and then placed into a sealable plastic bag, snap-frozen on dry ice and kept at −80° C.

The decline in serum insulin-like growth factor-I with 30 mg/kg of antisense was not sufficient to influence body weight or organ weights over this period. This confirms published results of others. Van Neck et al., *J Endocrinol.*, 2000, 167, 295-303. Looking at the study overall, body length increase during the study was in the range 7.5-10%. Tail length increases were in proportion to overall length increases. Food intake did not vary significantly between treatment groups. Growth (body length and weight) were unaffected by any treatment. Weight was measured in two ways: weight trend (live animal), and final carcass weight. Absolute liver weights were unchanged except for a slight increase in liver weight (g/total body weight) for the octreotide group. Weights of other organs were unaffected. These observations were similar to those reported by van Neck et al. with Trovert except that liver weight was unaffected by Trovert, as also observed with growth hormone receptor antisense.

Growth hormone receptor mRNA levels in tissue samples from our current study are assayed from liver and kidney to test for an RNase H-based antisense mechanism of action. Growth hormone receptor protein levels by Western or binding assays in tissue samples from our current study are assayed from liver and/or kidney to test for additional and/or alternative antisense mechanisms of action. Liver contributes to 75% of serum insulin-like growth factor-I levels as shown in growth hormone receptor knockout animals of Sjogren et al., *Proc. Natl. Acad. Sci. USA*, 1999, 96, 7088-7092. Sample analysis of the liver and kidney insulin-like growth factor-I by Western and Northern blot total RNA analysis or quantitative PCR is also done as would be understood by those skilled in the art.

Example 19

Reduction of Growth Hormone Receptor Activity in Animals After Treatment with Antisense to Growth Hormone Receptor Specific binding assays were carried out with liver tissue using iodinated human growth hormone [$^{125}$I] hGH.

Microsomal membrane preparations were obtained as follows. 400 mg of tissue powder was homogenized in cold homogenizing buffer (50 mM Tris/HCl, 250 mM sucrose, pH 7.4). This was centrifuged at 2000 rpm for 10 min at 3° C. and the supernatant was saved. This was centrifuged again at 15,000 rpm for 20 min. Pellets were resuspended in 0.5 ml of RRA buffer with inhibitor (50 mM Tris, 20 mM MgCl$_2$, pH 7.4). Microsomal preparation samples were stored at −80° C. until the specific binding assay.

The [$^{125}$I] hGH specific binding assay was done as follows. Four glass tubes were set up for each sample, two for (−), two for (+). Different sample and solutions were added in each tube as follows (i) 0.2 ml RRA buffer (50 Tris, 20 mM MgCl$_2$, 0.1% BSA, pH 7.4); (ii) 0.1 ml membrane (1/2 or 1/4 dilution); (iii) 0.1 ml bGH (10 µg/ml) for the(+) tube or 0.1 ml RRA buffer for the(−) tube; and (iv) 0.1 ml [$^{125}$I]-hGH tracer.

Samples were incubated at 4° C. with shaking overnight. The reaction was stopped with 2.5 ml of cold RRA, and the sample centrifuged at 2800 rpm for 25 min at 4° C. Supernatant was aspirated and pellets counted using the γ-counter. The specific binding capacity was calculated as: CPM(−)−CPM(+). Protein content of the microsomal samples was determined by the BCA protein assay.

TABLE 5

Effect of antisense inhibitor on growth hormone receptor growth hormone binding activity

|  | Specific binding/mg protein (cpm) ½ dilution | Specific binding/mg protein (cpm) ¼ dilution |
| --- | --- | --- |
| Saline Control | 5647 ± 746 | 9071 ± 2371 |
| ASO 30 mg/kg | 4205 ± 534 (26% reduction compared to saline) | 5546 ± 789 (39% reduction compared to saline) |
| Mismatch 30 mg/kg | 7090 ± 1877 | 8431 ± 2663 |

As shown in Table 5, the growth hormone receptor antisense compound, ISIS 227446 (SEQ ID NO: 104, dosed subcutaneously at 30 mg/kg every second day for one week, produced a statistically significant (p<0.05) and specific reduction of growth hormone receptor levels (measured by growth hormone binding activity) to 61% of control (saline) group. The negative control 8-nucleotide mismatch oligonucleotide ISIS 261303 (SEQ ID NO: 267) had no effect compared to the control saline group. The antisense inhibitor of growth hormone receptor produced a statistically significant (p<0.01) and specific reduction of growth hormone receptor levels to 59% of the control (mismatch) group in the 1/2 dilution experiment.

The specific reduction of growth hormone receptor levels was significantly (by t-test) different from both the saline control and the mismatch control at both dilutions (p<0.05).

These growth hormone receptor level measurements following antisense treatment are consistent with the 45% reduction in serum insulin-like growth factor-I levels in our study using 30 mg/kg antisense every second day relative to control (saline).

Example 20

Reduction of Growth Hormone Receptor mRNA Levels and Serum IGF-I in Animals After Treatment with Antisense to Growth Hormone Receptor—Additional 1 Week Study Male Balb/C(a) mice were prepared and grouped for analysis as in Example 18 above.

Animals (n=10/group) were designated to the following treatment groups:

Control—saline (once every 2 days)

ASO (Antisense to growth hormone receptor)—ISIS 227446 (SEQ ID NO: 104) (30 and 50 mg/kg once every 2 days)

Unrelated negative control oligonucleotide—ISIS 260120 (TTACCGTATGGTTCCTCACT; SEQ ID NO: 268, (50 mg/kg once every 2 days)

Animals were treated and serum IGF-I levels were measured as in Example 18 above. Briefly, for the one-week study, mice were given a subcutaneous dose of saline every second day, and mismatch control or antisense with administration on days 0, 2, 4, 6. On day 7, the animals were anaesthetized with pentobarbital and non-fasting blood samples collected exactly 5 minutes later from the retrobulbar plexus through heparinized capillary tubes under light ether anesthesia. Serum IGF-I measurement was done by radioimmunoassay at day 7.

In the one-week study, the growth hormone receptor antisense inhibitor ISIS 227446 reduced serum IGF-I by 33% at the 50 mg/kg dose, relative to saline control (p<0.001), and by 20% relative to the unrelated control (p<0.068). The unrelated control at the 50 mg/kg dose reduced serum IGF-I by 17% compared to saline (p>0.05).

Growth hormone receptor mRNA levels in liver tissue samples from treated and untreated mice in this one-week study were assayed. The growth hormone receptor antisense inhibitor ISIS 227446 reduced growth hormone receptor mRNA levels in liver after the one-week study by 72% at the 50 mg/kg dose, relative to saline control (p <0.0001). The 30 mg/kg dose of ISIS 227446 yielded a 50% decrease in growth hormone receptor mRNA (p<0.0001). The unrelated control oligonucleotide ISIS 260120, at 50 mg/kg, reduced growth hormone receptor mRNA levels by approximately 15% (p>0.05).

Example 21

Reduction of Growth Hormone Receptor mRNA Levels and Serum IGF-I in Animals After Treatment with Antisense to Growth Hormone Receptor—2 Week Study A two-week study was done in similar fashion to the one-week study in Example 18, this time using ISIS 227446 at doses of 3, 5, 10, 20 and 30 mg/kg. The mismatch control was given at the same doses. Mice were treated with antisense compound or saline every other day for 14 days.

Table 5 shows the serum IGF-I levels in mice treated for 14 days. P-values were determined by t-test.

TABLE 5

Two week mouse study- serum IGF-I levels after treatment
with antisense inhibitor of growth hormone receptor

| Dose of ISIS 227446 (mg/kg) | Day 14 serum IGF-I ng/ml | % decrease relative to 3 mg/kg ISIS 227446 | p-value |
|---|---|---|---|
| 30 | 126 | 41 | 0.0002 |
| 20 | 122 | 43 | 0.0002 |
| 10 | 130 | 39 | 0.0002 |
| 5 | 194 | 9 | 0.3261 |
| 3 | 214 | 0 | — |

The reduction in serum IGF-I at 14 days was dependent on dose with 39-43% decrease in levels achieved at >10 mg/kg compared to 3 mg/kg. The 3 mg/kg dose of ISIS 227446 had no effect on serum IGF-I levels and was equivalent to saline (untreated) control (shown in separate experiment).

Mismatch controls gave lesser reductions in serum IGF-I levels. These results are shown in Table 6. The effect at 30 mg/kg observed with the mismatch oligonucleotide at 2 weeks was not observed with an unrelated negative control oligonucleotide (ISIS 260120; SEQ ID NO: 268).

TABLE 6

Two week mouse study- serum IGF-I levels after
treatment with mismatch control ISIS 261303

| Dose of ISIS 261303 (mg/kg) | Day 14 serum IGF-I ng/ml | % decrease relative to 3 mg/kg ISIS 261303 | p-value |
|---|---|---|---|
| 30 | 130 | 29 | 0.0094 |
| 20 | 164 | 11 | 0.2496 |
| 10 | 174 | 5 | 0.6160 |
| 5 | 186 | 0 | 0.9359 |
| 3 | 184 | 0 | — |

Growth hormone receptor mRNA levels in liver tissue samples from treated and untreated mice in this two-week study were assayed. The growth hormone receptor antisense inhibitor ISIS 227446 reduced growth hormone receptor mRNA levels in liver after the two-week study by 50% at the 20 mg/kg dose relative to saline control (p<0.001). The 30 mg/kg dose of ISIS 227446 yielded a 53% decrease in growth hormone receptor mRNA (p<0.0001). The mismatch control oligonucleotide ISIS 261303 (SEQ ID NO: 267), at 30 mg/kg, reduced growth hormone receptor mRNA levels by approximately 3%.

Example 22

Effect of Antisense Inhibition of Growth Hormone Receptor on Retinopathy

Retinopathy of prematurity is a neovascularization disorder that can lead to blindness in very low birth weight infants. The retinopathy (abnormal blood vessel formation) is initiated by relatively high oxygen levels such as are found in infant incubators, for example. A mouse model of retinopathy (abnormal blood vessel formation in the retina) is used to study the effects of drugs on the extent of neovascularization.

Seven-day-old mice are placed in an infant incubator with their nursing mother in 75% oxygen from postnatal day 7 to day 12 to produce oxygen-induced retinopathy as described in the literature. Smith et al., 1994, *Invest Ophthalmol Vis Sci* 35, 101-111; Robinson et al., *Proc Natl Acad Sci USA.*, May 14, 1996; 93, 4851-6. Oxygen concentration is measured at least daily while the animals are in oxygen. On postnatal day 12, the animals are returned to room air. Animals are sacrificed on postnatal day 17 when maximal neovascularization is observed.

Mice are dosed with antisense oligonucleotide at postnatal days 12, 13, 14, 15, and 16 or days 7, 8, 9, 11, 13, 15 and 17. Oligonucleotide is administered intraperitoneally at concentrations of 5, 10, 20 and 30 mg/kg. The mismatch control ISIS 261303 and/or the unrelated negative antisense control ISIS 260120 are also given.

Example 23

Additional Models

Studies using antisense inhibitors of growth hormone receptor are also done in the following pathology animal models and in humans as would be understood by those skilled in the art: diabetic nephropathy type I and type II models, cancer models, arthritis models and chemotherapy induced diarrhea models.

---

What is claimed is:

1. A compound comprising an oligonucleotide consisting of 12 to 50 linked nucleosides, wherein said oligonucleotide is fully complementary to the nucleotide sequence within the range of nucleotides 290 to 369 of SEQ ID NO: 4, and wherein said oligonucleotide comprises at least one modified internucleoside linkage, modified sugar moiety, or modified nucleobase.

2. The compound of claim 1, wherein said oligonucleotide consists of 13 to 50 linked nucleosides.

3. The compound of claim 1, wherein said oligonucleotide consists of 15 to 30 linked nucleosides.

4. A composition comprising the compound according to claim 1 and a pharmaceutically acceptable carrier.

5. The compound of claim 1, wherein said oligonucleotide is fully complementary with the range of nucleotides 332 to 356 of SEQ ID NO: 4.

6. The compound of claim 1, consisting of a single-stranded oligonucleotide.

7. The compound of claim 6, wherein at least one internucleoside linkage is a modified internucleoside linkage.

8. The compound of claim 7, wherein each internucleoside linkage is a phosphorothioate internucleoside linkage.

9. The compound of claim 6, wherein at least one nucleoside comprises a modified sugar.

10. The compound of claim 9, wherein at least one modified sugar is a bicyclic sugar.

11. The compound of claim 9, wherein the modified sugar is selected from the group consisting of a 2'-O-(2-methoxyethyl), and a 4'-(CH$_2$)$_n$—O-2' bridge, wherein n is 1 or 2.

12. The compound of claim 6, wherein at least one nucleoside comprises a modified nucleobase.

13. The compound of claim 12, wherein the modified nucleobase is a 5-methylcytosine.

14. The compound of claim 6, wherein the oligonucleotide consists of 20 linked nucleosides.

15. The compound of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

16. The compound of claim 15, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar; wherein each cytosine in said oligonucleotide is a 5-methylcytosine, and wherein each internucleoside linkage of said oligonucleotide is a phosphorothioate linkage.

17. The compound of claim 16, wherein the oligonucleotide consists of 20 linked nucleosides.

18. A compound comprising an oligonucleotide consisting of 15 to 30 linked nucleosides, wherein said oligonucleotide has at least 90% sequence complementarity within the range of nucleotides 290 to 369 of SEQ ID NO: 4 as measured over the entirety of said oligonucleotide, and wherein said oligonucleotide comprises at least one modified internucleoside linkage, modified sugar moiety, or modified nucleobase.

19. The compound of claim 18, wherein said oligonucleotide has 100% sequence complementarity within the range of nucleotides 290 to 369 of SEQ ID NO: 4 as measured over the entirety of said oligonucleotide.

20. A composition comprising the compound according to claim 18 and a pharmaceutically acceptable carrier.

21. The compound of claim 18, consisting of a single-stranded oligonucleotide.

22. The compound of claim 21, wherein at least one internucleoside linkage is a modified internucleoside linkage.

23. The compound of claim 22, wherein each internucleoside linkage is a phosphorothioate internucleoside linkage.

24. The compound of claim 21, wherein at least one nucleoside comprises a modified sugar.

25. The compound of claim 24, wherein at least one modified sugar is a bicyclic sugar.

26. The compound of claim 24, wherein the modified sugar is selected from the group consisting of a 2'-O-(2-methoxyethyl), and a 4'-(CH$_2$)$_n$—O-2' bridge, wherein n is 1 or 2.

27. The compound of claim 21, wherein at least one nucleoside comprises a modified nucleobase.

28. The compound of claim 27, wherein the modified nucleobase is a 5-methylcytosine.

29. The compound of claim 21, wherein the oligonucleotide consists of 20 linked nucleosides.

30. The compound of claim 18, wherein said oligonucleotide has at least 95% sequence complementarity within the range of nucleotides 290 to 369 of SEQ ID NO: 4 as measured over the entirety of said oligonucleotide.

31. The compound of claim 18, wherein the modified oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

32. The compound of claim 31, wherein the modified oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar; wherein each cytosine in said oligonucleotide is a 5-methylcytosine, and wherein each internucleoside linkage of said oligonucleotide is a phosphorothioate linkage.

33. The compound of claim 32, wherein the oligonucleotide consists of 20 linked nucleosides.

34. The compound of claim 18, wherein said oligonucleotide has at least 90% sequence complementarity within the range of nucleotides 332 to 356 of SEQ ID NO: 4 as measured over the entirety of said oligonucleotide.

35. The compound of claim 18, wherein said oligonucleotide has at least 95% sequence complementarity within the range of nucleotides 332 to 356 of SEQ ID NO: 4 as measured over the entirety of said oligonucleotide.

* * * * *

SEQUENCE LISTING

<160> NUMBER OF SEQ ID NOS: 268

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                    20

<210> SEQ ID NO 2
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 2
gtgcgcgcga gcccgaaatc                    20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                    20

<210> SEQ ID NO 4
<211> LENGTH: 4414
<212> TYPE: DNA
<213> ORGANISM: H. sapiens
<220> FEATURE:
<220> FEATURE:
<221> NAME/KEY: CDS
<222> LOCATION: (44)...(1960)

<400> SEQUENCE: 4

```
ccgcgctctc tgatcagagg cgaagctcgg aggtcctaca ggt atg gat ctc tgg        55
                                              Met Asp Leu Trp
                                                1 cag ctg ctg ttg acc ttg gca ctg gca gga tca agt gat gct ttt tct       103
Gln Leu Leu Leu Thr Leu Ala Leu Ala Gly Ser Ser Asp Ala Phe Ser
  5                  10                  15                  20 gga agt gag gcc aca gca gct atc ctt agc aga gca ccc tgg agt ctg       151
Gly Ser Glu Ala Thr Ala Ala Ile Leu Ser Arg Ala Pro Trp Ser Leu
             25                  30                  35 caa agt gtt aat cca ggc cta aag aca aat tct tct aag gag cct aaa       199
Gln Ser Val Asn Pro Gly Leu Lys Thr Asn Ser Ser Lys Glu Pro Lys
         40                  45                  50 ttc acc aag tgc cgt tca cct gag cga gag act ttt tca tgc cac tgg       247
Phe Thr Lys Cys Arg Ser Pro Glu Arg Glu Thr Phe Ser Cys His Trp
     55                  60                  65 aca gat gag gtt cat cat ggt aca aag aac cta gga ccc ata cag ctg       295
Thr Asp Glu Val His His Gly Thr Lys Asn Leu Gly Pro Ile Gln Leu
 70                  75                  80 ttc tat acc aga agg aac act caa gaa tgg act caa gaa tgg aaa gaa       343
Phe Tyr Thr Arg Arg Asn Thr Gln Glu Trp Thr Gln Glu Trp Lys Glu
 85                  90                  95                 100 tgc cct gat tat gtt tct gct ggg gaa aac agc tgt tac ttt aat tca       391
Cys Pro Asp Tyr Val Ser Ala Gly Glu Asn Ser Cys Tyr Phe Asn Ser
                105                 110                 115 tcg ttt acc tcc atc tgg ata cct tat tgt atc aag cta act agc aat       439
Ser Phe Thr Ser Ile Trp Ile Pro Tyr Cys Ile Lys Leu Thr Ser Asn
            120                 125                 130 ggt ggt aca gtg gat gaa aag tgt ttc tct gtt gat gaa ata gtg caa       487
Gly Gly Thr Val Asp Glu Lys Cys Phe Ser Val Asp Glu Ile Val Gln
        135                 140                 145 cca gat cca ccc att gcc ctc aac tgg act tta ctg aac gtc agt tta       535
Pro Asp Pro Pro Ile Ala Leu Asn Trp Thr Leu Leu Asn Val Ser Leu
    150                 155                 160 act ggg att cat gca gat atc caa gtg aga tgg gaa gca cca cgc aat       583
Thr Gly Ile His Ala Asp Ile Gln Val Arg Trp Glu Ala Pro Arg Asn
165                 170                 175                 180 gca gat att cag aaa gga tgg atg gtt ctg gag tat gaa ctt caa tac       631
```

```
              Ala Asp Ile Gln Lys Gly Trp Met Val Leu Glu Tyr Glu Leu Gln Tyr
                          185                 190                 195 aaa gaa gta aat gaa act aaa tgg aaa atg atg gac cct ata ttg aca                  679
Lys Glu Val Asn Glu Thr Lys Trp Lys Met Met Asp Pro Ile Leu Thr
            200                 205                 210 aca tca gtt cca gtg tac tca ttg aaa gtg gat aag gaa tat gaa gtg                  727
Thr Ser Val Pro Val Tyr Ser Leu Lys Val Asp Lys Glu Tyr Glu Val
            215                 220                 225 cgt gtg aga tcc aaa caa cga aac tct gga aat tat ggc gag ttc agt                  775
Arg Val Arg Ser Lys Gln Arg Asn Ser Gly Asn Tyr Gly Glu Phe Ser
230                 235                 240 gag gtg ctc tat gta aca ctt cct cag atg agc caa ttt aca tgt gaa                  823
Glu Val Leu Tyr Val Thr Leu Pro Gln Met Ser Gln Phe Thr Cys Glu
245                 250                 255                 260 gaa gat ttc tac ttt cca tgg ctc tta att att atc ttt gga ata ttt                  871
Glu Asp Phe Tyr Phe Pro Trp Leu Leu Ile Ile Ile Phe Gly Ile Phe
                265                 270                 275 ggg cta aca gtg atg cta ttt gta ttc tta ttt tct aaa cag caa agg                  919
Gly Leu Thr Val Met Leu Phe Val Phe Leu Phe Ser Lys Gln Gln Arg
            280                 285                 290 att aaa atg ctg att ctg ccc cca gtt cca gtt cca aag att aaa gga                  967
Ile Lys Met Leu Ile Leu Pro Pro Val Pro Val Pro Lys Ile Lys Gly
            295                 300                 305 atc gat cca gat ctc ctc aag gaa gga aaa tta gag gag gtg aac aca                 1015
Ile Asp Pro Asp Leu Leu Lys Glu Gly Lys Leu Glu Glu Val Asn Thr
310                 315                 320 atc tta gcc att cat gat agc tat aaa ccc gaa ttc cac agt gat gac                 1063
Ile Leu Ala Ile His Asp Ser Tyr Lys Pro Glu Phe His Ser Asp Asp
325                 330                 335                 340 tct tgg gtt gaa ttt att gag cta gat att gat gag cca gat gaa aag                 1111
Ser Trp Val Glu Phe Ile Glu Leu Asp Ile Asp Glu Pro Asp Glu Lys
                345                 350                 355 act gag gaa tca gac aca gac aga ctt cta agc agt gac cat gag aaa                 1159
Thr Glu Glu Ser Asp Thr Asp Arg Leu Leu Ser Ser Asp His Glu Lys
            360                 365                 370 tca cat agt aac cta ggg gtg aag gat ggc gac tct gga cgt acc agc                 1207
Ser His Ser Asn Leu Gly Val Lys Asp Gly Asp Ser Gly Arg Thr Ser
            375                 380                 385 tgt tgt gaa cct gac att ctg gag act gat ttc aat gcc aat gac ata                 1255
Cys Cys Glu Pro Asp Ile Leu Glu Thr Asp Phe Asn Ala Asn Asp Ile
390                 395                 400 cat gag ggt acc tca gag gtt gct cag cca cag agg tta aaa ggg gaa                 1303
His Glu Gly Thr Ser Glu Val Ala Gln Pro Gln Arg Leu Lys Gly Glu
405                 410                 415                 420 gca gat ctc tta tgc ctt gac cag aag aat caa aat aac tca cct tat                 1351
Ala Asp Leu Leu Cys Leu Asp Gln Lys Asn Gln Asn Asn Ser Pro Tyr
                425                 430                 435 cat gat gct tgc cct gct act cag cag ccc agt gtt atc caa gca gag                 1399
His Asp Ala Cys Pro Ala Thr Gln Gln Pro Ser Val Ile Gln Ala Glu
            440                 445                 450 aaa aac aaa cca caa cca ctt cct act gaa gga gct gag tca act cac                 1447
Lys Asn Lys Pro Gln Pro Leu Pro Thr Glu Gly Ala Glu Ser Thr His
            455                 460                 465 caa gct gcc cat att cag cta agc aat cca agt tca ctg tca aac atc                 1495
Gln Ala Ala His Ile Gln Leu Ser Asn Pro Ser Ser Leu Ser Asn Ile
            470                 475                 480 gac ttt tat gcc cag gtg agc gac att aca cca gca ggt agt gtg gtc                 1543
Asp Phe Tyr Ala Gln Val Ser Asp Ile Thr Pro Ala Gly Ser Val Val
485                 490                 495                 500
```

```
ctt tcc ccg ggc caa aag aat aag gca ggg atg tcc caa tgt gac atg        1591
Leu Ser Pro Gly Gln Lys Asn Lys Ala Gly Met Ser Gln Cys Asp Met
                505                 510                 515 cac ccg gaa atg gtc tca ctc tgc caa gaa aac ttc ctt atg gac aat        1639
His Pro Glu Met Val Ser Leu Cys Gln Glu Asn Phe Leu Met Asp Asn
            520                 525                 530 gcc tac ttc tgt gag gca gat gcc aaa aag tgc atc cct gtg gct cct        1687
Ala Tyr Phe Cys Glu Ala Asp Ala Lys Lys Cys Ile Pro Val Ala Pro
        535                 540                 545 cac atc aag gtt gaa tca cac ata cag cca agc tta aac caa gag gac        1735
His Ile Lys Val Glu Ser His Ile Gln Pro Ser Leu Asn Gln Glu Asp
    550                 555                 560 att tac atc acc aca gaa agc ctt acc act gct gct ggg agg cct ggg        1783
Ile Tyr Ile Thr Thr Glu Ser Leu Thr Thr Ala Ala Gly Arg Pro Gly
565                 570                 575                 580 aca gga gaa cat gtt cca ggt tct gag atg cct gtc cca gac tat acc        1831
Thr Gly Glu His Val Pro Gly Ser Glu Met Pro Val Pro Asp Tyr Thr
                585                 590                 595 tcc att cat ata gta cag tcc cca cag ggc ctc ata ctc aat gcg act        1879
Ser Ile His Ile Val Gln Ser Pro Gln Gly Leu Ile Leu Asn Ala Thr
            600                 605                 610 gcc ttg ccc ttg cct gac aaa gag ttt ctc tca tca tgt ggc tat gtg        1927
Ala Leu Pro Leu Pro Asp Lys Glu Phe Leu Ser Ser Cys Gly Tyr Val
        615                 620                 625 agc aca gac caa ctg aac aaa atc atg cct tag cctttctttg gtttcccaag      1980
Ser Thr Asp Gln Leu Asn Lys Ile Met Pro
    630                 635 agctacgtat ttaatagcaa agaattgact ggggcaataa cgtttaagcc aaaacaatgt      2040
ttaaaccttt tttgggggag tgacaggatg gggtatggat tctaaaatgc cttttcccaa      2100
aatgttgaaa tatgatgtta aaaaaataag aagaatgctt aatcagatag atattcctat      2160
tgtgcaatgt aaatatttta aagaattgtg tcagactgtt tagtagcagt gattgtctta      2220
atattgtggg tgttaatttt tgatactaag cattgaatgg ctatgttttt aatgtatagt      2280
aaatcacgct ttttgaaaaa gcgaaaaaat caggtggctt ttgcggttca ggaaaattga      2340
atgcaaacca tagcacaggc taattttttg ttgtttctta ataagaaac ttttttattt       2400 aaaaaactaa aaactagagg tgagaaattt aaactataag caagaaggca aaaatagttt      2460
ggatatgtaa aacatttact ttgacataaa gttgataaag attttttaat aatttagact      2520
tcaagcatgg ctattttata ttacactaca cactgtgtac tgcagttggt atgacccctc      2580
taaggagtgt agcaactaca gtctaaagct ggtttaatgt tttggccaat gcacctaaag      2640
aaaaacaaac tcgttttta caaagcccct ttatacctcc ccagactcct tcaacaattc       2700
taaaatgatt gtagtaatct gcattattgg aatataattg ttttatctga attttaaac       2760 aagtatttgt taatttagaa aactttaaag cgtttgcaca gatcaactta ccaggcacca     2820
aaagaagtaa aagcaaaaaa gaaacccttt cttcaccaaa tcttggttga tgccaaaaaa     2880
aaatacatgc taagagaagt agaaatcata gctggttcac actgaccaag atacttaagt    2940
gctgcaattg cacgcggagt gagtttttta gtgcgtgcag atggtgagag ataagatcta    3000
tagcctctgc agcggaatct gttcacaccc aacttggttt tgctacataa ttatccagga   3060
agggaataag gtacaagaag catttgtaa gttgaagcaa atcgaatgaa attaactggg    3120
taatgaaaca aagagttcaa gaaataagtt tttgtttcac agcctataac cagacacata   3180
ctcatttttc atgataatga acagaacata gacagaagaa acaaggtttt cagtccccac   3240
agataactga aaattattta aaccgctaaa agaaactttc tttctcacta aatctttat    3300
```

-continued

```
aggatttatt taaaatagca aaagaagaag tttcatcatt ttttacttcc tctctgagtg    3360
gactggcctc aaagcaagca ttcagaagaa aaagaagcaa cctcagtaat ttagaaatca    3420
ttttgcaatc ccttaatatc ctaaacatca ttcattttg ttgttgttgt tgttgttgag     3480
acagagtctc gctctgtcgc caggctagag tgcggtggcg cgatcttgac tcactgcaat    3540
ctccacctcc cacaggttca ggcgattccc gtgcctcagc ctcctgagta gctgggacta    3600
caggcacgca ccaccatgcc aggctaattt ttttgtattt tagcagagac ggggtttcac    3660
catgttggcc aggatggtct cgagtctcct gacctcgtga tccacccgac tcggcctccc    3720
aaagtgctgg gattacaggt gtaagccacc gtgcccagcc ctaaacatca ttcttgagag    3780
cattgggata tctcctgaaa aggtttatga aaaagaagaa tctcatctca gtgaagaata    3840
cttctcattt tttaaaaaag cttaaaactt tgaagttagc tttaacttaa atagtatttc    3900
ccatttatcg cagaccttt ttaggaagca agcttaatgg ctgataattt taaattctct     3960
ctcttgcagg aaggactatg aaaagctaga attgagtgtt taaagttcaa catgttattt    4020
gtaatagatg tttgatagat tttctgctac tttgctgcta tggttttctc caagagctac    4080
ataatttagt ttcatataaa gtatcatcag tgtagaacct aattcaattc aaagctgtgt    4140
gtttggaaga ctatcttact atttcacaac agcctgacaa catttctata gccaaaaata    4200
gctaaatacc tcaatcagtc tcagaatgtc attttggtac tttggtggcc acataagcca    4260
ttattcacta gtatgactag ttgtgtctgg cagtttatat ttaactctct ttatgtctgt    4320
ggattttttc cttcaaagtt taataaattt attttcttgg attcctgata atgtgcttct    4380
gttatcaaac accaacataa aaatgatcta aacc                               4414
```

```
<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
gatgtcccaa tgtgacatgc a                                              21

<210> SEQ ID NO 6
<211> LENGTH: 26
<212> TYPE: DNA
<213> ORGANISM: Artificial Sequence
<220> FEATURE:
<223> OTHER INFORMATION: PCR Primer

<400> SEQUENCE: 6
aagtaggcat tgtccataag gaagtt                                         26

<210> SEQ ID NO 7
<211> LENGTH: 26
<212> TYPE: DNA
<213> ORGANISM: Artificial Sequence
<220> FEATURE:
<223> OTHER INFORMATION: PCR Probe

<400> SEQUENCE: 7
ccggaaatgg tctcactctg ccaaga                                         26

<210> SEQ ID NO 8
<211> LENGTH: 19
<212> TYPE: DNA
```

```
<213> ORGANISM: Artificial Sequence
<220> FEATURE:
<223> OTHER INFORMATION: PCR Primer

<400> SEQUENCE: 8
gaaggtgaag gtcggagtc                                                  19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                 20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                 20

<210> SEQ ID NO 11
<211> LENGTH: 4174
<212> TYPE: DNA
<213> ORGANISM: M. musculus
<220> FEATURE:
<221> NAME/KEY: unsure
<222> LOCATION: 2636
<223> OTHER INFORMATION: unknown
<220> FEATURE:
<221> NAME/KEY: unsure
<222> LOCATION: 2666
<223> OTHER INFORMATION: unknown
<220> FEATURE:
<221> NAME/KEY: unsure
<222> LOCATION: 2759
<223> OTHER INFORMATION: unknown
<220> FEATURE:
<221> NAME/KEY: unsure
<222> LOCATION: 2789
<223> OTHER INFORMATION: unknown
<220> FEATURE:
<221> NAME/KEY: unsure
<222> LOCATION: 3326
<223> OTHER INFORMATION: unknown
<220> FEATURE:
<221> NAME/KEY: unsure
<222> LOCATION: 3352
<223> OTHER INFORMATION: unknown
<220> FEATURE:
<221> NAME/KEY: unsure
<222> LOCATION: 3503
<223> OTHER INFORMATION: unknown
<220> FEATURE:
<221> NAME/KEY: unsure
<222> LOCATION: 3666
<223> OTHER INFORMATION: unknown
<221> NAME/KEY: unsure
<222> LOCATION: 3668
<223> OTHER INFORMATION: unknown
<220> FEATURE:
<223> OTHER INFORMATION:
<220> FEATURE:
<221> NAME/KEY: CDS
<222> LOCATION: (240)...(2192)

<400> SEQUENCE: 11
```

-continued

```
tgacaaccca cgagctgcca agcaggcgca gccatgggaa gaggaggcgg tctagggagc      60
ggcggcactg gcagaggcgg ctgctacagc ggcggtggtg gcgacggctg ttactgaacc     120
ccggcagccg cggggatccc gggctgggtc cacgcggcct gaggcctcgg ctccagcagc     180
ccccaagcgg acacgaaccc gcgttctgtc tcccgaggcg aaactccgag gtctcaggt     239
```

| | | | | |
|---|---|---|---|---|
| atg gat ctt tgt cag gtc ttc tta acc ttg gca ctg gca gtc acc agc | | | | | 287 |
| Met Asp Leu Cys Gln Val Phe Leu Thr Leu Ala Leu Ala Val Thr Ser | | | | | |
| 1               5                   10                  15 | | | | | |

```
agc aca ttt tct gga agt gag gct aca cca gct act ctt ggc aaa gct     335
Ser Thr Phe Ser Gly Ser Glu Ala Thr Pro Ala Thr Leu Gly Lys Ala
             20                  25                  30 tcc cca gtt ctg caa aga atc aat cca agc ctg ggg aca agt tct tct     383
Ser Pro Val Leu Gln Arg Ile Asn Pro Ser Leu Gly Thr Ser Ser Ser
         35                  40                  45 gga aag cct cga ttc acc aag tgt cgt tcc cct gaa ctg gag aca ttt     431
Gly Lys Pro Arg Phe Thr Lys Cys Arg Ser Pro Glu Leu Glu Thr Phe
     50                  55                  60 tca tgc tac tgg aca gaa gga gat aat cct gat tta aag acc cca gga     479
Ser Cys Tyr Trp Thr Glu Gly Asp Asn Pro Asp Leu Lys Thr Pro Gly
 65                  70                  75                  80 tct att cag ctg tac tat gct aaa agg gaa agc caa cga caa gct gca     527
Ser Ile Gln Leu Tyr Tyr Ala Lys Arg Glu Ser Gln Arg Gln Ala Ala
                 85                  90                  95 aga att gct cat gaa tgg acc cag gaa tgg aaa gaa tgc cct gat tat     575
Arg Ile Ala His Glu Trp Thr Gln Glu Trp Lys Glu Cys Pro Asp Tyr
             100                 105                 110 gtc tct gct gga aaa aac agc tgt tac ttc aac tca tca tat acc tcc     623
Val Ser Ala Gly Lys Asn Ser Cys Tyr Phe Asn Ser Ser Tyr Thr Ser
         115                 120                 125 att tgg ata ccc tac tgc atc aag cta act aca aat ggt gat ttg ctg     671
Ile Trp Ile Pro Tyr Cys Ile Lys Leu Thr Thr Asn Gly Asp Leu Leu
     130                 135                 140 gac caa aaa tgt ttc act gtt gac gaa ata gtg caa cct gat cca ccc     719
Asp Gln Lys Cys Phe Thr Val Asp Glu Ile Val Gln Pro Asp Pro Pro
145                 150                 155                 160 att ggc ctc aac tgg act tta cta aac att agt ttg acc ggg att cgt     767
Ile Gly Leu Asn Trp Thr Leu Leu Asn Ile Ser Leu Thr Gly Ile Arg
                 165                 170                 175 gga gac atc caa gtg agt tgg caa cca cca ccc aat gca gat gtt ctg     815
Gly Asp Ile Gln Val Ser Trp Gln Pro Pro Pro Asn Ala Asp Val Leu
             180                 185                 190 aag gga tgg ata att ctg gag tat gaa att cag tac aaa gaa gta aat     863
Lys Gly Trp Ile Ile Leu Glu Tyr Glu Ile Gln Tyr Lys Glu Val Asn
         195                 200                 205 gaa tca aaa tgg aaa gtg atg ggc cct ata tgg tta aca tac tgt cca     911
Glu Ser Lys Trp Lys Val Met Gly Pro Ile Trp Leu Thr Tyr Cys Pro
     210                 215                 220 gtg tac tca ttg aga atg gat aaa gaa cat gaa gtg cgg gtg aga tcc     959
Val Tyr Ser Leu Arg Met Asp Lys Glu His Glu Val Arg Val Arg Ser
225                 230                 235                 240 aga caa cgg agc ttt gaa aag tac agc gag ttc agc gaa gtc ctc cgt    1007
Arg Gln Arg Ser Phe Glu Lys Tyr Ser Glu Phe Ser Glu Val Leu Arg
                 245                 250                 255 gta ata ttt cct cag acg aac ata ttg gaa gca tgt gaa gaa gat atc    1055
Val Ile Phe Pro Gln Thr Asn Ile Leu Glu Ala Cys Glu Glu Asp Ile
             260                 265                 270 cag ttt cca tgg ttc tta att att atc ttt gga ata ttt gga gta gca    1103
Gln Phe Pro Trp Phe Leu Ile Ile Ile Phe Gly Ile Phe Gly Val Ala
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 275 |     |     |     |     | 280 |     |     |     |     | 285 |     |     |     |      |

```
gtg atg cta ttt gta gtt ata ttt tca aag cag caa agg att aag atg    1151
Val Met Leu Phe Val Val Ile Phe Ser Lys Gln Gln Arg Ile Lys Met
    290                 295                 300 ctg att tta ccc cca gtc cca gtt cca aag att aaa ggg att gat cca    1199
Leu Ile Leu Pro Pro Val Pro Val Pro Lys Ile Lys Gly Ile Asp Pro
305                 310                 315                 320 gat ctt ctc aag gga ggg aag ttg gag gag gtg aac acc atc tta ggc    1247
Asp Leu Leu Lys Gly Gly Lys Leu Glu Glu Val Asn Thr Ile Leu Gly
                325                 330                 335 att cat gat aac tac aaa ccc gac ttc tac aat gat gat tcc tgg gtc    1295
Ile His Asp Asn Tyr Lys Pro Asp Phe Tyr Asn Asp Asp Ser Trp Val
            340                 345                 350 gag ttc att gag cta gat att gat gaa gca gat gtg gat gag aag act    1343
Glu Phe Ile Glu Leu Asp Ile Asp Glu Ala Asp Val Asp Glu Lys Thr
        355                 360                 365 gaa ggg tct gac aca gac aga ctt cta agc aat gat cat gag aaa tca    1391
Glu Gly Ser Asp Thr Asp Arg Leu Leu Ser Asn Asp His Glu Lys Ser
    370                 375                 380 gct ggt atc ctt gga gca aag gat gat gat tct ggg cgt acc agc tgt    1439
Ala Gly Ile Leu Gly Ala Lys Asp Asp Asp Ser Gly Arg Thr Ser Cys
385                 390                 395                 400 tac gac cct gac att ttg gat act gat ttc cat acc agt gac atg tgt    1487
Tyr Asp Pro Asp Ile Leu Asp Thr Asp Phe His Thr Ser Asp Met Cys
                405                 410                 415 gat ggt acc ttg aag ttt gct cag tca cag aag tta aat atg gaa gct    1535
Asp Gly Thr Leu Lys Phe Ala Gln Ser Gln Lys Leu Asn Met Glu Ala
            420                 425                 430 gat ctc ttg tgc ctt gat cag aag aat ctg aag aac ttg cct tat gat    1583
Asp Leu Leu Cys Leu Asp Gln Lys Asn Leu Lys Asn Leu Pro Tyr Asp
        435                 440                 445 gct tcc ctt ggc tct ctg cat ccc tcc att acc cag aca gta gaa gaa    1631
Ala Ser Leu Gly Ser Leu His Pro Ser Ile Thr Gln Thr Val Glu Glu
    450                 455                 460 aac aag cca cag cca ctt ttg agc agc gaa act gag gca acc cac caa    1679
Asn Lys Pro Gln Pro Leu Leu Ser Ser Glu Thr Glu Ala Thr His Gln
465                 470                 475                 480 ctc gcc tct aca ccg atg agt aat ccc aca tca ctg gca aac att gac    1727
Leu Ala Ser Thr Pro Met Ser Asn Pro Thr Ser Leu Ala Asn Ile Asp
                485                 490                 495 ttt tat gcc caa gta agc gac att aca cca gca ggt ggt gat gtc ctt    1775
Phe Tyr Ala Gln Val Ser Asp Ile Thr Pro Ala Gly Gly Asp Val Leu
            500                 505                 510 tcc cca ggc caa aag att aag gca ggg ata gcc caa ggc aat acc cag    1823
Ser Pro Gly Gln Lys Ile Lys Ala Gly Ile Ala Gln Gly Asn Thr Gln
        515                 520                 525 cgg gag gtg gcc acg ccc tgc caa gaa aat tac agc atg aac agt gcc    1871
Arg Glu Val Ala Thr Pro Cys Gln Glu Asn Tyr Ser Met Asn Ser Ala
    530                 535                 540 tac ttt tgt gag tca gat gcc aaa aaa tgc atc gct gtg gcc cgt cgc    1919
Tyr Phe Cys Glu Ser Asp Ala Lys Lys Cys Ile Ala Val Ala Arg Arg
545                 550                 555                 560 atg gaa gcc acg tct tgt ata aaa cca agc ttt aac caa gag gac att    1967
Met Glu Ala Thr Ser Cys Ile Lys Pro Ser Phe Asn Gln Glu Asp Ile
                565                 570                 575 tac atc acc aca gaa agc ctt act act gcc cag atg tct gag aca         2015
Tyr Ile Thr Thr Glu Ser Leu Thr Thr Ala Gln Met Ser Glu Thr
            580                 585                 590 gca gat att gct cca gat gct gag atg tct gtc cca gac tac acc acg    2063
```

| | | | | | | | | | | | | | | |
|---|---|---|---|---|---|---|---|---|---|---|---|---|---|---|
|Ala|Asp|Ile|Ala|Pro|Asp|Ala|Glu|Met|Ser|Val|Pro|Asp|Tyr|Thr|Thr|
| |595| | | |600| | | |605| | | | | | gtt cac acc gtg cag tct cca agg ggc ctt ata ctc aac gca act gct   2111
Val His Thr Val Gln Ser Pro Arg Gly Leu Ile Leu Asn Ala Thr Ala
    610                615               620 ttg cct ttg cct gac aaa aag aat ttt ccc tcc tcg tgt ggt tat gtg   2159
Leu Pro Leu Pro Asp Lys Lys Asn Phe Pro Ser Ser Cys Gly Tyr Val
625                630              635             640 agc aca gac caa ctg aac aaa atc atg cag tag cctttcctat ctttaaatgg   2212
Ser Thr Asp Gln Leu Asn Lys Ile Met Gln
             645             650 caagggaaag gctgggcaca aacgcttaaa ccaaaactat gttttaaatc tgtgttggga   2272
gagcatgaga gtggatatgg attctaaaat acttttctg gaaatgtcaa aatatcaata   2332
agtggaaaat caagaattcg taatcagata aatgctccca ttgtgaatta taaatatttt   2392
aatgaattgt ctttaagact gtatagtggc agtgattgtc tgtactgtgg gtcttaattt   2452
tgtgatacta agcattaaat agctacgttt tttatgtatg tagatcatgc ttttggaaaa   2512
agcaaaacaa tcaggtggct tttgcagttc aggaaattga atgcagatta tagcacaggc   2572 tgatttttt tttctttttt aaataactgg gaactaaaac tctaggtgag aaggtaaaac   2632
tagnttggat atgcaaaaca tttattttga catnaaattg ataaagatat ttttaataat   2692
ttacacttta agcatgagkm ctttataata tgctacacac atattgtagt tcagaacaat   2752
ccatctnagg atgtagcagc tacagtgtaa agagggnttc atgttttggt caatgaacgt   2812
aaagaaaacc aaacaagtta gatttttaca agcccttttt ataacttcca aaacttctta   2872
actctaaaaa tgtctaataa cctgcattat tagaaaaaaa cattttaaat ttgtaaacga   2932 atatttttt aattttgaaa actttatttt tttttaatgt tgaatcaacg tatcatacac   2992
caaacagtaa acagaaatta taataatgga agaagtgctt tcttcgacaa atttccattc   3052
aagccacaca gctacatgta agagaagtag aagtgatgtg gtgtgattgg ctaggatgca   3112
gaagagcttc aggaatacaa gaagtgagag cccaaggatt gggaggaggg ggctctcaca   3172
tctccacagt gcagtctgtc aaacccagct tggtttttat agtattctaa gaattattgt   3232
gtacaaggaa aagtctcaca tgtatgaaat ccagtatcca gatgggtaa agttagcaga   3292 taataggata ggaaattaaa gacctagatc tagnactagt ggactttttt cacagacagn   3352
acacaaattt ttaattcagg gagaagggac agaataaatg acttcccact cacaaagcac   3412
aactcagaag taattaaaca ggtaacgaaa accttgccat caaacctttg ataagatgta   3472
ttttaagtag taagcagtat ttcaatgctt nttacttacc ctcccaggac aaccgatctc   3532
aaataagggg gataaggtag ataaaaatca cttttgatt ctgtaataac ataaacatag   3592
ttctttgggt tagcaccccc ccaaaaaaaa atttatggga gaagaggac tctcagctga   3652 ctgaagaata catntnattt aaatattttt tagatgcctg aaactttaaa attacccttta   3712 agttttaatg gattaccatt ttgccaagac ctttgtgggg aaacaagctt aatgtttagt   3772
gattttgaaa tctctttcat gcaggagaga cagtgaaaat ctagccttgg gtgtttaagg   3832
ttcgccttgt tactttgtaa tagatttaa taagttttc tgctactttg ctgctatggt   3892
ttctccaatg gctacatgat ttagttcata tgaagtatca tcaacttaga atctattcag   3952
cttaaagatg tgtgttttga tgaactatct taccatttca ccataggctg accacgtttc   4012
tatagccaaa aatagctaaa tacctcaatc agttccagaa tgtcattttt tggtactttg   4072
ctggccacac aagccgttat tcaccgttta actagttgtg ttctgcagtc tatatttaac   4132

```
tttctttatg tctgtggatt tttcccttca aagttcaata aa                    4174
```

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12

```
ttgacgaaat agtgcaacct gatc                                        24
```

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13

```
cgaatcccgg tcaaactaat g                                           21
```

<210> SEQ ID NO 14
<211> LENGTH: 26
<212> TYPE: DNA
<213> ORGANISM: Artificial Sequence
<220> FEATURE:
<223> OTHER INFORMATION: PCR Probe

<400> SEQUENCE: 14

```
cattggcctc aactggactt tactaa                                      26
```

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15

```
ggcaaattca acggcacagt                                             20
```

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16

```
gggtctcgct cctggaagat                                             20
```

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17

```
aaggccgaga atgggaagct tgtcatc                                     27
```

<210> SEQ ID NO 18
<211> LENGTH: 34099
<212> TYPE: DNA
<213> ORGANISM: H. sapiens

```
<400> SEQUENCE: 18
tgataaccag ctcagaacac acacatatta gttgttctcc ctttccttcc cacccccccc      60
attccctgac tgctagatcc agaagtcatc ttccagatga actacctata tccaaatcct     120
aatctctagc tctggtttct taaacaggtc ctatgaaatg cttgaaataa aaggcaaaat     180
ggtttgtgtc tagaatcaaa ggctgacaat ggcaagcaac aggcactaaa actatgaccc     240
aggaaaaatg cttttctgga agacatcggc attacctcct agacacggaa tacactggct     300
tcatcccagt agtttcttca cacactttag atacgtgtct cattaggatc acatatgact     360
cacctgattt catgccttgc ctttttcttt tattctgcag attcttctaa ggagcctaaa     420
ttcaccaagt gccgttcacc tgagcgagag actttttcat gccactggac agatgaggtt     480
catcatggta caaagaacct aggacccata cagctgttct ataccagaag gtgccaccat     540
catgcctttc tgattttcct ctccatggat gtacctacta agtacactg agtcagatgt      600
actgtgggaa tggaagtgat tgttgtgat ttatgcaatc aatgaatatt cattcactca      660
tttattgaaa aaatattaa tcaagcccat cctatgtgct gagtactatt ttaggccctg      720
gagatatagc agtgattaca aaagacaaaa tccctggtct catggagatt tccttccaat     780
gcagggagac aggcaataaa aattgaatta aatttcagct agtaatatag gttattaaga     840
aaataaagc cagaaagcag catatcagca gtgtgtggga gtttgtgtat gtgcatgaga      900
atgtgtgaga gtgtgtcaaa gtgtgagtga gagcatgtat ggatacacgt gggcatgtgc     960
atgtggatga gagtgtgtgt aaaaggcttg aatgatgctg aaatgcgtgg tcctaggagg    1020
cctctctatt gtggtgtcct agaccagaga cataagtgaa acgggacagg ccacgtgagt    1080
atctggggga aaggctatgc aggcagagga aattgcaagt acaaagtccc tgaggcagtc    1140
ttggcatatt tgagggatga aaaaggccag cactgaaggc acaagattga aagtgaggag    1200
agtgatatgg gaagggatca gagagttact tagggactga ccatgccaaa cctcataggc    1260
aagggcaagg ctttgaattt tactttattt gtggtggaaa gctataggtg ttttgaaaa     1320
gatatatgct ttaaaagatg tagctttgtt tctaaccaga taatacactc cttctcttaa    1380
atatattcag taaaagactg tagtacttt tcatttttac cagtgaccct ctaaaataac     1440
agaggaaggg tgaaacaaag acctctcaat ataggtacca tccaagttgt ttatttcttc    1500
cccttcacct ggcattattt tcattttgt ttactctcac tgtgtatatt tttccctttt     1560
ttacatttta ggcttaaaca cttcattatc tcctgttttc cacccaaccc ccagagaagg    1620
cctaagccaa gatgcagggt tagtgaggac cctttatcct tggctcaagg tgttcgttag    1680
tcagaggatg acattgtcta tccaaccgaa gagctggaat agggaaggaa gatgcagcca    1740
gcagttaagg gtatgagctc agggctaaca aacctgcact tcagtgtagt tctgcacttt    1800
ctcaccaagg aatactaggg aaattagcca gtttgtgtac aactcagcct cctcatttgc    1860
agaaaggaga taatggactt gcctcatgac ttcttgtgag gatcatatga gataaccat     1920
gaaaaatact tggcagagta cttgacacat aataagtact cactaaatgg tagctggtat    1980
tcttcttatc ggtagtatag tgataatttt aaaataatta tgatatagaa atccagttcc    2040
tggactataa aatgactata aattgtataa gaccatttat accagtaaat tgttataatt    2100
attttaatta ttggtataag agcatttta tgcagagctg ctgcttaatt tgcagataaa     2160
aaaatacttg gagttagcaa ccaagcgac cttccccacc tttcagtata agagaggtct     2220
cttggatgaa gtgaagtgaa gatgaaatgt ttgggcacca agtatactat attttccctt    2280
```

```
aaggctgaca ccacagagag gttggggcca gtaaacagag ttgatttcta taaatacatt    2340
cagacatgaa gttagtatgt ttgatgacac ttttgaaatg tgtggaatca ttaagttatt    2400
tgtacaggca caattagcca aactgtaaag aaaagtagca gaataacctc ttaagctggg    2460
cccactttat gaaaataatt ttttgctacc tcaatattta ccaaatttga tgagcaaaaa    2520
gagaaatcca aaggaatgaa gccttgataa atatatatcc cttgccctca tcaatcaggg    2580
tcacataact ctgtccacag gcatcttatg cacactccag tcatttcagc atctctggtt    2640
caaatccagg atctacacta ccaaggatgc tgctgaaagt gtgactgggt aaagggaaac    2700
gttcagacat attcagaaag atgtcttaga ttttgccctg gtagtgtttg aatcccagg    2760 agggtaagta cagcttcatg attaagtgcc aacccaaact tacaaaatta gatatttgtg    2820
ttttttctat aaaatataac tattttgaat atcttagcca aactactatg agcccacagc    2880
ccagtttatc caagaaggat aaaactgagg gattaggagt atcaggactg gactggactg    2940
attagtgtac agttatattt gatttctcat tgcccacttc acagaaaga caatacaaat    3000 gcactttctg actcttatca ctgtttctta gaactcagtt gccaggcaac tcctgaaact    3060
atagaaacat gcttctcatc cctgacacat aaataaaact ctgagatgat tttatccaaa    3120
gtcagagtca gtgggcagtg cagttgtttc agtttgctgg cctggcctca gtatctaaag    3180
cacaacagaa cgtgaacatg tcaggctgtc aacaggacag ttcaggcaca gccctacagg    3240
cagttgtgtg ttttgcctgg ctctgctcct tgccaggtgg ctggcagaaa aggcagcctc    3300
cacatgttag agcagcagat tcaaaacagt gtctgccatc ctgtgatgac gatagtgcca    3360
aattcagcct ctgagcttgc aggggactca ggatgaatgc acattacagg catggtaaaa    3420
agaggctctg ggaagcatgt tcgagctgct ctgctctcag ctccttgcat gtaaatgctg    3480
tgtttttaaa ggaagtgggc atgtgaacac tcagtcctta aggctgtatc ccccacctct    3540 tccatacca ttcaaccca cttcaaaaat taccctggtc ttaagagaaa tttcatttc    3600 tatacaaggt tgtgtggaaa atcagtaggg agaaagggca ttattacttt cattttctt    3660 taacaaaagt attaaattta aagccaaaaa cgtgcgcttt ctgtcatgaa aacagctgcc    3720
cttaaaaaca taaatgatgt tttatttta ttacttttat ctagttggtt gtctttagat    3780
gaaaaacatt tcttctgctc tttattctta tttttaatga tagtctcttt ctatggttct    3840
caccccttcc atttcacaag atagtctggg agcaaaccta aagcacttaa cttttgggag    3900
taagagcaga ggggagcttc catacattga ttttggtcat ctgtagagac attcaaccca    3960
gagaaggcaa gtgacacagt atctgtttta tgagctaatt tgggttcttg tctacattta    4020
atagtttaaa atataagtta taaatattta tttaaaatga aattcaacat tggttcatga    4080
agaaagaggt tggaagtagt gttttgaact agctgtttct gatccatcat gcttaaaata    4140
aatgctctgt ttgtcctgtg gagttcatgg atttgggata atctaaacag ggttttttaa    4200
acagtcctca tggggaacaa ggtactgaca tgcactgttg agaaattctg tgaatcatga    4260
aagagctaat cttttagaaa tccagacctg ttaagcacta atctacatct ttggaatatc    4320
ttaatacttt gagttttcta actttatac tgtcacttat gctaagtaca tttgatatcc    4380
cttctattat gtgaaagcct cattttctgg gcaatttct tacaactact ctctttaatg    4440
cactcttact taatttgaaa gtaaatatca aattaagcat actatagttc aatgaaccac    4500
ccacctattc ctaatttttt taacatttct cttctgactc tacatacaca catacttaca    4560
cacacacaca caaacacacc ttatctttc ttctgccttt tgcccattta cttttgcat    4620 cagagatgaa tctctcattc aagcatatgc aacttttttt ttttttgaga tggagtcttg    4680
```

```
ctttggcacc caggctggag tgcagtggct cgatcttggc ttactgcaaa ctttgcctcc   4740
tgcgttcaag caattctcct gcctcagcct acctaccgaa tagctgggat tacagaagca   4800
tgccatcatg cccagctaat tttgtatttt tagtacaga tggggttta ccatgttagc    4860 caggctggtc tcaatctcct aacccatgat ccgcctgcct cagcctccga aagtgctggg   4920
attacaggca tgaaccaccg tacccagcca gcatatgcaa cttttaagag tctcaaccaa   4980
agcagcaatt cactgtctca gaccctggag tctctgccat ttaaatccca atttccttcc   5040
aacagctgag gagcagctgt ctcaaggacc ctctgatact acacaagttt tctcctagtg   5100
ccaagcagac cagcctgaga aacagctata agaaggaaat aggcgtcttc tcccagcttg   5160
gcatcctttc cttccaggcc ctgccttccc tacaacctgc attgtcttca ttgtccactg   5220
ctgcccagca cccatcccac agagggatgg tcccaaacct ccacagtctg gcctgtgagc   5280
cacaggcgcc tctgcctgca cagggccatt cctacctcat cttccacaac cacagattac   5340
atggttttat gtccctttga cttatatatt gtcttctcaa ttaataggct agtgaataac   5400
atggagatga tgaactacct cacccaagta gcaattctaa tttaagaaaa ttttcctgtc   5460
attccattgc cttttacttc cattaccaca ctcatgccca tacttcctta cctcaatccc   5520
tttgacctct ctgtttattc ccttccttgc cgtattgcca tctattaaac ttttacccat   5580
ccttcaagaa tgctaaaaac ataccctcac cttgaagcct tccatgaaga gccagagcaa   5640
tcattccctc ttctgaactt taaggaccc tagagagcac tactaatgag cacttaccca    5700
cattgctttg taatatggtt ttttactctt tccttctgag gcaggaggaa ttccttagac   5760
atctatgaat cccatagtgt ctgtcattat gttttagaca taaccaattc tcattaaatg   5820
tcaatagaat gaatataaga ggcccaaaaa actactcaga tgggaatttg agtcttattt   5880
tagcctgaaa ttaggggacc acatcttact tatctttata tctgcacagc gttggtgctg   5940
gatataatgc atcactctgc ctggagcaca catcaacttg tctcctcagt ttctttcacc   6000
ataggctggt gaaacagcca ggtctaaacc ttcactgttc tctgggaatc tctagtttgg   6060
gggtgattct ctgtactgtt ttaatgaaca ttttttaaaat gtccctaagt ctcagaacct   6120
tcatctatac aactggcata taaagtacc taccatagga atcgatttat gagcaggcat    6180
agcatattca ttcaataaac ggaagtttta ccataggcag aagtaccaaa cggcctcgta   6240
gcagtcgtca gacactgatg atactgtcca ctgatgtgat atgtctcgga aatgatgtta   6300
ctaaaatacc tcttcacaaa atatttgtct tccaatttat tgaatcagac tatcaagcac   6360
cttacttgga cttaagctac aacatgattt ttggaacaat taatcttttt ttaacccttc   6420
attttaggaa cactcaagaa tggactcaag aatggaaaga atgccctgat tatgtttctg   6480
ctggggaaaa cagctgttac tttaattcat cgtttacctc catctggata ccttattgta   6540
tcaagctaac tagcaatggt ggtacagtgg atgaaaagtg tttctctgtt gatgaaatag   6600
gtaaatcaca ggttttttgtt tcatttgaca tagttttaga ctaaataaat ggggaagcct   6660
gcaaggtcca agtataatca gtaggaaga cttttgtaaca gtgttctata gatacatgga    6720
gatctgtttt acaggagatg ggatcagctg gtgaacaaga ggaaaagggc aggggggaact  6780 taagttgact ttaacataaa gtagcctggc agtaaatgtt gtgaagaaga gaataggaac   6840
cttgtggagt cttttccttt aggatatctt tgaagctgcg ttgtgttttt atgttccact   6900
gcaaagggtg aacttaatat attccttagga tttcttactt cctaattatt tgataggatc   6960
cttatattca aattcactga aatacgttgg cctttgacct ctaccattgc tgtaatcaaa   7020
```

```
gcctacattt tctttatcac aaagcataat cattctggaa ttttacatt acaaaacagc      7080 cacagttact ttaaagacat gtttattaga tctcagaaca aatactggag acaatcagct      7140
cagtgaacta agtgaaagat ccaaacagag gatcctttgc ccatcatatg gacacaaggt     7200
ggaaacaaaa caaataaaac aaacaattgt aattagaata gtcatgttta taccttaata     7260
gtataaatag caaatagaa agaatcaaag aaggactttg agtagctgaa attagtgcct      7320
caaaatctat ccacaaaagc tcatttgttg cttataggaa tttctcgttg cttctcccaa     7380
atgtattgtt ctttttatgt ggttttctag gcataagctg actggaagac ataggagtat    7440
gtggctagaa cttacagata gaaacaaata aaatctaata ggctgactt aagggagaag     7500 attaagagaa ctgtatcaag cagtaaagat aacccaattg ctttgcaaag acaatttagt    7560
atgtgtccta acatcagtgg gtatagctgt tgagttgaaa ctaaatggga tagcagaatg     7620
ggatagtagc aagaacactg ggttaaaacc catgttctag ccctgttctc tgccaatagc    7680
cagtcctact catttacctg gctgacatgc ctgtcatgtg tcacgcactg ttctggtggt    7740
ggtggttata gaataagtac aatacagtca agagggaag tcaggcatgt tcacaaataa     7800
ttgcagtgca gcgtgatagg tgttagcctg gaaatacgtg gaatgcagag ctgcaaaggt    7860
ggtggccaaa ggcgtgaatg actgacaggc ctgagggatg aggaagggct gcacagagat    7920
ggtgacagtt tagttacctc tgaactggaa ttggactctc cctattttta aaaaagtgat    7980
gacccacagt ggtcaaaagc atgagtgagt attgtcaggt accacagtgg acttgccttt   8040
cagtaactac taagttccaa cagtaactta gtagttactt agtaattaca acagtaactt    8100
agtagtccca acatgttcag ggactcagga gcagttagga agccctccta gtcagctgga   8160
gaaatcatca gtagttgttt gtgccccaaa aaggaatttg gactttaact gtcacgaggt     8220
acctttgagg atgtttaaat agggaaatta cttgaggata ctaatagtta acagtcacaa    8280
aagtcttacc atgtgtcagg tataaaaacc atcttttgca atcacacttt acagataatg    8340
aaaccgaggc acagagcagt taaaggacta gttcaagtca aacagctagt agatagagct    8400
gggatttgaa cctccagcct ccatgctctt actcttgagg ctttgcagta ccacttgtct    8460
ctttattaat gctcagagaa attaatcttg ttgcaatgtg aaacgtagat tggagtggga   8520
cggactagag gtagaagagg ttaaaagact gagatgatca aggtaaaaga ttatgacagg    8580
tagctacaac tagcacaata gttgtggggc aaggtgctga gagtgaaaga gaacaaagaa    8640
ctaatgtaac cctggtagat cttgagaaag ttgtcaatca ttataagcct cagcttcctc    8700
ataaaatatg tatgtatggt actacctcac agggctattc tttggatttg aagtactata    8760
ttagttagac atttgtcatt cattcaattc attcagcaaa tatttattat gctcttctct    8820
caggccagtc aatgttctcc atgctgggga tagaaactgt cttccctggt gggatttaat    8880
cccaacgagg atgaaagcg acaatgctat ggagaaatat aggaaaggag aataggagtg     8940
ttggagaggt tgcagtgttg agttttcagg attggcatcc ctgaggcagt ggcatttgaa    9000
taaagaagga ttggagagga taattatgtg tgtgtctcag ggaagggcat ttcagcaagg    9060
gggcacgcca gaagaaagat ctcaaagtag gagcatgctt ttcctcactc aatgaacagc    9120
aggccggcgg tggagtgggc acagagtgag cgaggagact ggtatgagac caaatcgcac    9180
agacaagaca gtcaaatcta cccaaccatt gccaaagact ttggctttca cttggagtga    9240
ggtaggcagc ctttggaggg ttttagatga tgagcgatgt gatctaacgt aagtgttagg    9300
ataatcactg tgtcagttcg cttgaggatt gcatggagaa tagactggag ggggacaaag    9360
accaaagggg tacagtgggg agacaaatga agcaagaaga atgaaaaagg ataatggcca    9420
```

```
ggaccaggtt attagtggtg caggcggtgg gacatggttg gattctgtta tatcttgaaa   9480
gtacagctga cggaatgtgg attagtgagg aaaagatgag ccaaggacaa gttcattgtt   9540
tttatcctga gcaactagag gaattgagtc ctcgttaaca gagatggaaa agaggaaagg   9600
agagcaggtt ttggagagga agagcaaggg tttgtttggg gatatattaa gtttcagata   9660
ttttttaaat atctcacagg agttgtcaat atagcatgta gatttatgta tagagataaa   9720
ggagaggtca ttattatgcc tgtaatggta tctcacagga ggtcattgtt atgcctgtaa   9780
tggtggtacc aaatcttttc caaaaggacc ttgtctcata tcctctattt ttcaaatgca   9840
gcataagtaa tgagttatag aaaatcttcc attaaaaaca attttatagt ttggtcactt   9900
taaacggtta agctttgatt atcaggattc ctgaatctcc aacaaatcca gaagggtgag   9960
gaattattgc cattatatcg gcatatgtag tttggccatt ttgcatatcc ttccaattta  10020
attttcaaaa tgtagtcatg attcatcaaa ttttgactct ccctgttttt aaaaaggtgg  10080
tgtcgacccc acagagggca acagcatgct cctccaccat aaggcctgtt ttcactgtgg  10140
gtgcacacaa gagcttccct ctttggccaa cagatttgac agccagtaag agctcctcac  10200
tgtgtatatc tgtaaagtta tctccagtca acgctaggga tgcacactct gcaacactct  10260
aggtggcctt ctgtatatat ggcagaaaaa gaaagtaaat tttactctgt atctgcaagt  10320
gattttcaaa accctcagta atgagatcca actagcaaaa atttaccagg aactctctag  10380
aatataaatt tagacatagt tcctagcttt ggaatccata ttttcttca tcagcctctg  10440 agaaattgtg gtctttgagg tcctactaag cagaatgcaa caattttcg tggaactgta  10500 gagtatatca atagaacctg aggaaaacaa tgtttcaagt tgttcatgtg acagtcaaaa  10560
agacagaaaa cactgaattg tcaccatttg tgagactagc ataatgcttt cttccttctt  10620
atgtcagaag aaaatatcac atgtggctag gaagatcaca aagctaggga gcattagcag  10680
agtgtgcagg aagattgtat gagaagattg aagaagagta aaaaggata atggctagga  10740 ccaggttata gtggtgcagg cggtgagata tggttggatt ctgttatatc ttgaaagtac  10800
agctgacgga atctgacgga atatggatta gtgaggcaaa gatgagtctt tcagggaaca  10860
acacagaaat gaggtaaaca gggtctctgc ccccaggcca tacatagttg caagaaaaaa  10920
ggtttctcta cccctagttc cgaagcagcc ccatgtctaa attctgtaag tctttctgac  10980
tctctgtttt ttcagtttca agtgaaaata aattccttg ccaaaatcct gatgcattta  11040
tgatatcaga gcaaaagaa atatacaaca tggcagatct tgtaaatagt gatcagatgt  11100
tttactccaa aaggaatttt tgtaagggct tatttagaag ttaaaaacaa gtcatccttg  11160
agttaaaaaa aaagttact ctcttataaa gtgaaagtta taataagaaa atattggaa  11220 gaaataagag catgaatgat caaaaatgta gaaagtaatt tggtcttctg agaagaatgc  11280
cttccattaa tattaaattg tgtctgtctg tgtactaatg ctctgttgaa ttgcacagtg  11340
caaccagatc cacccattgc cctcaactgg actttactga acgtcagttt aactgggatt  11400
catgcagata tccaagtgag atgggaagca ccacgcaatg cagatattca gaaaggatgg  11460
atggttctgg agtatgaact tcaatacaaa gaagtaaatg aaactaaatg gaaaatggta  11520
agatgttgct acaccttaca ctttgacttt tcttctatt tcaacaaact ctctctcatt  11580
tatcattaga cttccttg acctaatacc acatgttcat gctgtatgct ccataatttc  11640
ttaattgaga aaacatttatt taaccggtaa aatattgtct tgaaattctg taagacagga  11700
gatgcttatg tatatatgga ggcctgtgga aggaaaggaa aactatttct ccattcattc  11760
```

```
ttgctgtcca gtttaacttt agagcaaaat tatagactgg ccacttagct gtctttgggg   11820
atgtggataa aaatgggaaa gtttgtgatc cagtcaacag tgactatggc caaatatttt   11880
cccatgattt cagttgctgc tactcaaagg actcccacta aaacaaattc atacgtgtct   11940
ataggaaaac agagggaggg aatttgtctc ttagaggttt cagaaggatg ttttgttaca   12000
tacctcagag aagaatcaag ctgagattct tatgtaggca attagagagc atggtaccag   12060
ttgacctctg aatccctctc ttccttacca agcatatgga actcagcatt ttgataaatt   12120
tcacatggca cataacaaga ggaaaaacag gagtatcatg ctgctcccaa tataactaat   12180
tctaaatctg tctaaccaca gccacagcca cagccacagc caagccaagc agtttctggc   12240
cactcatcag gtgatgccca gcagcctggc acagatcact cccagaattt tgagacacca   12300
ggacattcag tgagccactg aaaaagatgc caattttgtc attagaggaa agttaagttt   12360
ggaggaaatt tgagtagtta caatactggg ctttgaggct ctattttctg aatcatttta   12420
atttagatat ctgttctgta acttggtaca aataaaatgc ctgattggat gctaagtcaa   12480
acaagactgt ctaaatccaa gctacaatca acattatttt aacaacaggt actgaaataa   12540
ctactatgca gaaggcactg tgctaaatgc ctgaggtggc ggttctcaaa gtgggagcca   12600
cagacccttg agggtccctg agaccctttc agggagttca gtactatttt cacaatacac   12660
taaaatatta ttttattaac tatgttgaaa tttaacttaa tggcacaaaa gcaatgctgg   12720
aaacactgct ggcaccttag catgaagcaa ggcagtagga tcaaatttta ctaatagtca   12780
tgcactccca atgaagaagg aagaaaaagc cagtttcacg tttgaagttc ttgatgaagc   12840
tgtaaaaatt gttaatttta ctaaacctcg acctttgagt acatagctta ttaatattct   12900
gtgtgacata tgggaattac acattaagca tgtctgctgc gtactgaggt attgtatttg   12960
tcttgaagaa aagcgcttaa atgactgagt tgccagctga actagttgct tttattgctt   13020
ggagcaccat ttttacttgg aagagccatt gataaactgg cagatggtta ttcatatttg   13080
aattggcaaa catttgtcaa aaaagaatga ggcaagcttg tcgcttcaag aaaaacaact   13140
gacagtattt tttgcaatgg aaaaaatttg acttttcaaa gcaattcatt ttgcctttt   13200
cgaaaatttg tgtctccaac cgtgagcttg atagtgtttt aatatttgaa gacttttctt   13260
gaagagattg atggtgatat taatgaaagt gactttttaa ttatattgtg taataaaatg   13320
tatgaacatt tagaaaaatc tacaactcag ttaaccaata ttttccaaat tactaataca   13380
tgatgtaatc aaatcatgca tgggaaatga atccattcaa agtactagat agaatcgtga   13440
attttttaa tgatcaaaaa tttttttgta tatttattgt gtacaacata ttttttgaa   13500
atatggatac attgtagaat ggttctatca cactaagtaa catatgcatt accacacata   13560
cctttttttg tgtgttgaga acacttaaaa tctactcaga gattttcaaa atacaataca   13620
taagcattaa ctatagtcac cattttgcac aatagatttc ttaaactcat tcctactaac   13680
tgaaaatttt aattctttca tcaatatctc cttaactctg caccctgccc acaacccctg   13740
ataaccacca ttcaactctc tgcttctgag ttcaacttt ttagattctg catataagtg   13800
agattatgtg gtatttgttt ttctgtctct ggatcatttt tcttaatata atatcctcca   13860
ggttcatcca cattgtcaca agtgacagga tatccttctt ttttaaggc tgatagcatt   13920
ccattgtata tacctaccac attttcttta tccacttatc cattaatgga acataggtcg   13980
attctatttc ttggctgtta taagtaatga acatgggagc ccagatattc tggctcaaca   14040
tactgatttc attttccttg gatatatact tagtagtgga ataatataat ggatcacatg   14100
gtagttctat ttttaatctt ttgaggaagc ttcatattat tttccataga gggtatacta   14160
```

```
atttacactc ccaccaatag tgtgcaaggg ttcccttttg tccacattct caccaacact   14220
tgttatctct tctttttttg aaaatagcca tcctaacatc tttgtgcact ctatgccttc   14280
tgtgagctga tagctcattg tggtttaaat ttacatttcc ctgatgatta aagatgtcaa   14340
gcatttttca tatacctgtt ggccatttct atatcttctt tttaaaaatt tatattcagg   14400
tcctttgccc attttttaat tgggttattt tcttgttatt gaattgtttt agttccttat   14460
atatttcaga tagtaacttc ttatcagatg tatgcaaata ttgtctccca ttccatagag   14520
tgtcttttta ctctgttgat tgtttccttg gcagtgcaga agcttttttag tttcatgtaa   14580 tcccgtttat ctatttccac ttttgttgcc tgttcccaat ggagtcatat ccaaaaaatc   14640
attgcccaaa ccaatgtcat ggagcttttt cctatatttt cttccagtag ttgtacagtt   14700
tcaggtttta catttaagtc tttaatcgat tttgagttta tttttgtata tgaggtaaaa   14760
taagggtata atttcattct tctgcatatg gatgtccaat tttcccaaca acatttaaag   14820
acagagtcct ttccttactg tgtattctta gcacctttgt gataaatcaa tttactgtaa   14880
atgtgtggat ttatttccga acactttatt cttttacatt ggtttatgtc attttatgc    14940 cagtaccatg ctgttttgat gactatagct ttgtattatg ttttgaggtt ggtagagtga   15000
tgatttcatc cttgttcttc ttgttcaaga ttgctttggc tattcatagt ctattgcagt   15060
tgcatacaaa ttttagaatt gcttttttcta tttctgtgaa aaatgacatt ggaattttga   15120
taaggattgc attgaatctg tagattgctt taggtagcag ggacattcga acaatattaa   15180
ttcttctaat ccatgaacat gggctatctg ttcatttatt tgtgttgtct tcatgtttta   15240
cagttttcag tgttcagatc tttcaccttt ttgttttaaat ttatttctag gtcttttatt   15300 ttattttttat ttttatagat attgtgaaag ggatttctttt atttcttttct cagattgttc   15360 cttattagtg tatagaaatg ttactgattt ttgtatgttg actttgtatc ctgcagcttt   15420
actgaatttg tttatctgtt ctagcaattt tttgttgaag tctttagggt tttctatata   15480
taaaatcatg tcatctgtaa gcaaggacaa tttaactttt tccttctcaa ttttggatgc   15540
cttttatttc tctcttttgc ttaattgctc tgactaggat tttgaatcga gtagaataga   15600
gtagaggagt tacattgaat aaaaatggca agagtaggca tctttgtctt gttcctcatc   15660
ttagaagaaa agctttccac atttcactgt ttattatgat gtgagtttgt tatatatggc   15720
ctttattgtg ttgaaataca ttccttctat atctaattgt taagggtttt tatcatgaaa   15780
ggatattgaa ttttgacaag tgcttcttct gtatctgttg agatggttcc atggttttcg   15840
tctcggttct gttaaagtga tgtattatgt ttatgtattt gtgtgtgatg aaccatcctt   15900
gcatccctgg aataaatcct acttgatcat ggagaatgtt ccttttagtg tgcttttgag   15960
ttagtttcct agtatttttgt ttaagatttt tacatctgta tttatcagag atattagccc   16020
ataattttct tttcttgtag tgtccttttca tggtttgggt ataagggtaa tgctagcatc   16080
aagaaatagt ttggtagtat ccccttttct tccactttt ggaaaagttt gagaaggatt   16140
ggtgttccgg tgaagcttcc agtgaaactg tcaggtcctg gacttctctt tgatgacaga   16200
ctttttatta ctgattcaat ctccttactt attattggtt tattagattt tctatttctt   16260
caagaaagtc ttagtaggtt gttgtgtgta ggaatttatt catttctcat gcatataatt   16320
tttcagaatg gtctcttatg aacatttgta tttctatggt attggttgta atgtctcctc   16380
cttcatttct gatttttgttt ttaatttggg cttttctcttt ttttattatt tagtctagct   16440
aaagattggt tgattttgtt tatcttttca aaaaaacttg tttcattaat cttttctact   16500
```

```
gttttaatgt gctaactgaa aagcacatta aaaggatcat tctccatgat caagtaggat    16560
ttatcccagg gatgcaagga tggttcatca cacgcaaata cataaacata atacatcaca    16620
ttactagaac caaaaacaaa attatggaac catctcaata ttttctattc tctatttcat    16680
ttatttctgt tctgatcttt attatttcct tccttctatg aactttatgc ttagtttatt    16740 cttttctgg tttcttcagg taaaatgtta ggttattcat ttgagatctt tgttttctga     16800
tggaggcatt tattgccatg aacttccatt gctcttagaa cgacttttac tgcattcctt    16860
aaggtttgct atgttgtttc cattttgtc tcaagatatt tttgatttta tttttactt      16920 tttaactatt ttttaggtt cagagataca tgtgcacgtt tgttatatag gtaaattgca     16980
tgtcacaggg gtttaccata cagattattt catcaccagg taataagcat agtacccaga    17040
aggtagtttt tgatcttca ccttccttcc accctctacc ctccagtagg ccccagtatc     17100
tgtggtttca gtcttcgtgt ccatgtgttc tcaatgttta gctcctacta ataagtgaga    17160
atatgtggta tttgttttcc tgttcatgca ttagtgtgct tagcataatg gcctccagct    17220
ccatccatgt gactgcagag gacatgatct tgttcctttt tacgcctgag cagtattcca    17280
tggtgtacat ataccacatt tcctttatcc agtgtaccat tttctttatt ccatgtcttt    17340
gctattgtga atagtgctat gatgaacaca cgcatgcatg tgtctttatg gtaaaatggt    17400
ttatattcct tcaggtatat acccaataac gggactgctg ggtcaaatga caattctctt    17460
ttaagttctt tgagaagttg ctaaactgct tgccacaatg gctgaactaa tttgaattat    17520
taccagcagg atataagtgt tccctttct ttgcaacctc accagcatct gttatttttt     17580 gacttttga taatagcctt tctgactgct gtgatgtagt atctcattat ggttttgata     17640
tgcctttctc tctaattatt agtaatgttg agcatttttt cttacacttg ttggctcatg    17700
tttgtgttct tttgaaaagt gtctgtttat gccttttgtc cattttttaa tgggactgtt    17760 tgttttggc ttgttgattt aaagttcctt atagattctg gatattagac atttgtcaga     17820
tgtatagttt gcaaatattt tcagccattc tgtagattat ctgttttttc agttgtttct    17880
tttgctgtgc agaagctctt tggtttaatt agatcccatt tgtcaatttt tgttttgtt    17940 gcaattgttt ttggcatctt tgtcatgaaa cctttgctaa ggcctatgtc cagaatggta    18000
tttcctaggt tttcttctag ggttttata gtttggggtt ttgcatttaa accttaatc      18060 catcttgagt tgatagtcgt acatgttgaa aggaagggt ccagtttcaa tcttctgcat     18120
ataactagcc agttacccag caccatttat taaacagtgt tttcctcatt tcctgttttt    18180
gtcaactttg tcaaatatta gttggttgca ggtatgaggc tttatttgg ggttctctgt     18240 tctgttccat tgatctatgt gtcttctttt ttaaccagta ccatactgtt ttgattcctg    18300
tagccttgta gtataatttg aagtcaggta atgtgatgcc cctgggttta ttcttttag     18360 ttaggattgc tttgactatt tgggctgttt tttgcttcca tatgaatttt acaattgttt    18420
tttctaaatc tgtgaaaaat tacattgata atttgatagg cattgcattg aatgtgtaga    18480
ttggcttggg cagtatggtc atcttaacga tattgattct tctaatccat aagcatggaa    18540 tgttttcca tttgcgttat ctgtcatttt ctttcatcag tgttttatag ttctacttat     18600
aaagatattt cacctccttt gttaaatgta ttcctaggtt tctgtgtgtg tgtgcggcta    18660
taataggcta tgttaacctg ataacaattt aactttcttg cataaaaaac tctcacttt     18720 tactccacat accgccccc caaacacatt ttaaatttt gatgtcacac ttacatcttt      18780
ttatattgca tatttcttaa caaattattg tacctagtat tatttttaat aattttatct    18840
tttaaccttc attctaaaat aaaagtgatt tgcatattac catgaaaata ttagacaggt    18900
```

```
aatgtgatgc ccctgggttt attcatttta gttaggattg ctttgccaat tgggctgttt    18960
tttgcttcca tatgaatttt acaattgttt tttctaattc tctgaaaaat tacattgata    19020
atttgatagg tattgcactg aatgtgtaga ttggcttggg cagtatggtc atcttaacaa    19080
tattgattct tctaatccat aagcatggaa tgttttttcca tttgcgttat ctgtcatttt    19140
ctttcatcag tgttttatag ttctacttat aaagatattt cacctccttt gttaaatgta    19200
ttcctaggtt tctgtgtgtg tgtgtggcta taataggcta ttttaacctg ataacaattt    19260
aagtttcttg cataaaaaac tctacacttt tactccacat actccacaca cacacacgtt    19320
ttaaattttc gatgtcacac ttacatcttt ttatattgca tatttcttaa caaattattg    19380
tacctagtat tattttttaat aattttgtct tttaaccttc attctaaaaa gtgatttgca    19440
tattaccctg aaaatattag actactttaa attggactgt gtacttactt ttactagtga    19500
gttttatact ttcatatgtt tttatgttac tcattagcct ccttttcttt cagctaaaga    19560
cctcccttta gcagttcttg taagataggt ctgttggtga ggaatggtta atttaaatat    19620
aacaaagtac aaaaagttca tcagtagagt ttcaggtttc attttttccac taacctgtaa    19680 gaatttatca tttgagtttt agtctattgt taaacagaaa tgttcacaat tatgtgaaaa    19740
gtttattaaa atattcctca ttttcctcat tatttatctg tgtgaggcca ggttttattc    19800
atttacgaaa atagcacatt ctaatagatt taattcagaa gcagttataa aaatacagtc    19860
atcttccttt aagtctgaca ttaaataaat ttgcaaaaat gtaaaacagt atcactcttc    19920
tcactctctt ttttgttgtt tgggaaagta caataatttt tatgaaaata tattatttaa    19980
caaaatcaat ttattatttt cagtttaaaa ataaggattt taaaattttt tcatttcaat    20040
ttctaatact gtaaatagtg ataggtataa cccaactaaa ccaaactctt taagattctc    20100
aaatttttaa gagtgtaaag gagtcctgaa ataaaaaagt taaacaacct agaaaaaaac    20160
aaagatataa atcagcatgt tagcattcat caattcagtt accatcattt catccctaaa    20220
agccatggca tatagttacg tctcactgag ccaccacttt gaaactccca ccctgtgcca    20280
ggtacttgtg agcatgtaac tttgttaatc aactgttcag ggctatatcc caacatggct    20340
ttgttgcact tttcgtggca cctctgctaa atctcgttag gtagaccaaa ggggtcagtt    20400
aactttttct ttatacccttt tattcatgat atttataagt ttggtaattt acaaaggtct    20460
tggacaaaga ccaggggctt atatataata atttattttat ctcttgaaga aacaaacaat    20520
ataattggtt atgaagcaca ggcgtcataa gcagaaaaca ggtttatagg taaagggggga    20580 agacctagtg tgtgtcgctt gcatcaggaa ttcatgttac catttggcaa tatgaatttg    20640
cttagcagtg tgctttttttt tctccccccc acaggatctt gctctgtccc caggctagag    20700
tacagtggcc caatctcggc tcactgcaac ctccacctcc agagttcaag tgattctcgt    20760
gcctcagact cctgagtagc taggattaca ggcgcaagcc accacaccca gctaatacag    20820 ctaattttttg tatttttagt agagacaggg tttcatcatg ttggccagac tggtctcgaa    20880
ctcctgacct caggtcatct gccaacctcg gcctcccaaa gtgctgggat tataggcatg    20940
agccactgtg cctggctgcc cttttttagta aatacatttt gcatgaccat gtggttgttt    21000
acagctattt atctagcaaa ccaataactt acagcttttt aaaggcttaa tgaatagcat    21060
ggaattattc atgatatctg tgccatatct tgaggaccca ctgtatacct gatattgcac    21120
tggactttgg aaatgaaaaa taatgagtga tcttggggaa tttacaatgt aacatagaaa    21180
ggtgtgtatc actaaatttg cacaatgaaa cataattaat aatagaagaa gtatattatc    21240
```

```
tggcagaata gagtggggaa aagtaccagc aaagacttag aataccagct ctcctcaata    21300
cttgcactta gacttggatg agaaacagtt ccccgcacag gcagatgaca gggttaggta    21360
tgataggagc cacgtaagta ggagccactc gaaatctgag tttggtgtgg ctggtgtgga    21420
gggttgaggg aatatgaaga gaggaccaca acttgaatca ctgagggccc ttttttgatc    21480
ctattagtga aatctttaaa gaaattgtat tggtgacaat aacagagaaa taagggcttt    21540
gaggatgaaa acataggctt taaaaaaaaa cttaagaaaa aaataataaa gtaagttcag    21600
tattcagtgt cctgccttaa agaaagcatt ttaggcatgc aaatatccca tatattcaga    21660
ggcttctata aaaatacaa acaaaccctg tcatatacac atgaggcaaa aaagatact    21720 ttgtgagtag aaactattga ggtaaaagaa aaacttgttt tagaagctga aggcccagct    21780
gctgacttaa taaaacaaat tatgagaatt ttgtttatgc gaaaatccat gctgttgaaa    21840
acgcgagtgt ttaaagtttt ctataaacag gaacaaggtg ttctaccaaa aaaaagtatg    21900
aaaagcacat tgaatacctg ctttgagtat ttgacttgga ggaaactacc atcactagtt    21960
gagtatacct ctttgatagc aatatgtgtt aaaagtctaa cagtctcact ctacccctcc    22020
ccgagaaggt aaaggaatat cctgacctta agggttgtga gacctagatg tttcttacca    22080
aagaactccg gtgacttttc tttgcagatt ttaaatagca aactatttta tggtggcttt    22140
aagccttcca gagcaagcag attaggtatg tagttccttt taataaaagt atttggaagt    22200
tcaataaagg caattatgat ttttctagga cctttccaa ttctgtgatt atgtgaatga    22260
ctacccggaa tttccatcaa acactgatat acaacttgct atggctacaa tttattttgg    22320
tgtgaaaaca tgtttgcttt tctgttctta tgtctcccett catacaaaag tataatatcc    22380
cagatatgta ggcatatagt tctgccattc agagtaattc taatatactt taatcttatt    22440
aactatctgg aagactaatg cacagttata gctgcatttc tttaagcaag tctatcatat    22500
ctttgggttt ataccaaact aaatttgtga actattatcc atttacaaaa tgattattta    22560
catcaatctt cctttaaata acaaatgctc acaatgcatt ttaaaatatt acctacttta    22620
taaaaatcca ttctgaataa aaatgggaga ataccctgtag tgttcattgc attgagttgt    22680
tgactctttg gccaatatgc gtttatattt tgtcttgaaa gatggaccct atattgacaa    22740
catcagttcc agtgtactca ttgaaagtgg ataaggaata tgaagtgcgt gtgagatcca    22800
aacaacgaaa ctctggaaat tatggcgagt tcagtgaggt gctctatgta acacttcctc    22860
agatgagcca atttacatgt gaagaaggta aagaaataa aagattaaaa tagtagctaa    22920
cctggctttt gtcaatataa cagttgattc accccctgcac tggtagtgtg ttgtccaaat    22980
caaaatatat taacatcaga tatcaggatg agagaccttg agctcactat ctgtaacaga    23040
tattgttcat tgcaaaagca gaaggaagat ttagtttcca aattttttcat tcaggagaag    23100 tccgggggc aggtggaagt ttagagacag gaatttggtg gcaatctcca gatggtagaa    23160
ttcagatgat tcttttcttt atatattttt atatttctga aattttctat agtaagtttg    23220
ttttgaattt ataatcagga aaaaagctg tactgatggt tagggaagaa agtatgtatc    23280
tatatggatg gatagatatg tggcatctaa gaggaaaccc aatattgagt cagcataggt    23340
agtcaacagc agatgcatac ggttttagaa agcggaggtg tggctttac ctagaggaat    23400 gcctaataag tagtgtggca gtcatactta aaggagacgg ggaacatttg aaaaccctat    23460
gtaggagaat cacaacaatg attaaagttt ttaaaaatgg gacctatgaa tttagaataa    23520
aagaattaaa acttttagat acagaaataa agaaaactga ttaataatga gcagaaagta    23580
tagagtatta ttattctcaa atgggaaatg gctctattcc atcttcattg aaaacagaag    23640
```

```
tttacagggc tatatgtttg ttaatgaaac aaccacaagc tacatagaaa ataaatttat    23700
atttctgtat ttactataca ggtagaatct catgatacta aatagcatta ggatgaaaat    23760
ttctatagca ccattttctc tatactctag ttaactgaat tcttgtttcc aaactatttg    23820
atattatgca attctggcct taaaagtaca atagctatac acccttaagc ttagtgtagt    23880
ggcatttaat tcacttaaca tatatatata tattttttt ttttttttt ttttttttt    23940 tttttgagac ggagtctcgc tctgtcgccc aggctggagt gcagtggcgg gatctcggct    24000
cactgcaagc tccgcctccc gggttcacgc cattctcctg cctcagcctc caagtagct    24060 gggactacag gcgcccgcca ctacgcccgg ctaattttt gtatttttag tagagacggg    24120
gtttcaccgt tttagccagg atggtctcga tctcctgacc tcgtgatccg cccgcctcgg    24180
cctcccaaag tgctgggatt acaggcaaca tatatttttt aaactgcctt ttccttctgt    24240
tactaacaaa aaagaagctc taactttatg ttattttcct gaatatgtca ttgatatgaa    24300
attatagaca ctacaagaca aaaatgatt ttttctcccc caccaattct ttaaaatgct    24360
tataatatct ccctagggga ttttaataac tttttaaata agaaaagact atttcagcat    24420
aaagacctac attttaaatg gcaatgttaa ggtaaatttc atctgtcatt tttataaaaa    24480
agtggttagc ctctgcctct gtggtaagaa tactgggtac caactgcaaa gtagctggca    24540
ggtactcaat cttaaggaat gaaatagaag ttttacaaac aggttccccc aagtctcata    24600
caaagtatac taaaacctga agatgggagc ctcagtagtg atctttctgt caattttatg    24660
tatataatat acatgagata tatttattat attttaataa tttaatttat tgatataaat    24720 acgtatttt atagctgtaa aatatatgtt atttgtgtct aagaagtttc tgtcatgatt    24780
tatcaataaa aactctgcct tcatctttt gataaatctt caatctggaa actaagaaaa    24840
tcaccacact taaaaaaaaa tagaaaagaa accgagtggg cattatttag gtagtgtgtt    24900
aataagcaac acttttttac tgaagctgaa acctttatga tactccctgg acacatagta    24960
tgcttaaagc agattgtttg ttttcataaa acacacattg attttgaact atatgctgtt    25020
tctttatttt gaagtttttt tttaatgtga ggagatttga aaagtggaca gagatgttca    25080
taaaacagaa aaaaactaag tcgttgcatt ctgtttcagt ggttatcaag agaaatcact    25140
gactttatta gatgaataca aattatgaat ttttgtgaa aagggaaagg gaaatgtaaa    25200
ctgtgcttca actattcgta attctgaaaa cgaaatattc ttgtgtgttt cagatttcta    25260 cttccatgg ctcttaatta ttatctttgg aatatttggg ctaacagtga tgctatttgt    25320
attcttattt tctaaacagc aaaggtaggt gtggagtagt attctttggt attttgtacc    25380
agttgtttag atttccatat gtgtttctat ttgttatttg atattttctt tgtcaaatta    25440
tgagtggaaa ttttagttaa cctagtacac ttttatctcc agttatatat ttaccattca    25500
tataaaactc aatttgttgt atttatctta gacaatttag aggtttagat tctatctgga    25560
gacttgtaca ggacattaag aggcttaggc tggtgactat gcataccttg tgatatgtac    25620
ctctttatcc aagagctagc tctttccctc aagtcctcaa caagttgacc cattcattcc    25680
aggacttcaa agtatcactg agcctttggc tgagtctgat acagtcctta tatacagaca    25740
attttttttt ttccttgaga cggtgtctta ctctgttgcc caggctggag tgcaatggcg    25800
caatcttggc tcactgcaac cgccgccccc caggttcaag caattctcct gcctcagcct    25860
ccagagtagc tgggattaca ggcatgcgcc accaagccca gctaattttg tattttaga    25920 tacagtttca ccatgttggt cagactggtc tcgaactcct gacctcaggt gatctgccca    25980
```

```
cctcagcctc ccaaagcgct gggattacag gcgtgagcta ccgcgcctgg ccccatttaa    26040
ggtattttta aagtcccaat ggttaatctt gttgcttctc ctagaattaa ggtgactaac    26100
actcccaggt tgcctagaac tctcctggtt tttagcaatg caagtccggt gtgccaggaa    26160
atccctcagt tccaggtaac caagacagtt gatcccctta cctagaattg aaaatacgtt    26220
ctccagctga agccaagagg catctataaa tcaaaatgag atctatgtta atatatttta    26280
aaagatttta ctttgttttg taaggtagta tagcacttgt aaacttcaaa acagaatttt    26340
gttaggaaga agaattattg ggacgctaga tttctatagt gtcaagcatg ctaaaagtct    26400
aactgaatgc agaaagggtt atttttcagta gagcttcatg tccaatttta taatataaac    26460
caattggaaa gtaaaattca ttctgaattc cattttgcac ctaactttct ggcaacattc    26520
ctgttttcca aaaagcagc tatcataaat cacaacacaa ttttctattg tttcaggaaa    26580
ataaataaat atatttttag aattttaatt tgtgtattta agtaatgcca acaacaaaaa    26640
agccaaatta ttctgttgat taatttcagt ttattaatct atatatttgg tgggaaaatt    26700
tatacataac ttcagtagat aaactcacga ggtatgtaaa gtaattagct cttagtatta    26760
gctgtgaatt tctagccatt gtgaaggcca agtcaatttg ttatgttgtt tagttatatt    26820
agttaacaat attaggaaga aaaaattatc ctctcaaaaa ataggatttc caagaaaaca    26880
tattacttct aatacagtgc tttttataaa taatgaaatg cttaactata atgtttagtc    26940
aaaatcacca aattctacaa ttgatttgaa atctttattg ttctcccaaa tttcctgcac    27000
taaattgaat tttctgtagg aaagaattaa ctttattttt atttgcccat taaaaacgct    27060
tatcattgtc taaatttgca tgttctactg aaagtgggaa atagtagcaa atatttgtca    27120
gcaagtatgg acagaacatg tagttccaac aattaaattg atactgcaaa gaacgagatt    27180
tttcctagaa ctgtagggct gtaaagtggc gtcaggtcct acatgccttt gaaattttct    27240
gagtccacaa ttcattatcc aacccacttc accctgcttt aatccagtta attgagtcaa    27300
ctctagcaaa atttataatt ttatttgtat ctgatacaaa accacaaaca tagtttcaag    27360
tcaggctatt attatactgg ttcctaccac acaaccctcc cagcctttga gctgttacca    27420
attgaggaaa gaaataactg aatcagccta aaatagaatt tccaaaccag tagcgaaatt    27480
cagcctacag attcatattt tgttatttta ttttaattag ttttgatttc agagtgaaga    27540
ttttcctaca aagtgtttgt aaaatagaga attttcacac aaaaatccag atttggggat    27600 tatctttttaa aaaatgaaag atgtagtgaa actaaacaag gcagcatatg ctgcagcaga    27660
caaccagcta tcctatttgg gattggctca cattctttaa tttgccacca tcctcattcc    27720
tcctaatgac tttgcaactg gcttgcttta ttcctctgca tgacctgctt gggcctctta    27780
gatttatgct ctgccactgt ggcataaggt cactacaacc actagaaaac cactagcgca    27840
tgcctgaatg catcatccta tttaaaaagg aaaagcacac gtcacaaagt caaacatcag    27900
ccatttggaa acctttgctt cctgtaatta gaattatgtt ccatctttt atgttttgg    27960 gaatttgaaa taccaatttc gagatgcaga atcaaaaaaa aaaacaaaa cagcgaaaca    28020 gcagcatgac acaaagaacc tgggttttga tttggagtca ggttctctgg gtttgagccc    28080
caactgtgcc aactatgaat gcatgatttg aacatgttgc ttaattttcc aagttttgc    28140 acagatatat catctgcctc cctgggagtc ataaggatta agtgaaatgt ttagtgcagg    28200
ggtcacaaac ttatttcata gagttagagt acatttttag gcttttcaag ccatacagtc    28260
tctatcacag ctactcaact ctgccactgt agcacgaaag tggccataaa caaaatggaa    28320
atgaatgaag atgcttgtgt tctcataaaa ttttatctac acaaacatgt gacaggccag    28380
```

```
atttggccca cagaccttaa tttagtgaac catagtttag tgcaaagtat atcccacagt   28440
gtctgattta tcagaagcac taaaaaatga tagtagttat tattaataat ttgtattact   28500
tatttctata tctgtaattc atcagtaaca atatgcttta acatttgccc cactgagtag   28560
tagaggctac ttaatgcaat ttataaaatg gattttttgct tattacttgg attaggtaaa   28620
atagcaagtg gaaatactga gaaaatgtac tccttatgga atggactgga ctgaccattc   28680
acactgagtg gaatagtaac tgatatccaa aaatctggtt accacctctt catgacagtg   28740
tcatctctga atagtcagga gttttttaaa aaattaaatg aattgtttgg aataatctct   28800
gagccttttt ccagtgctat aatttgattt taaaaaataa actccaggcc agatacaatg   28860
gcttatagca tataaatcca gcactttggg aggatgggc gggagtattg ccctgaggcc   28920
aggagttcca gacagctcgg gcaatgacta gagcaagact ccattacaaa aaatgaaaca   28980
acaaaaatta gcacaccctg tagtcctagc tacttaggag gctgaggcaa gaatatcgct   29040
tggcccagga gtttgaggct gcagtgaatt atgattgcac cactggactc cagtgtgggc   29100
aatgaagtaa gaccctgtct caaaaagttt taaaaaaaat taaaaacacc ataaattcca   29160
attacactat taattgtaca aaatagatac atgatttatt cattttttatg accaaaaaat   29220
aatttaaaga tttggaacaa aaaatgtaaa tgcatcctag aattgtatat ataaacccat   29280
actgattagt tagagatagt taaaatttaa tctgtcccat ctgaaatgaa ccctgtagta   29340
aaaccctggt taataagatc atcttagata atttcataat taatatgaac tatatggcta   29400
acctacccaa gtctacccctt tttcaagggt gtaagtaatc ttggctccat gtggattgac   29460
tcttttttct ttctttcctg tacaaattac tgatgagatg tacactagaa ttgccttata   29520
gctgaaatgg aaatcagctt tagatgaaat taaatttctt tctttcaaat actaaatctg   29580
gctgaaaata aaaagcatta agaaaaaaac aattgtggga aaaccacatt ttcttttaat   29640
agacttcaga tgaggctttt tgggtttttt agttgttctt ttttttcctt ctacagtttt   29700
tctttctcat ttactgtcta atattttctt ctgtttctca cactccaatt atataaagta   29760
ccagaatatt tggaaaaagt aatagtattg ccaatatttt atttctatct tttgctataa   29820
ttgagaatat gtagctttta agatgtcaaa accaaaattt tatatgtttt caaggattaa   29880
aatgctgatt ctgcccccag ttccagttcc aaagattaaa ggaatcgatc cagatctcct   29940
caaggtaact aataaatttta tctaaattgt agctagtact aattaacacc tgaagactcc   30000
tgtcatatgt tgaaggtttt ctgtaagcta tatatcac attcaattttt cttgtatctc   30060
ttctcctaga gaaattttt ttaaatattc tatttcttaa aaataagaaa acgtcatatg   30120
tatttaaaaa gttacacact aatttatgtt tttttttatat gttttgttac tgttgttctt   30180
attgtaacca taattaatct ctgaacatta tttgctaatt catttaatta ttatgagttt   30240
cttttcatag atcttcattt tcttttctatt ttctaggaag gaaaattaga ggaggtgaac   30300
acaatcttag ccattcatga tagctataaa cccgaattcc acagtgatga ctcttgggtt   30360
gaatttattg agctagatat tgatgagcca gatgaaaaga ctgaggaatc agacacagac   30420
agacttctaa gcagtgacca tgagaaatca catagtaacc tagggtgaa ggatggcgac   30480
tctggacgta ccagctgttg tgaacctgac attctggaga ctgatttcaa tgccaatgac   30540
atacatgagg gtacctcaga ggttgctcag ccacagaggt taaaagggga agcagatctc   30600
ttatgccttg accagaagaa tcaaaataac tcaccttatc atgatgcttg ccctgctact   30660
cagcagccca gtgttatcca agcagagaaa aacaaaccac aacccacttcc tactgaagga   30720
```

```
gctgagtcaa ctcaccaagc tgcccatatt cagctaagca atccaagttc actgtcaaac   30780
atcgactttt atgcccaggt gagcgacatt acaccagcag gtagtgtggt cctttccccg   30840
ggccaaaaga ataaggcagg gatgtcccaa tgtgacatgc acccggaaat ggtctcactc   30900
tgccaagaaa acttccttat ggacaatgcc tacttctgtg aggcagatgc caaaaagtgc   30960
atccctgtgg ctcctcacat caaggttgaa tcacacatac agccaagctt aaaccaagag   31020
gacatttaca tcaccacaga aagccttacc actgctgctg ggaggcctgg gacaggagaa   31080
catgttccag gttctgagat gcctgtccca gactatacct ccattcatat agtacagtcc   31140
ccacagggcc tcatactcaa tgcgactgcc ttgcccttgc ctgacaaaga gtttctctca   31200
tcatgtggct atgtgagcac agaccaactg aacaaaatca tgccttagcc tttctttggt   31260
ttcccaagag ctacgtattt aatagcaaag aattgactgg ggcaataacg tttaagccaa   31320
aacaatgttt aaaccttttt tgggggagtg acaggatggg gtatggattc taaaatgcct   31380
tttcccaaaa tgttgaaata tgatgttaaa aaataagaa gaatgcttaa tcagatagat   31440
attcctattg tgcaatgtaa atattttaaa gaattgtgtc agactgttta gtagcagtga   31500
ttgtcttaat attgtgggtg ttaatttttg atactaagca ttgaatggct atgttttaa   31560 tgtatagtaa atcacgcttt ttgaaaaagc gaaaaaatca ggtggctttt gcggttcagg   31620
aaaattgaat gcaaaccata gcacaggcta attttttgtt gtttcttaaa taagaaactt   31680
ttttatttaa aaaactaaaa actagaggtg agaaatttaa actataagca agaaggcaaa   31740
aatagtttgg atatgtaaaa catttatttt gacataaagt tgataaagat attttttaata   31800 atttagactt caagcatggc tattttatat tacactacac actgtgtact gcagttggta   31860 tgaccctct aaggagtgta gcaactcag tctaaagctg gtttaatgtt ttggccaatg   31920 caccctaaaga aaaacaaact cgttttttac aaagcccttt tatacctccc cagactcctt   31980
caacaattct aaaatgattg tagtaatctg cattattgga atataattgt tttatctgaa   32040
tttttaaaca agtatttgtt aatttagaaa actttaaagc gtttgcacag atcaacttac   32100
caggcaccaa aagaagtaaa agcaaaaaag aaaacctttc ttcaccaaat cttggttgat   32160
gccaaaaaaa aatacatgct aagagaagta gaaatcatag ctggttcaca ctgaccaaga   32220
tacttaagtg ctgcaattgc acgcggagtg agtttttag tgcgtgcaga tggtgagaga   32280
taagatctat agcctctgca gcggaatctg ttcacaccca acttggtttt gctacataat   32340
tatccaggaa gggaataagg tacaagaagc attttgtaag ttgaagcaaa tcgaatgaaa   32400
ttaactgggt aatgaaacaa agagttcaag aaataagttt ttgtttcaca gcctataacc   32460
agacacatac tcattttca tgataatgaa cagaacatag acagaagaaa caaggttttc   32520
agtccccaca gataactgaa aattatttaa accgctaaaa gaaactttct ttctcactaa   32580
atcttttata ggatttattt aaaatagcaa aagaagaagt ttcatcattt tttacttcct   32640
ctctgagtgg actggcctca aagcaagcat tcagaagaaa aagaagcaac ctcagtaatt   32700
tagaaatcat tttgcaatcc cttaatatcc taaacatcat tcattttgt tgttgttgtt   32760 gttgagacag agtctcgctc tgtcgccagg ctagagtgca gtggcgcgat cttgactcac   32820
tgcaatctcc acctcccaca ggttcaggcg attcccgtgc ctcagcctcc tgagtagctg   32880
ggactacagg cacgcaccac catgccaggc taatttttt gtattttagc agagacgggg   32940
tttcaccatg ttggccagga tggtctcgat ctcctgacct cgtgatccac ccgactcggc   33000
ctcccaaagt gctgggatta caggtgtaag ccaccatgcc cagccctaaa catcattctt   33060
gagagcattg ggatatctcc tgaaaaggtt tatgaaaaag aagaatctca tctcagtgaa   33120
```

```
gaatacttct cattttttaa aaaagcttaa aactttgaag ttagctttaa cttaaatagt    33180
atttcccatt tatcgcagac cttttttagg aagcaagctt aatggctgat aattttaaat    33240
tctctctctt gcaggaagga ctatgaaaag ctagaattga gtgtttaaag ttcaacatgt    33300
tatttgtaat agatgtttga tagattttct gctactttgc tgctatggtt ttctccaaga    33360
gctacataat ttagtttcat ataaagtatc atcagtgtag aacctaattc aattcaaagc    33420
tgtgtgtttg gaagactatc ttactatttc acaacagcct gacaacattt ctatagccaa    33480
aaatagctaa atacctcaat cagtctcaga atgtcatttt ggtactttgg tggccacata    33540
agccattatt cactagtatg actagttgtg tctggcagtt tatatttaac tctctttatg    33600
tctgtggatt ttttccttca aagtttaata aatttatttt cttggattcc tgatagtgtg    33660
cttctgttat caaacaccaa cataaaaatg atctaaacca ctctgtatac tgtgaattat    33720
cattgtaagg agagcttagc accactggat caaatacatc agcattgggt atggagattt    33780
ttatgtgctg agatatagag agggaaacat atccccttc ccttattttt tgagaagaca     33840
aaagcccaac tcagaaatat cccactggct tggccctccc cttaggctgt gactccccat    33900
aggcaaaggt tcatagagct gtgtatttga tgcatcatgg aaaataaatg acatgggtgt    33960
tggatgaggg agagtgatat gtgagcatta tctttacatt tccagcttga gcatgttgtc    34020
tggaaggaag gaaagcagct cttcctctgc cattcaccca ttggcctaag tcagtttatt    34080
ggactagctg cttgttatc                                                 34099

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
tcagggcatt ctttccattc                                                  20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cataatcagg gcattctttc                                                  20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
cctttaatct ttggaactgg                                                  20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 22
tcatcaatat ctagctcaat                                               20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
cttagaagtc tgtctgtgtc                                               20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
cctgctggtg taatgtcgct                                               20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
atgtaaatgt cctcttggtt                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tggtgatgta aatgtcctct                                               20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ttctgtggtg atgtaaatgt                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
aggctttctg tggtgatgta                                               20

<210> SEQ ID NO 29
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 29
tggtaaggct ttctgtggtg                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
agttggtctg tgctcacata                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tgttcagttg gtctgtgctc                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gcatgatttt gttcagttgg                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33 tataaaggg ctttgtaaaa                                                20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
catagcagca aagtagcaga                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
```

-continued gctattttg gctatagaaa　　　　　　　　　　　　　　　　　　　　20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gattgaggta tttagctatt　　　　　　　　　　　　　　　　　　　　20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gatccatacc tgtaggacct　　　　　　　　　　　　　　　　　　　　20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ccagagatcc atacctgtag　　　　　　　　　　　　　　　　　　　　20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tgctaaggat agctgctgtg　　　　　　　　　　　　　　　　　　　　20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ttgtctttag gcctggatta　　　　　　　　　　　　　　　　　　　　20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ttagaagaat ttgtctttag　　　　　　　　　　　　　　　　　　　　20

<210> SEQ ID NO 42
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 42
gtgaatttag gctccttaga                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gctgtatggg tcctaggttc                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
taacagctgt tttccccagc                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tttcatccac tgtaccacca                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ttgcactatt tcatcaacag                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gggtggatct ggttgcacta                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
attgcgtggt gcttcccatc                                               20
```

```
<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
tagggtccat cattttccat                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
caatgagtac actggaactg                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
aactcgccat aatttccaga                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
agcccaaata ttccaaagat                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tcagcatttt aatcctttgc                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
attttccttc cttgaggaga                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 55
agattgtgtt cacctcctct                                                     20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
aacccaagag tcatcactgt                                                     20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ctggctcatc aatatctagc                                                     20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tgtgtctgat tcctcagtct                                                     20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tatgtcattg gcattgaaat                                                     20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
aaggcataag agatctgctt                                                     20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
actcagctcc ttcagtagga                                                     20

<210> SEQ ID NO 62

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
ggacatccct gccttattct                                                   20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ggcattgtcc ataaggaagt                                                   20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64 acttttggc atctgcctca                                                    20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
gatgcacttt ttggcatctg                                                   20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
cagtcgcatt gagtatgagg                                                   20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ctctttgtca ggcaagggca                                                   20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
```
gtgctcacat agccacatga                                         20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
aagaaaggct aaggcatgat                                         20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
aaatacgtag ctcttgggaa                                         20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
caatcactgc tactaaacag                                         20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
aaacatagcc attcaatgct                                         20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
gtgctatggt ttgcattcaa                                         20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
gttttacata tccaaactat                                         20

<210> SEQ ID NO 75
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 75
catcaaccaa gatttggtga                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gaggctatag atcttatctc                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tagtgagaaa gaaagtttct                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
aatgctctca agaatgatgt                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
acactcaatt ctagcttttc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
catctattac aaataacatg                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
ctcttggaga aaaccatagc                                              20
```

```
<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tctacactga tgatacttta                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
cacagctttg aattgaatta                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
agtcttccaa acacacagct                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
aggctgttgt gaaatagtaa                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
atagaaatgt tgtcaggctg                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ccaaaatgac attctgagac                                               20

<210> SEQ ID NO 88
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 88
ataatggctt atgtggccac                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
agttatgtga ccctgattga                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
ttgagtgttc ctaaaatgaa                                               20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
atggaggctg gaggttcaaa                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
tagggtccat ctttcaagac                                               20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
tctccagata gaatctaaac                                               20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tccaaatatt ctggtacttt                                               20
```

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tattagttac cttgaggaga                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
attttccttc ctagaaaata                                              20

<210> SEQ ID NO 97
<211> LENGTH: 1170
<212> TYPE: DNA
<213> ORGANISM: M. musculus
<220> FEATURE:

<400> SEQUENCE: 97
gagcaaggac tgtggaagct gctgctgctg tctgaagcga gctcctggtt gggtgtgatg    60
gcctgaggga ctccggaggg tgggttgtga agcacgcgac ccccgcagcg ctctgccttt   120
gcgcagtctg tgcaggctgc agctgcaagc tggaagcaga ggagctggag tcagagtcac   180
cgacgccaga gcctccatga actggggtct caggtatgga tctttgtcag gtcttcttaa   240
ccttggcact ggcagtcacc agcagcacat tttctggaag tgaggctaca ccagctactc   300
ttggcaaagc ttccccagtt ctgcaaagaa tcaatccaag cctggggaca agttcttctg   360
gaaagcctcg attcaccaag tgtcgttccc ctgaactgga gacattttca tgctactgga   420
cagaaggaga taatcctgat ttaaagaccc caggatctat tcagctgtac tatgctaaaa   480
gggaaagcca acgacaagct gcaagaattg ctcatgaatg gacccaggaa tggaaagaat   540
gccctgatta tgtctctgct ggaaaaaaca gctgttactt caactcatca tatacctcca   600
tttggatacc ctactgcatc aagctaacta caaatggtga tttgctggac caaaaatgtt   660
tcactgttga cgaaatagtg caacctgatc cacccattgg cctcaactgg actttactaa   720
acattagttt gaccgggatt cgtggagaca tccaagtgag ttgcaaccaa ccacccaatg   780
cagatgttct gaagggatgg ataattctgg agtatgaaat tcagtacaaa gaagtaaatg   840
aatcaaaatg gaaagtgatg ggccctatat ggttaacata ctgtccagtg tactcattga   900
gaatggataa agaacatgaa gtgcgggtga gatccagaca acggagcttt gaaaagtaca   960
gcgagttcag cgaagtcctc cgtgtaatat tcctcagac gaacatattg gaagcatgtg   1020
aagaaggaac caagtccaat tctcagcacc cacatcaaga gattgacaac cacctgtatc   1080
accagcttca gaggatccgc catccctagc cttgtgggca cctgcattca tatgcacata   1140
catgcatacg cataattcaa aataataaaa                                    1170

<210> SEQ ID NO 98
<211> LENGTH: 3976
<212> TYPE: DNA
<213> ORGANISM: M. musculus
<220> FEATURE:
<221> NAME/KEY: unsure

```
<222> LOCATION: 2438
<223> OTHER INFORMATION: unknown
<220> FEATURE:
<221> NAME/KEY: unsure
<222> LOCATION: 2468
<223> OTHER INFORMATION: unknown
<220> FEATURE:
<221> NAME/KEY: unsure
<222> LOCATION: 2561
<223> OTHER INFORMATION: unknown
<220> FEATURE:
<221> NAME/KEY: unsure
<222> LOCATION: 2591
<223> OTHER INFORMATION: unknown
<220> FEATURE:
<221> NAME/KEY: unsure
<222> LOCATION: 3128
<223> OTHER INFORMATION: unknown
<220> FEATURE:
<221> NAME/KEY: unsure
<222> LOCATION: 3154
<223> OTHER INFORMATION: unknown
<220> FEATURE:
<221> NAME/KEY: unsure
<222> LOCATION: 3305
<223> OTHER INFORMATION: unknown
<220> FEATURE:
<221> NAME/KEY: unsure
<222> LOCATION: 3468
<223> OTHER INFORMATION: unknown
<221> NAME/KEY: unsure
<222> LOCATION: 3470
<223> OTHER INFORMATION: unknown
<223> OTHER INFORMATION:

<400> SEQUENCE: 98
atagaactgc agagtcttga gagctgcgcg gggtctcagg tatggatctt tgtcaggtct      60
tcttaacctt ggcactggca gtcaccagca gcacattttc tggaagtgag gctacaccag    120
ctactcttgg caaagcttcc ccagttctgc aaagaatcaa tccaagcctg gggacaagtt    180
cttctggaaa gcctcgattc accaagtgtc gttccsctga actggagaca ttttcatgct    240
actggacaga aggagataat cctgatttaa agaccccagg atctattcag ctgtactatg    300
ctaaaaggga aagccaacga caagctgcaa gaattgctca tgaatggacc caggaatgga    360
aagaatgccc tgattatgtc tctgctggaa aaaacagctg ttacttcaac tcatcatata    420
cctccatttg atacctac tgcatcaagc taactacaaa tggtgatttg ctggaccaaa    480
aatgtttcac tgttgacgaa atagtgcaac ctgatccacc cattggcctc aactggactt    540
tactaaacat tagtttgacc gggattcgtg gagacatcca agtgagttgg caaccaccac    600
ccaatgcaga tgttctgaag ggatggataa ttctggagta tgaaattcag tacaaagaag    660
taaatgaatc aaaatggaaa gtgatgggcc tatatggtt aacatactgt ccagtgtact    720
cattgagaat ggataaagaa catgaagtgc gggtgagatc cagacaacgg agctttgaaa    780
agtacagcga gttcagcgaa gtcctccgtg taatatttcc tcagcgaac atattggaag    840 catgtgaaga agatatccag tttccatggt tcttaattat tatctttgga atatttggag    900
tagcagtgat gctatttgta gttatatttt caaagcagca aaggattaag atgctgattt    960
tacccccagt cccagttcca aagattaaag ggattgatcc agatcttctc aagggaggga   1020
agttggagga ggtgaacacc atcttaggca ttcatgataa ctacaaaccc gacttctaca   1080
atgatgattc ctgggtcgag ttcattgagc tagatattga tgaagcagat gtggatgaga   1140
agactgaagg gtctgacaca gacagacttc taagcaatga tcatgagaaa tcagctggta   1200
tccttggagc aaaggatgat gattctgggc gtaccagctg ttacgaccct gacattttgg   1260
```

```
atactgattt ccataccagt gacatgtgtg atggtacctt gaagtttgct cagtcacaga    1320
agttaaatat ggaagctgat ctcttgtgcc ttgatcagaa gaatctgaag aacttgcctt    1380
atgatgcttc ccttggctct ctgcatccct ccattaccca gacagtagaa gaaaacaagc    1440
cacagccact tttgagcagc gaaactgagg caacccacca actcgcctct acaccgatga    1500
gtaatcccac atcactggca aacattgact tttatgccca agtaagcgac attacaccag    1560
caggtggtga tgtcctttcc ccaggccaaa agattaaggc agggatagcc caaggcaata    1620
cccagcggga ggtggccacg ccctgccaag aaaattacag catgaacagt gcctactttt    1680
gtgagtcaga tgccaaaaaa tgcatcgctg tgcccgtcg catggaagcc acgtcttgta    1740
taaaaccaag ctttaaccaa gaggacattt acatcaccac agaaagcctt accactactg    1800
cccagatgtc tgagacagca gatattgctc cagatgctga gatgtctgtc ccagactaca    1860
ccacggttca caccgtgcag tctccaaggg gccttatact caacgcaact gctttgcctt    1920
tgcctgacaa aaagaatttt ccctcctcgt gtggttatgt gagcacagac caactgaaca    1980
aaatcatgca gtagcctttc ctatctttaa atggcaaggg aaaggctggg cacaaacgct    2040
taaaccaaaa ctatgtttta aatctgtgtt gggagagcat gagagtggat atggattcta    2100
aaatactttt tctggaaatg tcaaaatatc aataagtgga aaatcaagaa ttcgtaatca    2160
gataaatgct cccattgtga attataaata ttttaatgaa ttgtctttaa gactgtatag    2220
tggcagtgat tgtctgtact gtgggtctta attttgtgat actaagcatt aaatagctac    2280
gttttttatg tatgtagatc atgcttttgg aaaaagcaaa acaatcaggt ggcttttgca    2340
gttcaggaaa ttgaatgcag attatagcac aggctgattt tttttttctt ttttaaataa    2400
ctgggaacta aaactctagg tgagaaggta aaactagntt ggatatgcaa aacatttatt    2460
ttgacatnaa attgataaag atattttaa taatttacac tttaagcatg agkmctttat    2520
aatatgctac acacatattg tagttcagaa caatccatct naggatgtag cagctacagt    2580
gtaaagaggg nttcatgttt tggtcaatga acgtaaagaa aaccaaacaa gttagatttt    2640
tacaaagccc ttttataact tccaaaactt cttaactcta aaaatgtcta ataacctgca    2700
ttattagaaa aaaacatttt aaatttgtaa acgaatattt ttttaatttt gaaaacttta    2760
ttttttttta atgttgaatc aacgtatcat acaccaaaca gtaaacagaa attataataa    2820
tggaagaagt gctttcttcg acaaatttcc attcaagcca cacagctaca tgtaagagaa    2880
gtagaagtga tgtggtgtga ttggctagga tgcagaagag cttcaggaat acaagaagtg    2940
agagcccaag gattgggagg aggggggctct cacatctcca cagtgcagtc tgtcaaaccc    3000
agcttggttt ttatagtatt ctaagaatta ttgtgtacaa ggaaaagtct cacatgtatg    3060
aaatccagta tccagatggg gtaaagttag cagataatag gataggaaat taaagaccta    3120
gatctagnac tagtggactt ttttcacaga cagnacacaa attttttaatt cagggagaag    3180 ggacagaata aatgacttcc cactcacaaa gcacaactca gaagtaatta aacaggtaac    3240
agaaaccttg ccatcaaacc tttgataaga tgtattttaa gtagtaagca gtatttcaat    3300
gcttnttact taccctccca ggacaaccga tctcaaataa gggagataag gtagataaaa    3360 atcactttt gattctgtaa taacataaac atagttcttt gggttagcac ccccccaaaa    3420
aaaaatttat gggagaaaga ggactctcag ctgactgaag aatacatntn atttaaatat    3480
tttttagatg cctgaaactt taaaattacc tttaagtttt aatggattac cattttgcca    3540
agacctttgt ggggaaacaa gcttaatgtt tagtgatttt gaaatctctt tcatgcagga    3600
gagacagtga aaatctagcc ttgggtgttt aaggttcgcc ttgttacttt gtaatagatt    3660
```

```
ttaataagtt tttctgctac tttgctgcta tggttctcc  aatggctaca  tgatttagtt   3720
catatgaagt atcatcaact tagaatctat tcagcttaaa gatgtgtgtt ttgatgaact   3780
atcttaccat ttcaccatag gctgaccacg tttctatagc caaaaatagc taaataccct   3840
aatcagttcc agaatgtcat tttttggtac tttgctggcc acacaagccg ttattcaccg   3900
tttaactagt tgtgttctgc agtctatatt taactttctt tatgtctgtg gattttccc    3960 ttcaaagttc aataaa                                                   3976
```

```
<210> SEQ ID NO 99
<211> LENGTH: 4014
<212> TYPE: DNA
<213> ORGANISM: M. musculus
<220> FEATURE:
<221> NAME/KEY: unsure
<222> LOCATION: 2476
<223> OTHER INFORMATION: unknown
<220> FEATURE:
<221> NAME/KEY: unsure
<222> LOCATION: 2506
<223> OTHER INFORMATION: unknown
<220> FEATURE:
<221> NAME/KEY: unsure
<222> LOCATION: 2599
<223> OTHER INFORMATION: unknown
<220> FEATURE:
<221> NAME/KEY: unsure
<222> LOCATION: 2629
<223> OTHER INFORMATION: unknown
<220> FEATURE:
<221> NAME/KEY: unsure
<222> LOCATION: 3166
<223> OTHER INFORMATION: unknown
<220> FEATURE:
<221> NAME/KEY: unsure
<222> LOCATION: 3192
<223> OTHER INFORMATION: unknown
<220> FEATURE:
<221> NAME/KEY: unsure
<222> LOCATION: 3343
<223> OTHER INFORMATION: unknown
<220> FEATURE:
<221> NAME/KEY: unsure
<222> LOCATION: 3506
<223> OTHER INFORMATION: unknown
<221> NAME/KEY: unsure
<222> LOCATION: 3508
<223> OTHER INFORMATION: unknown
<223> OTHER INFORMATION:

<400> SEQUENCE: 99
acgtctggag agagagaggg agagagctgg ctgcaagcag tggttgtaac atgggactat    60
ccgcttgtgg gtctcaggta tggatctttg tcaggtcttc ttaaccttgg cactggcagt   120
caccagcagc acattttctg gaagtgaggc tacaccagct actcttggca aagcttcccc   180
agttctgcaa agaatcaatc caagcctggg acaagttct  tctggaaagc ctcgattcac   240
caagtgtcgt tcccctgaac tggagacatt ttcatgctac tggacagaag gagataatcc   300
tgatttaaag accccaggat ctattcagct gtactatgct aaaagggaaa gccaacgaca   360
agctgcaaga attgctcatg aatggaccca ggaatggaaa gaatgccctg attatgtctc   420
tgctggaaaa aacagctgtt acttcaactc atcatatacc tccatttgga taccctactg   480
catcaagcta actacaaatg gtgatttgct ggaccaaaaa tgtttcactg ttgacgaaat   540
agtgcaacct gatccaccca ttggcctcaa ctggacttta ctaaacatta gtttgaccgg   600
gattcgtgga gacatccaag tgagttggca accaccaccc aatgcagatg ttctgaaggg   660
```

```
atggataatt ctggagtatg aaattcagta caaagaagta aatgaatcaa aatggaaagt    720
gatgggccct atatggttaa catactgtcc agtgtactca ttgagaatgg ataaagaaca    780
tgaagtgcgg gtgagatcca gacaacggag ctttgaaaag tacagcgagt tcagcgaagt    840
cctccgtgta atatttcctc agacgaacat attggaagca tgtgaagaag atatccagtt    900
tccatggttc ttaattatta tctttggaat atttggagta gcagtgatgc tatttgtagt    960
tatattttca aagcagcaaa ggattaagat gctgatttta cccccagtcc cagttccaaa   1020
gattaaaggg attgatccag atcttctcaa gggagggaag ttggaggagg tgaacaccat   1080
cttaggcatt catgataact acaaacccga cttctacaat gatgattcct gggtcgagtt   1140
cattgagcta gatattgatg aagcagatgt ggatgagaag actgaagggt ctgacacaga   1200
cagacttcta agcaatgatc atgagaaatc agctggtatc cttggagcaa aggatgatga   1260
ttctgggcgt accagctgtt acgaccctga cattttggat actgatttcc ataccagtga   1320
catgtgtgat ggtaccttga gtttgctcca gtcacagaag ttaaatatgg aagctgatct   1380
cttgtgcctt gatcagaaga atctgaagaa cttgccttat gatgcttccc ttggctctct   1440
gcatccctcc attacccaga cagtagaaga aaacaagcca cagccacttt tgagcagcga   1500
aactgaggca acccaccaac tcgcctctac accgatgagt aatcccacat cactggcaaa   1560
cattgacttt tatgcccaag taagcgacat tacaccagca ggtggtgatg tccttttcccc   1620 aggccaaaag attaaggcag ggatagccca aggcaatacc cagcgggagg tggccacgcc   1680
ctgccaagaa aattacagca tgaacagtgc ctacttttgt gagtcagatg ccaaaaaatg   1740
catcgctgtg gcccgtcgca tggaagccac gtcttgtata aaaccaagct taaccaaga   1800 ggacatttac atcaccacag aaaagcttac cactactgcc cagatgtctg agacagcaga   1860
tattgctcca gatgctgaga tgtctgtccc agactacacc acggttcaca ccgtgcagtc   1920
tccaaggggc cttatactca acgcaactgc tttgcctttg cctgacaaaa agaattttcc   1980
ctcctcgtgt ggttatgtga gcacagacca actgaacaaa atcatgcagt agcctttcct   2040
atctttaaat ggcaagggaa aggctgggca caaacgctta aaccaaaact atgttttaaa   2100
tctgtgttgg gagagcatga gagtggatat ggattctaaa atactttttc tggaaatgtc   2160
aaaatatcaa taagtggaaa atcaagaatt cgtaatcaga taaatgctcc cattgtgaat   2220
tataaatatt ttaatgaatt gtcttttaaga ctgtatagtg gcagtgattg tctgtactgt   2280
gggtcttaat tttgtgatac taagcattaa atagctacgt tttttatgta tgtagatcat   2340
gcttttggaa aaagcaaaac aatcaggtgg cttttgcagt tcaggaaatt gaatgcagat   2400
tatagcacag gctgattttt tttttctttt ttaaataact gggaactaaa actctaggtg   2460
agaaggtaaa actagnttgg atatgcaaaa catttatttt gacatnaaat tgataaagat   2520 attttttaata atttacactt taagcatgag kmctttataa tatgctacac acatattgta   2580
gttcagaaca atccatctna ggatgtagca gctacagtgt aaagagggnt tcatgttttg   2640
gtcaatgaac gtaaagaaaa ccaaacaagt tagatttttta caaagcccctt ttataacttc   2700 caaaacttct taactctaaa aatgtctaat aacctgcatt attagaaaaa acatttaa     2760 atttgtaaac gaatattttt ttaattttga aaactttatt ttttttttaat gttgaatcaa   2820 cgtatcatac accaaacagt aaacagaaat tataataatg gaagaagtgc tttcttcgac   2880
aaatttccat tcaagccaca cagctacatg taagagaagt agaagtgatg tggtgtgatt   2940
ggctaggatg cagaagagct tcaggaatac aagaagtgag agcccaagga ttgggaggag   3000
ggggctctca catctccaca gtgcagtctg tcaaacccag cttggttttt atagtattct   3060
```

-continued

| | | |
|---|---|---|
| aagaattatt gtgtacaagg aaaagtctca catgtatgaa atccagtatc cagatggggt | 3120 | |
| aaagttagca gataatagga taggaaatta aagacctaga tctagnacta gtggactttt | 3180 | |
| ttcacagaca gnacacaaat ttttaattca gggagaaggg acagaataaa tgacttccca | 3240 | |
| ctcacaaagc acaactcaga agtaattaaa caggtaacag aaaccttgcc atcaaacctt | 3300 | |
| tgataagatg tattttaagt agtaagcagt atttcaatgc ttnttactta ccctcccagg | 3360 | |
| acaaccgatc tcaaataagg gagataaggt agataaaaat cacttttga ttctgtaata | 3420 | |
| acataaacat agttctttgg gttagcaccc ccccaaaaaa aaatttatgg gagaaagagg | 3480 | |
| actctcagct gactgaagaa tacatntnat ttaaatattt tttagatgcc tgaaacttta | 3540 | |
| aaattacctt taagttttaa tggattacca ttttgccaag acctttgtgg ggaaacaagc | 3600 | |
| ttaatgttta gtgattttga aatctctttc atgcaggaga gacagtgaaa atctagcctt | 3660 | |
| gggtgtttaa ggttcgcctt gttactttgt aatagatttt aataagtttt tctgctactt | 3720 | |
| tgctgctatg gtttctccaa tggctacatg atttagttca tatgaagtat catcaactta | 3780 | |
| gaatctattc agcttaaaga tgtgtgtttt gatgaactat cttaccattt caccataggc | 3840 | |
| tgaccacgtt tctatagcca aaaatagcta aatacctcaa tcagttccag aatgtcattt | 3900 | |
| tttggtactt tgctggccac acaagccgtt attcaccgtt taactagttg tgttctgcag | 3960 | |
| tctatattta actttcttta tgtctgtgga ttttcccctt caaagttcaa taaa | 4014 | |

```
<210> SEQ ID NO 100
<211> LENGTH: 57489
<212> TYPE: DNA
<213> ORGANISM: M. musculus
<220> FEATURE:
<221> NAME/KEY: misc_feature
<222> LOCATION: 19, 49, 59, 71, 78, 172, 1734, 1851, 2528, 3199, 3274,
      4582, 5432
<223> OTHER INFORMATION: n = A,T,C or G
<220> FEATURE:
<221> NAME/KEY: misc_feature
<222> LOCATION: 5505 - 5604
<223> OTHER INFORMATION: n = A,T,C or G
<220> FEATURE:
<221> NAME/KEY: misc_feature
<222> LOCATION: 9593 - 9647
<223> OTHER INFORMATION: n = A,T,C or G
<220> FEATURE:
<221> NAME/KEY: misc_feature
<222> LOCATION: 9648 - 9692
<223> OTHER INFORMATION: n = A,T,C or G
<220> FEATURE:
<221> NAME/KEY: misc_feature
<222> LOCATION: 14425 - 14444
<223> OTHER INFORMATION: n = A,T,C or G

<400> SEQUENCE: 100
```

| | | |
|---|---|---|
| gactcctgct agggttgant gatgcctggt tgttcctgct aggtctaanc cacccaccnc | 60 | |
| tgcatgctat nccaactnta cctaactgta ctgctgatat atccatgaaa tgtttgcgag | 120 | |
| tggattgagc tgatgctatt gactgttgtg aactgaactg ctgatttcct gncaaagcag | 180 | |
| atgagatttg ctccaaagag tcaattctaa ataagtccac tccccccttt tccaatagct | 240 | |
| tttcttttct actacctatg gtggcggtgg gctagaaggg aggatgaaga cattaagaac | 300 | |
| catcattaaa agtagacttt gaaaaaatta aatctacaaa tgacaaatca cagtataact | 360 | |
| acattcttct ttctaggaac atcctgtttt ctagaactac ttattaagtt tagactttct | 420 | |
| ccaatgagtg gtcttaacaa ttatttcaaa caacattttt tgatttctgg gtccgcattt | 480 | |
| atacttcata tcctaactca ttggtcagtg tggccatttt gtagttccta tcattttcat | 540 | |

```
gatgttgttt aaagtagtat gtatatattc ataaccatat tataggtaaa cagagggaga    600
ccatgttgtc tgtaaatatt atttcaattt cttttctacc ttggatgtcc tttatttctt    660
ttctttggct tagtactcct tgtactatgt ttaataaaaa tggtaaacct agaaattctc    720
attttgctct aaatcttaaa gagaaagctt ttgacatttc ctcagttagt ggtgtcttag    780
cctttctatt gctgtgcatg acaacaaatt tggtgtgtta agacccacca aaaaagcagc    840
cagaagtaac gttgtctaat gtggtatgct ggggacacag gtctcccctc agcattgcct    900
ctgctgtact ctccctgcac aggaaagttg cggatgaagc atgctcactg ttagctttca    960
ccaacccagg accaagacct ggggtaaagc accatcatta ctaccttgtc ctaccctga   1020
tgagccagtc ttaccctaag ctttttttgtc taaggttgaa atagttggtg gaggcagttg  1080
ctttgccatg tagactgata atgcaaaatc tcaagggcct ctaaaacatg aaaagtctta  1140
tataggtcct ggaattcttg ggttcaaacc tgagcatgtt caatagcgtg tggtctgtgg  1200
ctgatgccag gatatttctg gaatcttgtc tatgagcact agttgtgttt catatctaat  1260
attagaaaac tgttcatttg tcatggaaaa tgacaataaa ttaatgaagt atgattctct  1320
cagccacaaa gttccttacc atattatatg gaaagcaggt ttgaatagct ccgttacaag  1380
gttataattg ataactcagt tctaacctgt acaaatttca tggtgttctc tatgctatag  1440
tggaagttct atctgtaagg tgctcagtag agactttagg cagccagatg ctgtttcact  1500
gtaatgggtc tgatatcaac caaagaaaaa gccctgatct aatttttatt cactgctttc  1560
cttggaagga atcttactgt tttctgtttt ctccaaattg aagcattcct tttctagggt  1620
ccagagaaga ttcatagcat tcctgaagct agtagaactt ccatgtcctc cagataagat  1680
agtaaattaa ctcataagac caagattgaa aaatagtaac agttgcacct cttncatgaa  1740
tctcccctgc atcttagatg gagactccaa agacatagct ttcttgagtc ctcactcatg  1800
ttggggtatg cttttctgta ttcagctgcc cctgttcacc tatgtcccga naagtaatca  1860
caataaataa attagtttac catactagac ctggatacaa tcatgtcatt ggcatgcccg  1920
tcatggctca tctgagacaa atacatgttt gttcacatat cctaatgtgg atcaaaaatg  1980
gaatcctgtg tccggcccag ggctcaggcc tctgagcgag gtggatgtgg aagtttggc   2040
ggatgtgggt gcacaccccc atggcaccac tgggcatgca cagggctgtg agaagccgca  2100
ggacccccct caggggtggg aaaggttcag tctgaagtct ccacggacct gccagagttg  2160
ggctcagact ctcaggcatg ccactggagt ctgtggaaga gtgcagaggc cagggacatc  2220
aggttctctg tcatggacac ctcagatgct gctggatgtc tcagaagagc tgagaacaga  2280
gtagggaccc gggctgaagg gaaaagggca tggagagggc tcaagatggg tccacaggga  2340
tgagagtcct tgtcttgctt aggcagctag ctgggtttag cagaggccct ggttggagtg  2400
cagggaggcc tcctggtggg agattagatg caaagttctt tagtagatga cctgctccgt  2460
tgctctagca cggcggatcc ctaaggtctt taaaattaga tattgtagtt tcttctctgt  2520
ttctttanct ctcattgatg tggtttggtt tataatgcca gatctttaaa ggatctcact  2580
accccacccc ccatcttgcc ttatttgaga atcttctgtc cattaaagac ataagagcct  2640
atctgtctgt atacttcgtt gtagacaagt tctgaccatg taataaatat tccttcatgt  2700
ttctctcact tcagcctttt cagtgttgga catgatgtcc tgattttctc acatatgaca  2760
tccttatgag gatttttcaa actaagtcag tttcatcctg ttaatcttg gtgtttcaag   2820
tcaacatacc ttacaatgtt ttccagtcac cagagcacta gaatctcata gggcatttga  2880
```

```
tttatgaata ggactattag ttcttctata attctgctca cttgtggtaa tgcaatcgag    2940
aaatgaagat gtacaattgg cagagtgaaa aaatttaaat attcagtaca cttttttgga    3000
tatagtgaaa cagtaacaca gtctctttta atattatttt tttatacaag tagattaatg    3060
cagctctcag cactcaacga agacatttca ttatgcagca gagattctta cagaaaacca    3120
cagctggtca aactgcagag aataggtgac actggcctgt gtctaaacac aaatgctaca    3180
cagaagtctc cagaaagcnc ttcagaagag caaccaataa acaaacaaac aaacaaacaa    3240
acaaggaaag aactagagaa ccaggaggac ttgntaagaa acaatgtttt gtgggcgtga    3300
cagagatgat ggatgatgta ctcagacatt ccataagatc tacaaccctg tcggtggaac    3360
aacattatga actaaccagt accccggagc tcttgactct agctgcatat gtatcaaaag    3420
atgacctagt cggccatcac tggaaagaga ggcccattgg acatgcaaac tgtatatgcc    3480
ccaatacagg ggaacgccag ggccaaaaaa aatgagaat gggtgggtag ggaagtgggg    3540
gggaagggta tggggacttt ttgggatagc attggaaatg taattgagga aaatatgtaa    3600
taaaatattt taaaaaataa aaataaaaaa aatggaaaaa aaaaaaaagc ctagtagact    3660
catcacactt cccaaggcta cttcttcctg tacctgcagg aggtgcactg ctctctttga    3720
acttacagcc tgttcttgag gacttctaga tactgccttc tttggggaa cccgatgggt    3780 ggagaggagg gaagtctccc gcaactacca atatttttcct ctaggaggag ccccgccgcc    3840
caattgagag cgacacgcac caactcgcaa ctcctcgcca gaaagcttca tcccagccct    3900
gcggactgag tagcggggc ggcgttcagc ctccccgcag cggccccgga gctagctgcc    3960
ctcggctccc gctgcccttc ccctaggcag cctggatccc cgaggcggcg cgggtccct    4020 cgcagagccg aacgccagcc gacttttccc acccctcccc tctcttcctc tcccctcccc    4080 tccctcctc ccttcccagt ttcaccccgc ccccttcctc ctccccaagc ctgacaaccc    4140
acgagctgcc aagcaggcgc agccatggga agaggaggcg gtctagggag cggcggcact    4200
ggcagaggcg gctgctacag cggcggtggt ggcgacggct gttactgaac cccggcagcc    4260
gcggggatcc cgggctgggt ccacgcggcc tgaggcctcg gctccagcag cccccaagcg    4320
gacacgaacc cgcgttctgt ctcccgaggc gaaactccga ggtactggag gggagttctt    4380
attcccctca cattcgtgcc aggagacctg ggagtagacc cgggcatgcc aactgcttgt    4440
gaaaaattgg ggtcactttt atgtatttgc cccgataatt ttattttatt ttattttatt    4500
ttattttatt ttgatgagtt tagggtgggt tgtattccct tctcaaaagt tgttttctgc    4560
tgatgggttg gtgtaacccg ancctgcgtg tcctggagaa gtgtgtgtgt gtgtgtgtgt    4620
gtgtgtgtgt gtgtgtgtgt gtgtgtgtgc gcgcgcgcgc ctgtgtgtgt gtgtgtgtgt    4680
aagttgttct tggtgctgag tgaagctgaa agttgatgtg ggcgacaagg aatgggggc    4740 agcaagcgaa ctgtcccagc ctggagcctg ctccaaccag gttgtgagat gcaaggagag    4800
gtttcttcct aagactgttt tcttggtctt aaaagtttcg cgagtgtgtt tgtcaccatc    4860
agcctgctaa cctggagcaa ggactgtgga agctgctgct gctgtctgaa gcgagctcct    4920
ggttgggtgt gatggcctga gggactccgg agggtgggtt tgaagcacg cgaccccgc    4980 agcgctctgc ctttgcgcag tctgtgcagg ctgcagctgc aagctggaag cagaggagct    5040
ggagtcagag tcaccgacgc cagagcctcc atgaactggg gtgagtggaa attgtggcaa    5100
gccaaactgt cccggcgctg gacacactcg tggttatgaa atcaaccagg ctcaaagttc    5160
tgatagaact gcagagtctt gagagctgcg cgggtgagtc gggtcacgtc tggagagaga    5220
gagggagaga gctggctgca agcagtggtt gtaacatggg actatccgct tgtgggtgcg    5280
```

```
tggggaaatc tatttctggg caaggacttt atatatagca ccggggagta ctgtctgctg    5340
ggaccagggt gcaggtttcc gtggtgagct ctgatgtgtg tgcttgaaga ggtgtgcagt    5400
atgtatgtgt gctgtatgtt tgcacgcgtg tngtgggagc ccattgggag gtgtgttggc    5460
ttcctgaatc agggtgttga gtgggagaaa gaaaccatat agatnnnnnn nnnnnnnnnn    5520
nnnnnnnnnn nnnnnnnnnn nnnnnnnnnn nnnnnnnnnn nnnnnnnnnn nnnnnnnnnn    5580
nnnnnnnnnn nnnnnnnnnn nnnngaatca gggttttatt ttagtttcct tgtcccacc    5640
tcccgtaatc caatgtggtg ttcaaactcc cgtcctgacc ctccgtaatt cccattggac    5700
tctcatatgt ccagggctat cttttggact gaggtttgaa ccatccgata tatcagacac    5760
aagcataatt cttggtttgc atagagattg ttttttttta aagtatacta cttggagatc    5820
agggaattga aaatgttgtc ctctgtctgc aaggaacatg tagaacattg acacttttat    5880
agctcttcag ggattccatt ggctgctacc agagccacac ctgtagagcc atgaaacaac    5940
acttcttgct cagcgttcac tatgattagg gataacagga agagttttat cagtattgtc    6000
aagtttgcaa atgttagaaa agaagaagag aagagaagag aagagaagag aagagaagag    6060
aagagaagag aagaaaagaa aagaaaagaa aagaaaagaa aagaaaagaa aagaaaagaa    6120
aagaaaagaa aagaagagaa gagaagagaa aagaaatcag tccatggagg ccattgaaga    6180
attggtggag tgttgataag gtgacttgta aataagggcag tattatggaa atactgggac    6240
taagcatcaa agtggttggc aatagttgtc aaatgcaaca atccttcccc aaagagttga    6300
gtactgagtt tctttaccac ccatcctgcc ttgtctctag agaagtgtgg acatagtcac    6360
cataggttat tttcccaaag aagtgtattt ccttcagata aaggcatgtg cttacagagc    6420
ccattgatca agtccctcat tcattagacc gaaagactga aggtgcagcc actcttgggc    6480
ttctaaatca ctagaaaaat ggagactggt ggctcttggt gaacatatgc ttgggtgttt    6540
cagagcacac agtcattccc agggttccct taatgtttga aaggtatttc tcacctctca    6600
gcttccctct tgttacacct ccctgggatc agtacagtgt ttgtaaaaca taaattaagc    6660
tcctttggtc cttgggaaag aggtgtaaga aatgttagta tagtattata gaagattttt    6720
atttttatttt atattttatt ttttgtctta ttcaaagccc tgtgctgagc aatttttttc    6780
tatctccaga tgaaactaaa agaaaataca ctaggccctg ttattagagc tgagcttgtg    6840
ggtcttttgc tgtgaggtga cccagtggct ggaagccaag gacctgaaag tctgcactgc    6900
tcattctgtt tcctgaggaa agagctcatg ggatggagag agaattccaa cacgctgtgc    6960
atcctcatga cacatggggc acttctgaag tctgaggcaa tgctagactt actaagattt    7020
cttccacaac gttcttgtcc acacactcac gacttcacgg ggctttgaat gttatatcaa    7080
gaccgtggtc tgtggctgct tgccttgacc ttgtcccttt tctgtcttgc aggtctcagg    7140
tatggatctt tgtcaggtct tcttaacctt ggcactggca gtcaccagca gcacattttc    7200
tggaagtgag ggtgagttct acattccttt tctccttgtg tggtataaag aaacaaagca    7260
gtcctgtgtt aaatctgaac aaaatcgtct aagttttagg ttaacagcaa acaggaaacc    7320
tgtcttagct ttaaattcat aacccaggag agagccattc tggggatgtg taagtggggc    7380
aagagtcgta ggctttggca actgacattt tcctattgga aattgatgtt acgtaatgca    7440
caggggggaca tttatgatga agacaagccg ggtctccggg agagatatta aaatcacacc    7500
aaagcatcat tagcctacta atcgctcagc tcatctgtaa ctaagcatag cagaatctgt    7560
ttccaaagcc tggaatgcag tccccttaat catattccct gagatgtaaa tctcaggctt    7620
```

```
ccaatgaatt tgtgcccctg ttctctgaat aatcattcat tggctgagtt ccagaggaaa    7680
aagacaccca aactaggtga ccaacgttac ccagaaatgt gagctacctt agctgtctga    7740
ctatgttccc ttatgttttt cttttatact ctcccggttg tctcaatatt ttcagattca    7800
catgtcatag cagaaacaac aaagaataat gcaaatgggt gtggggtgt ctgtctagaa     7860
aaaaaaaagt gtccttacaa agggctggcg gacgttttga agactgtctt gagcacgagg    7920
cagttttctt tcctggtttc attagaggat agaatagaaa caatatgttt ttgccatgct    7980
gtgcctctgg attctgttgc tgctttaagt gtagcctact cccttactca acacccaact    8040
catgttggaa aacacaattt aacaggcgac ttaacacctt aagatgtccc gctgaccttg    8100
tgaccaaaaa taaatgccca gtagtgagct gctgactgtg ttaggagcaa cttggaaagg    8160
ggaacgaata gaatgcacta tttgatttct taaagcaatc ccaaaaatat ttatagaaaa    8220
gaaatcataa ttgtttgtaa tattttgggg tttttctggt gttataatgt caatattata    8280
caagtcagac gtggagggag agagagtcac gggctccact tcagccgctt tcccatggc    8340
tgcttttag agcctggttc tgagccagag aattacagct cagctcctct gccattccag      8400
agtcatggtg gtttaatcgc tcctttcttc actaaggtga ctttcagtcc aaggggcaag    8460
gcttgaggag tttaaaagcc agtgaagtga aaagcacagc agaacaatca ttaaagaagt    8520
tgagaaatgc atcccaggct aacagattag agctcaaatg gttttcttta ttttttcttt    8580
tttaattaga tattttcctt tatttacatt tcaaatgtta tcccctttct ttgtttcccc    8640
tctgaaaatc ctctatcccc tcaccccatc aacaacccac ccactcctgc ttcctggcac    8700
aggcattccc ctatactggg gcatagaaat ttcacaggac caagggcctc tcctcccatt    8760
gatggccgat taggccatcc tctacatatg cagctagagc catgagtctc accatgtgtt    8820
ttctttggtt ggttgttcaa tccctgggag ctctcagggt actggttatt tcatattgtt    8880
gttcctccta tggtgctgtt aaccccttca gctccttggg tactttctct agatccttca    8940
ttggagacct tgtgctctaa tggataatga tgagcatcca cttctgttca aatggttttc    9000
aaacctagag aatttccaag ttctgttcaa cagcttaaac atttgcccag ccttcaactt    9060
catgagaaga atggtgacaa aaaagtatat ataatgttat aagccgtgtg tgtgcttgtg    9120
tgtatgtgtg catgcaagtg catgtataca catgattacc cattttctct ctgtggcaag    9180
agaagccttg atctacttct atagcagaaa tcctgaatat aataatctga gctcaactac    9240
agctctcttg gtgttcatta attcactaga ctcaatacag catatttgct tctttgtgcc    9300
ctatggatga ctgtctgcca agtccttctc ctaccccaat gtggtaacca ctgttgtctc    9360
tacaatttga ccttttattt gtaaaattac acattgatgc aaccatgttt attgttcttt    9420
cctgatctga cctctttctc ttagactgat ggccactttt gctttagaga cactcacact    9480
gtggcaatgg caggagcttc aagctgaagt ctgggctatt ccatgtctat gctgttatgt    9540
tgacagctgc atgaatacag acatagagtc ccttacacag tggtgtttca acnnnnnnnn    9600
nnnnnnnnnn nnnnnnnnnn nnnnnnnnnn nnnnnnnnnn nnnnnnnnnn nnnnnnnnnn    9660
nnnnnnnnnn nnnnnnnnnn nnnnnnnnnn nnggacgacg gttccttgat ctgggtactt    9720
tctctaactc ctccatgggg gcccgagtcc atccaatagc tgacgtgagc atctacgtct    9780
gtgttgccag gccccagtat agcctcacaa gagacagcta tatcagggtc ctttcagcaa    9840
aatctgcttt gtatgcaagg tgtcagcatt ggaggctgat tatgggatgg atcccaggta    9900
tggcagtctc taaatggtcc atcctttcgt ctctcctcca aacttgtctc tgtaactcct    9960
ttcatgggtg tttgttccca attctaagaa agggcaaagt gtccacactt ggtcttccctt   10020
```

```
cttcttgagt tcatgtgtt ttgcaaatgt atcttgtatc ttgggtattc taagtttctg    10080
ggctaatatc cacttatcag tgagtacata tcatgtgagt tctttgtgat tgggttacct    10140
aactcaggat gatgccctcc aggtccattc atttgtctag gaatttcata aattcattct    10200
ttttaatagc tgagtagtac tccattgtgt aaatgtacca cattttctgt atccattcct    10260
ctgttgaggg acatctgggt tctttccaga ttctggctat tataaataag gctgctatga    10320
acatagtgga acatgtgtcc ttcttaccag ttggaacatc ttctggatat atgcccagga    10380
gaggtattgt gggatcctcc tccggtagta caatgtccaa ttttctgagg aaccgccagg    10440
ctgatttcca gagtggttgt acaagctcgc aatcccatca acaatggagg agtgtttctc    10500
tttctccata tcctcgccag catctgttgt cagagaagtc aggtataatt ctgataggtt    10560
tacctttata tgttacttgg cattttttc cttgcagctt ttaatattct ttcttgttat    10620
gtgcatttag tgtttgatta ttatgtgaca ggaggatttt ctttctggtc caatctattg    10680
gtgttctgtg ggcttctgta catttatggc catctctttc tttaggttag gaaagttttc    10740
ttctatgatt ttgttgaaga tgtctttggc ttttgagctg ggaagcttca ccctcttcta    10800 ttcttttat tcttaagttg gtcttttcat agtgtgcaaa attcttgtat gatttgagtt    10860
aggaactttc tacaatggca ttttctttga tcatgtattc atttcttcta tggtatcctc    10920
tatgtctgaa attctctctt ccatctctgt attctattgg tgttgcatgc atctgtagtt    10980
cttgttctct ttcgtaggtt ttccatctct aggattacct cctttgtgtt ttctgtattg    11040
cttctacttc tgttttagg tctggatcct tttattcatt accttcacct gtttgattgt    11100
attttcctgt atttcttttt tttttaattt tattttatt agatattttc tttatataca    11160
tttgaaatgc tatcctgaaa ttttcctatt tccccccacc cccgctcccc tacccaacca    11220
ctttcccgta tttctttaag ggatgtgttg tttcctcttt aaaggcttct acctgtttga    11280
ttgtgttttc ttacatttct ttaagggact tatttatatc cttttaaag gtctctatca    11340 tcttcatgag atgggattta aggtcacagt cttgctcttc aggagtatta gactatccac    11400
tgcttgctgt actaggagag ctgggttcta atggtgccat attgcattgg cttttactga    11460
ttatgttctt gcacttgcct tttgccatct ggttgtctct ggtgttggct ggcctgggtg    11520
tcccatgttg aagcaggcct cccagatgaa ggtggagctg tgtgtctcag gtatgagcag    11580
gcctcctggg aggcagtctg agttatgagt gtcagattgg agctgacttc ctggaaggca    11640
ggtggagctg tgaggtgggg cacagagtgc tgatctgcat ctgcttcagg tgtagggtg    11700 gaccagaagg aagatggagc tctgacaggg tggggcacag cctacagctg ctagctgaaa    11760
ttcccatcag gtagggcagg gggattaggg tgagtgaggc agggagggg ctcacctgtg    11820 tatgttggtt tatgtaggca gagctgtgaa gtgtgtgctg agtactgatg tgcccatatt    11880 ttctttctt tttcttccct gtgttttatg tgagacagag tacccagtgt atggccttcc    11940
actaagacaa tattatcagt tgtctgagag aatatgggga aaacaaacat aatgtgtctg    12000
gccacactct tgaaaacaga atacttgggt gcccttggt caccaaaatg ttaagtgaga    12060
atacaattgg ctaataccga ggtgagaggg aacatcctat aatacaattc aattcccatg    12120
caaactacct acagatactt tcacatcact catcttgata gctcagcccc acaaaactgc    12180
ttcctacttc agatgacaaa tgtatgtaat atactgtact tctgaaagat ttcttgcta    12240 taatttataa atagactgta ctaaagtttt gaaatgtctt tttttttca agctggttcc    12300 catgactcat ttattagagt tgatgaattt gctacaccag ctcacagaac tcagacatta    12360
```

-continued

```
aattaatgac tttggctttt tactgagggc atcacaaagg agacagataa tgaggtatta    12420
tattaataag cctctgctac tgtaacaaat atctgaaaca atcagcttat gaagagagaa    12480
ggtttatttt gactcacagg tttggagaac tctggagttt ccagagcatg agtggttggt    12540
tccactgctt ttgagcctat gaaatggagg acactgtagc agcagcatgt ggagaaacca    12600
cttttccttg ggacgaagaa attgctaagg gtccaggttt tgttttaaaa tcactgtccc    12660 ccaccccct accccaagt gatgggaaga cctcctaact cacctttatg tttcaaattc      12720
ctaccacctc tgagtagtgt caggctgagg atcatagctt tagcacatgg gcccttagag    12780
gaaattccat attgaaacca taacatatga agaacatgct gtagccactg tgccctctaa    12840
gcatctccag gttatcaacc aattgaaagc ttctgaactc atactatcaa ttttttgtga    12900
atgttgtatt ctctgactac atttattaaa ccactgacca ttggtgatga gcttagccat    12960
tagaccctcc ttcctcccta gaggctttga ataacactga aaaaaattcc agttctacaa    13020
ccataaatct gttttttccc atgccagctt ccatcctgag ggaggaaatc cccagccact    13080
actcaactca ttagtgtatg aaaagactca tcgctctgag tattacaaat attttaaaaa    13140
tgtatatgtt aaaatacagt gggaagacta aatatagatt tagcagtgtc acacatagct    13200
tcccttgctt tcatttaaat ctcagtattt gttgtttctg tgtagtaaca agagctggtc    13260
tatccagtcc tcttacacac tttccaccaa gaccagacaa caagtcagac tctttgtagc    13320
tagggccttt gcaaaggaac ccagctggaa ggagccttac tgagcacttt ccactattgc    13380
ctaccttcca gacagcctgc tcccagctgt attacaatga ttgactcact tgctgcctat    13440
tcaaaaaact ccagggcctc acttgttctg ctttgcccct cccttattc tttccccatg     13500 cccaggaatg ttctcactta tagtatttcc aaaaataatt ttttaattaa atgtgggatt    13560 tgtattttc taaagaaacc tgtgttctcc ttcctatgca caagggaaac ttgagtttga     13620
actcaaagga tagatggtgg aattgttctc attgttctgt attgtgtctg ggcatgcgac    13680
ctgaggtaat gacaaccaaa aggcttccat ttgctctgac tttacaagct cttttaatg    13740 catagataca gctttaattt taatgggggg gggttggcat ggaagcctat tatacaaaaa    13800
tgacactata acagggtcac agaagatcgt ttttctacag ggatgactaa tgattttctt    13860
ctctttcttt ttcagctaca ccagctactc ttggcaaagc ttccccagtt ctgcaaagaa    13920
tcaatccaag cctggggaca agtaagaatt tctgtcattc tactaacttg cactgatggt    13980
ttccatatgt tactataatt caaactactc tcctttctct ttctctcttt gggatactgg    14040
taacaggaaa agtgacagcg tttgaatttt ataagcaaaa agtattttc aggatttatg     14100 tttcaatttc tgtatagagg tcatggttta tttttctgtt ttgtttatgc ttgcaggtta    14160
agagaaggct ttattatgcc ttgttttaca aacttgtttt taacattatt gttgttgata    14220
tttggtagta tttatataat gcttgcattg gcaaaaaatg gaatttattt cccgaaccaa    14280
atttacatat atacctcaca attctgcctt catataagca gcctatttt tacatgtcat     14340 cgaacaccgc ccccccccc cccgtctttg ctaatcttcc cctatctaca taccaaactc     14400
aaccttcagc tcacagaaaa aggtnnnnnn nnnnnnnnnn nnnnnnnnnn nnnnnnnnnn     14460
nnnnnnnnnn nnnnnnnnnn nnnnnnnnnn nnnnnnnnnn nnnnnnnnnn nnnnnnnnnn     14520
nnnnacatca gggccacaag caggaaactg tccaatctca caatcaaagt aaatgccaca    14580
gttgtcaaat gtggacatac ttgctatatt cacacagggg acttggacta tataatttac    14640
acatgcagta ttaaaataaa taattcagat tcagcacaaa gtttactttc tttgctataa    14700
attttaggca agtatgggag tgtatgaatc tttaaaaaaa aaaacaaaat ggagctaaga    14760
```

```
aagtgacgat aacataactt atttacaagt ctccaaattt tcttgaaaat atcacatgag    14820
aagtaagcaa atagaattca ccagcttttta gagcatttac caaactccag tgaatatcaa   14880
tacctgcata aaagttacct cacactgaac tttgtgtaac caacatcact ttctaattcc    14940
aagctcctac agaacatccc atagagctct taatacccaa tggctttct agcccaatgt    15000 ttcaaagtcc ttccatagtc ttccctaaaa catggtcagg ttgtcacaga atatgccac     15060 tatgctggta actatttgtc ttggtcaggt ttctattcct gcacaaacgt catgaccaag    15120
aatcaagtag gggagaaagg ggtttattca gtctacactt ccacattgct attcattacc   15180
aaaggaagtc aggactggaa ctcaagcagg tcaggaagca ggagctgatg cagaaaccat   15240
ggaaagatgt tatttactgg cttccttacc ctggcttgct cagcctgctt tcttttagaa   15300
cccaagacta ccagaccaga gatggtacca cccacaatga gctatgcctt ccctcttga    15360 tcactaattg agaaaatgcc ttacagctgg atctcatgga ggcatttcct caagggaggt   15420
tactttctct atgataactc cagtttgtgt aacgttaaca cacaaaatca gccagtacag   15480
tcaacctctg gcctacacaa atacacacag atatacacac cctcatgtac acacacacac   15540
acacacacac atccaagaag aaatgcaaat gactaccaat ggtcttccaa gatcttttga   15600
gtacaagcag tgttaatgct aaaatttctt cagaacgtgg aacatcttca gttccaacac   15660
tcatttgtac aagtgggaat taatctgggg tgcaaaggtt gaactcttgt gaattgcaac   15720 attctttctct gggatgctat agtagatgct aaacaatgcc actgttaggc ttaagcattc  15780
ctgcttagga cttttctcct ctctgcctat tatcagattt ctagtcctag gcatgttttt   15840
catctttcaa atgaactact tgccctcata tcctttccac tagctctggg tcttaaacaa   15900
gccctacaga ataatgcagg aaataaagtc acaacttttt ggcttcaaaa ttgatgactg   15960
acagtagaaa ggaatagctg ctgagaaggt aagcccggaa aagtgccttt ccagatgtta   16020
gtatcacctc ccagagagac tggctttatc ttcatagttt acatacttca gcagttatgt   16080
tccgtgggaa tggcacatgt ccttcctcac tccatgtatg ccttttcttc ttgttctgca   16140
ggttcttctg gaaagcctcg attccaccaag tgtcgttccc ctgaactgga gacattttca  16200
tgctactgga cagaaggaga taatcctgat ttaaagaccc caggatctat tcagctgtac   16260
tatgctaaaa ggtgaaggct tcacgcccctt ctgactttgt cctccactga tttctcagtc  16320
ggatggtgtg gagagattcc cattgagtga aagcacgtgg gcgtgcctgt gggcatacgt   16380
gagtgtgtgc agaggcttga gtaatatttg aactgaggag gtctcaggga cctttctaat   16440
gtagtgtgtt aaaatgggga aaagaagtga aaaaaactgt gtgagtatat gatggagagg   16500
ctttggaggc aaagaaaatc acagatgcaa tgtccgtgtc agcatgtttg agaatcacaa   16560
gagcctgtat aggtgacatg agactgaaac ttgggaaagt gacatgtgaa ggagttagag   16620
ggctacccag atactgtaac aatgagcttg tagtcccggg aagaccactg aatcttactt   16680
tgtgctttaa aaaactgtg ttttaagagc ctccaatact tggcttctct ataagaatta    16740
attaattaca ctaagtgagg gaacttgctc ttttgttttt atccatgtcg tctggaatga   16800
cacttgatga ggaagacaaa catctggaaa cgtggtcatc accagtcctt aagtttcatt   16860
ccctggccaa gtcctccttt cctctcctcc cgctgttact atgcagtatc agcataattt   16920
atgggatagt ctgtgatatt ttaatacatc tatatgatgt gtgattctca aaccaggaca   16980
attggtgtat ctatcacttg aagcattat cattgtgtgt gtgtgtgtgt gtgtgtgtgt    17040
gtgtgtgtgt ttgccagggc caccaaaaat cttctctact agatattttt aaatacatga   17100
```

```
ttaatcgttg tcaactataa ttaccctact gtgctataca acaaacatca ccattttaaa    17160
tgttagagtt aaatactttc ttgtctttct ttcctccatg aacctccagg gaaagccaac    17220
gacaagctgc aaggttagtg aagacccttt gtcttagact ttcatccaag ggcctgagaa    17280
tgacatgttc cactccgtag atgatagggga agggaaggga aggaagatgt gggagggcag    17340
ttagtccgag ctagcctcct gcagtatgtc ctggcttcag tccttgctca ccaaggaaca    17400
gccagcaaat tagttaaacc aagtctcctc cattctagta gtataatagg cttagttcac    17460
agcttcttag gtggaagaat tcctgataca gttcattctg cataattaat caatcatcaa    17520
tcaattaatc aataagcaag attttcttag tatataataa taatttaaaa caataatgat    17580
atagaaccca gattcctaaa ctataaaaag taattcctta ttgcttatgc ttattaatag    17640
actataagaa ctttctaatg cctacctgag tgtttaattt acagacaaca aaaactttaa    17700
gtgaacaaca aagactgact ctacccatct tctagttatg aaaggcacca cagacatacc    17760
cctgcctaag gcacacagag atgaggtagt ttggaaccaa acgcactact tatttaactt    17820
gaggttgata ctataaagag gtatgggcca gtaaagtaga ggcaggcaga cagacagaca    17880
gacagacaga tactcagatg tgagctaaag tgtttgggaa cacttttgaa aatgtatgaa    17940
ttgattctgt tatttctaat atgaaaagag agagaaactc actagatgtc atctttacac    18000
cttgcttcgg tagctcagac agcttagcac catcaaaaca aatgagaagt ttttcataca    18060
ggcaccactg accaaactga tctaagtagc agtgggataa catcttgaat cagttctaat    18120
ccaggaaaat gattttttcta ccctcctgtc agtcacccaa cctagctgtg agccaaagaa    18180
tgaatccaga gacactgagc cctcacagcc atccttgttt ctcactttct tcagtcagag    18240
ccacagtatc tgtctgcagg tctcctcctc acatcccaat cttcccagca tccctagtct    18300
gcactcaccc tgggaactaa caagaaatct gctgcaagta tgaccggggg aaaagaatat    18360
ctccgacata tgcaaaagaa catcctgttt tagctctagt ggaacctaga atctcaggag    18420
aaaaatatcc ccatctccct aaataccatg aacacaaaca aactcatgat gaagtgccaa    18480
accaaaaccc caaatcagga ttttgtgttc tctctacaaa aaaaaaaaaa aaaaaaaaa    18540 accaaccata aatactttga atattctagc caaacccaca aaagtcctca gccctgtttg    18600
tctgagaatt gaatgtaaaa tcaagggtta gtctatcaga atggatctgt actgatgcat    18660
gggctctcag cacccaacta cacagagaca aaggcacagg gggaacttcc aactcttgtt    18720
atttggtctg agagtttgtt cctaggcaac tcctaaaact atagaatcat tcctcccatc    18780
cctcacccac aacactacag catactttaa ttcaacactt atagtctgtg gaggcagaaa    18840
gaaccagcag atgtggtagt gtgtctgggc tgcttttgga atccaaagca cacatgaatc    18900
taagcacgtt gggctgtcag cgggacagaa aggcacaagc ctgcatgtgt tctgcttgga    18960
cccaattcct agccaggtaa gctggcagag gagatggcct agcttaagaa agcagctgat    19020
tcaaagcagt ctctgaagcc ctgtgattga gatcctgcca aatcctgcct ctgcacttga    19080
aggcaactgg gtttgaatgc aaagcagagc tgtgccagaa agagactctg ctgagtgcgg    19140
ccgagctttg ggaaggcttc ctggagcaag ctgaaacctg gtaacatcag cctttccttt    19200
cactcctttt accatttatt ttaactgaaa aaaatattat catcagactt catcctaaag    19260
gatttgagat tcagttcact gggatgtagg gtgacgacta atctgtctcc ttttttgttag    19320 aggaggttgg ttagctatat ccttccctga agtttatgcc aggcagaggt gagatataag    19380
tatggcctgt gggttcaagg gactctaaat gacacagtag ccttggtaga aggagacagt    19440
catagtagtt aacagttgac atcacttagt tggaattatt taatgtttgt gggcctgaaa    19500
```

```
tctggtttta ttttatttat ttatttattt atttttttgg ttctcactat tcttttttt   19560 tttaatttt ttcccacttt ttattaggta tttagctcat ttacatttct aatgctatac   19620
caaagtcccc catacccacc cactcccct ttttggccct ggtgttcccc tgtactgggg   19680
catgacttct ctgttcctta tttttactcc atgaaaacct ttagagagaa atactgcttt   19740
cactcttcta tttttaatga aatctcttat ggtccttact cccgtcacaa ggtagtctgt   19800
ggcaatcaaa gaacttcatt tgagggcaag aagaagaaaa gtagctgcct tagagcacct   19860
tacgtcttgt acggaatgca gggcagacaa gtggcttcat gtttcatgag gttattcggg   19920
tttggcctga gatttactag cttaaaagat ccattttagc cagatatggt ggcatgtgtc   19980
tagtcctagc acttgggagg cagaagtaag tggatctctg agttcagcgc cagcctgggc   20040
tacaaagcag tttcagaaca cctaggacta cacagctgtt ctgaaatcat gtctcaannn   20100
nnnnnnnnnn nnnnnnnnnn nnnnnnnnnn nnnnnnnnnn nnnnnnnnnn nnnnnnnnnn   20160
nnnnnnnnnn nnnnnnnnnn nnnnnnnnnn nnnnnntga tggccggtcc aactatgaat   20220
atcctcccat ccctcaccac aacactacag catactttaa ttcaacactt atagtcgtgg   20280
aggcagaaag aaccagcaga tgtggtagtg tgtctgggct gctttggaat ccaaagcaca   20340
catgaatcta agcacgtggg ctgtcagcgg gacagaaagg cacaagcctg catgtgttct   20400
gcttggaccc aattcctagc caggtaagct ggcagaggag atggcctagc ttaagaaagc   20460
agctgattca aagcagtctc tgaagccctg tgattgagat cctgccaaat cctgcctctg   20520
cacttgaagg caactgggtt gaatgcaaag cagagctgtg ccagaaagag actctgctga   20580
gtgcggccga gcttgggaag gcttcctgga gcaagctgaa acctggtaac atcagccttt   20640
cctttcactc cttttaccat ttattttaac tgaaaaaaat attatcatca gacttcatcc   20700
taaaggattt gagattcagt tcactgggat gtagggtgac gactaatctg tctccttttt   20760
gttagaggag gttggttagc tatatccttc cctgaagttt atgccaggca gaggtgagat   20820
ataagtatgg cctgtgggtt caagggactc taaatgacac agtagccttg gtagaaggag   20880
acagtcatag tagttaacag ttgacatcac ttagttggaa ttatttaatg tttgtgggcc   20940
tgaaatctgg ttttatttta tttatttatt tatttatttt tttggttctc actattcttt   21000
ttttttttaa ttttttttccc actttttatt aggtatttag ctcatttaca tttctaatgc   21060
tataccaaaa gtcccccata cccacccact ccccttttt ggccctggtg ttcccctgta   21120
ctggggcatg acttctctgt tccttatttt tactccaatg aaaacctta gagagaaata   21180 ctgctttcac tcttctattt ttaatgaaat ctcttatggt ccttactccc gtcacaaggt   21240
agtctgtggc aaatcaaaag aacttcattt gagggcaaag aagaagaaaa gtagctgcct   21300
tagagcacct tacgtcttgt acggaatgca gggcagacaa gtggcttcat gtttcatgag   21360
gttattcggg tttggcctga gatttactag cttaaaagat ccattttagc cagatatggt   21420
ggcatgtgtc tagtcctagc acttgggagg cagaagtaag tggatctctg agttcaaggc   21480
cagcctgggc tacaaagcaa gtttcagaac acctaggact acacagctgt tctgaaatca   21540
tgtctcaaaa accatgatgg ggatggggg tcctgagatt gggagttgtg ttttcaacta   21600
gctattcctg acacacttca cattcagatt aactcttata agagctatgt cctgtggaac   21660
tgatggattt agaaatccta accagggttt cacatacaag ccccaggaac aggactactt   21720
gcattgtcaa atgtcagaaa acctcacaga aactgaagca caacgagct aggtggctcc   21780 ttatagtaga cgcagacctg ctgaccacta gctgccctgg atatttgcac catcctaaga   21840
```

-continued

```
cttactttttt aaaactgaca cagttagtca cataaagtgc acttgatgtc ttcgctggta   21900
taggtttttg ttgttgttgt tgttgttta ttttgttttt atcttttta ttagatattt    21960
tctttattta cattttaaat gctatcccga aagttcccta taaccctgc gcccctaccc    22020
acccactccc acttcttggc cctggcattc ccctgtactg gggcatataa agtttgcaag   22080
accaaagggc ctctcttccc aatgatggac tactaggcca tcttctgcta catatgcagc   22140
tagagacacg agttctgggg atactgatta gttcatattg ttgttccacc tatagggttg   22200
cagacccctt cagctccttg ggtactttct ctagctcctc cattgggggc cctgtgttcc   22260
atccaatagt taactgtgag catccacttc tgtatttgcc aggcactggc ctagcctcac   22320
acgagacagc tatatcaggg ttctttcagc aaaatcttgc tggcatgtgc aatagaatgc   22380
ccagtgctct ggacaatttg ggtagaactt tttagttcac actcagtttg aatgtcagaa   22440
tcattcaatg actcacctgt ctctgactgt tcgctgtcac agcatggtgc acaagcctgc   22500
acaagcatac tttatcttaa ccttagcttt tctctactta cttcccctgt gatagcggag   22560
gcttctttcc acccaagggc tcgcagcttt taagaatctc agccggaatg taagcaacag   22620
ttccctgcct ctaattctga attctctctt gtgttaatct caagtgtatt caaacagctg   22680
atgagcagct gtctcaatgg ccctgattct atgtgagtcc ctagtaccaa ataactagcc   22740
tgagaaacag ctgttaagga actgtaaatg cagctgactt cagggctctc catgccttcc   22800
tttcaggccc tgccttcccc ccagcctggg ttttcattgc ccactgccgc cagcacatcc   22860
tgccagtgga aaactctcat ccgcatctag cttgccagca ccagcacctg tgcctgccca   22920
gagtcactcc tgtcactctg tgtgtctgtc tgtctgagtg tgtacatgtt catatgtgtg   22980
cacaaatgtg tgtgtttgta tatgttcata aagatgtac atgcttgtgc acagatgtgt    23040
gtttatatgt atgtcatgta gaaggccgag gctggtgtca tctttcattg tttcccacct   23100
cttgatgttt aagatagagt ctctcactga acctggagcc ttgcccaatt ggctagacta   23160
gctggccaag caagctggaa ggatactcct gtctacctcc ctagcactga ggttccatgc   23220
gcttctcatg cagtgtttcc atgggttctt ggcatcaatt tcaggtcatc atgtttgcac   23280
agcatgccac tgactgaagc atcttgcagg cccctacttt aaccttcttt cctaaccaca   23340
gttaccatga ctttgcattc tcttcacctg taaaccctct tctcaactga aacaggctag   23400
taaataaagc aaagagagga agaattatcc cacctgtgtt tatcaatcat cacatcacta   23460
tggcaaacac atgagagaaa caacttaaag gaggaggggt tactgtaccc cccacatcat   23520
agagggctca gtccgcggta gcctgaatat gctgctatcg gcccgtggag ggcagaaaat   23580
agtggtggca ataacatgta caactctggc tactcagttg atactgtcaa ggaaaaagag   23640
agctagtcat ggggagggggc ttggaaggag ataacactat ccaaattcac accctcagtg   23700
tcctgcttcc tccagccagc ccaccttctg ttttctacca ctcccaatag tgccatcaaa   23760
ttgtgattcc atcaatgatt aatccagtga ttgggtcact gagaaattat tgggtccacc   23820
agctgagaac gtacagcatg tacactcaat aaacagaagt ttgtatttta ggcagaagta   23880
ccatataggc tcctgacaat cttcagattc taataacact ggccatagat gggaggtttc   23940
taagaactgg tcttgctgaa gtgttacatt tttatcttat aagatacttg tgtcttagct   24000
tagtgaatct ggctgccaga taccttactt tgactaaagc atagtttcgg gaacgattaa   24060
tctttttttt ttttttttttt taccctccat ttcagaattg ctcatgaatg gacccaggaa   24120
tggaaagaat gccctgatta tgtctctgct ggaaaaaaca gctgttactt caactcatca   24180
tatacctcca tttggatacc ctactgcatc aagctaacta caaatggtga tttgctggac   24240
```

```
caaaaatgtt tcactgttga cgaaataggt aagccgtggg ttgctttcat ttgacaaagc   24300
tttagactaa atattaagga agccccaatt tccaagtata atcaagtaga aagactttgt   24360
ggttttaggt atatggagtc tgtctcacag gagtctaaaa gaatagagtc taaaaataca   24420
ggtaacttga ttccagctta aagaagcctg acaatggaac tagagaaatg cccagtgcat   24480
aagagcattg actgctctcc ggaggaccca ggattgtttc ccacccccta catagtagct   24540
aacaacaatc ttgaatctag ggtatctgat accttcttgt ggctccaaac acaaacacat   24600
agtacacaga catgcatgca gacaaaacac ccatgcaaat aaaatacaca aattttaag   24660 ttgaaaaagt agatacctgg tagtagatgc tatgaagaaa ttcatcaggg gctaagagat   24720
ggctctaaag ttaagagcac ttgctgcttt tccaggggac ctgtcatcca tgtggtggct   24780
cacaaccacc tgtgtaactc tagtttcatg aaccttcaaa cctctgtgat atcaggtata   24840
cacatggtgc acacacataa aagcaggcca tacaatagaa tctaagccta gattctcatg   24900
atcacaaaac aaaacaacca tggccacaaa acaaaattta ccaaacagtc ataatcaggt   24960
caaagttgtg tttatatgac ctcaaacaaa cattgatgaa tatttgctcg ggaaaacatg   25020
tcagagagcc atgtggatga ttttttttgct tcccatcctg tgaacataaa gaggaactga   25080
aacaagtaac cataactagg atgtccgtgt ttacagtatg attatacaaa cagcaaaggg   25140
aaagaaagca acaaagggtt ttcagtagct gaccagggtg ctttaagatc tatccacaag   25200
atcccatttt tcctcacgtg aactgtccct tctggcagac aagtgttatt tcttgggcag   25260
caacagcctg gaagacagtg gggaatgtgg ctgactgctg cagacagata gcaagcaaac   25320
catggaagtg tgctttccag agagagggtc gagaaaactc atgggttcta gaggctactt   25380
atttattggc ctcctcccaa ctgcagagct gaagctagac aaggaagtgg tggattagtt   25440
gtaaggacac tggtttaaga gccatgcttt gtccctgcct ctatctgact ctcactgagc   25500
tcttgcatac ctgcgactat actgtatgat acagtcgagt agtggaattt ggcagttcaa   25560
aaaaaatctc agtacagtgt accataacac agtatggtgg gtcctggact tgaggtgttt   25620
ggatacataa aaaacaaag tagtgaccaa atgcatgaat gacctgctat gcctgtagga   25680
ttaagaggag ccagatgaac caaactgtaa cagttcagtt aactcataaa atgtgaatga   25740
tatttaccaa gagtcacaga ccttccagaa actactcagt tctaatattg gtaaaagaaa   25800
aaaaaaaaag aaaagaaagg aaaggaaagg aaaggaaagg aaaggaaaag aaaagaaaag   25860
aaaagaaaag aaaagaaaag gaaggaaag gagaggaaag gaaagaaaag aaaaaagaaa   25920
gaaaagagaa aagaaaannn nnnnnnnnn nnnnnnnnnn nnnnnnnnnn nnnnnnnnnn   25980
nnnnnnnnnn nnnnnnnnnn nnnnnnnnnn nnnnnnnnnn nnnnnnnnnn nnnnnnnatt   26040
gtcaggatat caccagttca gctcacatgg atcaatagcg gtagttcaat ccactcacaa   26100
accccattca gaaccagct atggcagttc tatgcagaag aaaccccag gctctgccac   26160 tcggcccaag tcctagctgc agaagcagga agaagccacc agaacaccac cagaagtact   26220
ttggtgcatt tttctctatg aagtcatgac aaacaatgac cagcaaagaa tggcaaggag   26280
aaccaatgcc atatagtgtc gaccactgtc tggtggaccc tttccaaata gaatatgttc   26340
tctcaagcat acactctaac aaaacatcac atgcccttt tctaggctgc ttccagaaaa   26400
acatcctatg tccgttctta gcaacacatc cttccacatg tctcattcag taaaaacaca   26460
ctctcataac atagtttcca gaaaacatc atatgacaca actgagtctc caaagaaacc   26520
agaaatttcc acttcaaaga catgtagtgt gtaggagtca ggagcagact gctatatttt   26580
```

```
tgatagaggg tctgagcctc ctcctataaa tgctatgtat cacatctatt taaagtagaa   26640
atggaaattt ctataaataa acatgagtga tgaatttcag aaaattttcc atcaaaaaca   26700
tttttaaagc cccaggtata ttgagataac tgtaatccca gcactgtgga ggctgaattg   26760
ggatcatcaa cttaaggcta cataatgaaa tcctttctca aaaatgtata tatactatac   26820
atgtgtatat agataggcag atgtggactg gagaggtggg ccagctattg agagtatttt   26880
ctactgtata actccacttt agaggatttc caatacccte ttctggcctc tgaaggcatt   26940
cattcaggtg gtatatatgt gtacatacag ataaacactc atacacatta aataaaaaac   27000
ttaaaagtat gaggaaagag atgttcatgg ggttagaaaa ggaatcataa aggaacagga   27060
gagtatctta tgggaggagg acaaaaagga gacagtggaa caggaaagca gaagtagaga   27120
ttatggtcat ggaggaaggg aactagcaaa tggaagactc taggaagtga agtaacctaa   27180
tgaaggtgca agatgaataa aaacaatgta tattaatata tacatgtgaa aatatcataa   27240
tgaatgcccc actttctatg ctcactttaa aaagctaatt gaaatgcaca tacacattca   27300
aaactagtcc cttaaaaagt taagcttttct atgggtgttt tgttcccatt tctaagaaag   27360
ggtaaagtgt ccacactttg gtggtcttcg ttcttcttga atttcatgcg tttggcaagt   27420
tgtatcttat atcttgggta tcctaagttt ctgggctatt gtccacttat cagtgagtac   27480
atattgtgcg agttcctttg tgattgggtt acttcattca ggatgatacc ctccaggtcc   27540
atccatttgc ctaggaattt cataaattca tttttttaata gctgagtagt attccattgt   27600
gtaaatgtac cacattttct gtatccattc ctctgttgag gggcatctgg gttctttcca   27660
gcttctggct attataaaca aggctgctat gaacatagtg gagcatgtgt tcttcttacc   27720
ggttgggaca tcttctggat atatggccag gagaggtatt tcgggatcct ctggtagtac   27780
tatgtccaat tttctgagga accgccagac tgatttccag agtggttgta caagcttgca   27840
atccccaccaa caatggagga gtgttcccct ttctccacat cctcgccaac atctgctgtc   27900
acctgagttt ttgatcttag ccattctgac tggagtgaag tggaatctca gggttgtttt   27960
gatttgcatt tccctgatga ttaaggatgt tgaacatttt tttcaggtgc ttctctgccc   28020
ttcggtattc ctcaggtgag aattctttgt ccagctctga gccccatttt ttaatggggt   28080
tatttgattt tctggagtcc accttcttga gttctttata tatattggat attagtcccc   28140
tatccgattg ggataggtaa agatccttc ccaatctgtt ggtggtcttt tgtcttattg   28200
acggtgtctt ttgccttgca gaagcttag agtttcatga ggtcccattg tcaattctcg   28260
atcttacagc acaagccatg ctgttctgtt caggaatttt ttccctgtg cccatatctt   28320
caaggctttt ccctactttc tcctctataa gtttcaggtc tcggttttat gtggagttcc   28380
ttaatccact tagattgacc ttagtacaag gagatagaaa tggatcaatt cgcattcttc   28440
tacatgataa ccgccagttg tgccagcacc attgttgaaa atgctgtctt ttttccactg   28500
gatggtttta gctcccttgt caaagatcaa gtgaccattt ggagctgtga cgaaggatg   28560
gaccatctag tgactgccat atgcagggat ccaccccata atcagcatcc aaacgctgac   28620
accattgcat acactagcaa gatttcgctg aaaggaccca gttatagctc tctcttgtga   28680
gactatgccg gggcctagca aacacagaag tggatgatca cagtcagcta ttggatgggt   28740
cacaaggccc ctaatggagg agctagaaa attacccaag gagctatagg gaactgcaac   28800
cctataggtg gaacaacaat atgaactaac cagtacccgg gagctcttgt ctttagctgc   28860
atatgtatca aaagatggcc tagtcggcca tcactgcaaa gagaggtcca ttggacttgc   28920
aaactttata tgccccccagt acaggggaac gccagggcca aaaaggggga gtgggtgggt   28980
```

```
agggggattgg ggaggtgggt atgggggacc tttgggatag cattgaaaat gtaaatgagg    29040
aaaataccta attaaaaaaa aaagttaagc ttatggttat tcctcaattc ctaacaaatc    29100
caggacaaag taatactgct attgtatagg actatgaagc tcgaatatcc ttcacattta    29160
atttctaaaa tgtattcatg aatagatgta gttaatattt ttaaatgagg aaaatctttc    29220
ttatctctta aatggggggta gggggaggtg tatgtaacag tggccgaaac ataccccttcc    29280 attataggtc tgtgtctact ctgagtcaat gcctctctgg tgaattctag ggatccaaac    29340
tttctaagta gctatgtgca tatgttaaga aataaattaa gttttaattc tgtaccttca    29400
agtagtttca aaaggcttgg taataagccc tatctagtaa cactttgctt gagacatggc    29460
aaaatttaga tataaattgt agctttggga tctataattg actttatcat ctttcttgaa    29520
accctagtct ttatggccct cataagaata cagagatata tctaagaata tgatagagga    29580
ttactagcag aaactgagca aaatgcaatt tcgaattgct cacttgacag ctgagcagag    29640
agagtaagca ctaaattctc tgcttcctgt aacaggccat atttaaaaag tgaagtcttt    29700
ctaactctct acttctttgg ttttttgattt gtgtgtgtgt gtgtgtgtgt gtgtctgtgt    29760
gtctgtcaaa atcctaaagt acaaatgcta tcagagctaa aaataaatac gtagcacaac    29820
aactcttcca atgaatttca gatttgagac taaaagggaa ttagaggaga ttttataagt    29880 attttttttaa atgaaacatc attcttacat ttaaaaatgt tgctctgtta taaagtagag    29940
ttcaatcgat gtggattgtc ggaagaatta ggagtgtggt cagagtgtgg tcaaaatgaa    30000
tgaaatgatt tggtctctga aggaagcaga ctatcactat caagagtgtt tctctggagt    30060
ctaatcaatt ctccattgaa ttcacagtgc aacctgatcc acccattggc ctcaactgga    30120
ctttactaaa cattagtttg accgggattc gtggagacat ccaagtgagt tggcaaccac    30180
cacccaatgc agatgttctg aagggatgga taattctgga gtatgaaatt cagtacaaag    30240
aagtaaatga atcaaaatgg aaagtggtaa gagtcactcc attctataca ttgacttttc    30300
ttctttctaa ttcaatactc actttcttat ttgtaataac actttctttt cacctaggac    30360
tatatttcca aattatgtgc cctataactt gttattagag gaagactgat ataatctcaa    30420
taccttaaaa gtatctaaga caacaaatgc tgatgtgaat cttccatgta gatatatgga    30480
agagtattgg gaggagaaaa ccatttccct agttatcttt ggtgttcagt ttaaccatgg    30540
aacaaggtca cagacttacc actttgctat ctttagagat gtggttgaac ttaactagga    30600
tcatgatcaa ggtcaagagt aggctatggc caaatgttat cccatgactt taatgactgc    30660
tactcataag acctatatta gtatttgttc ttggttctct ccagaagaga ggcacaaaga    30720 aggaattttaa tctatagagg tttcataaag atgttctttt acatacctca gagaaaatca    30780
agctgagagg ccacttcata agggagaaga gagcaaattg gcccgcaaac ctctcacttc    30840
cctgccaagc acttgggaac tcggcactga gataaattct acatggcaca caacaagaag    30900
ggaaacagga ttaccatgcc attccaaata taactaattc taaatcagtc taaccacagc    30960
cacagccctg gccaagtcaa gcagcttctc gataggcatg acgttgtacc cagcacccctg    31020 gcagggtcta ctccccaaat tttgagacat gaggccctgt ctattcagtg tagcaccaaa    31080
aatgaagcca attttgtcat tagcagagaa tacaacttgg ggtgcctcga acagctactt    31140
cttctgttca aagttctgtt ttctaaatca ttctaattta gatatctggt ttatgacttg    31200
gtaccaaaag gggcctggct ggatgttaat tcaaacaagg cttctaaac cgagtcataa    31260 tcaaacactt attcgcccac caaatatagg aacaactact ttgcacaagg taccaagggc    31320
```

```
acctgaggta gcagttttga aaatgagaaa catgtacctc tgaggactct tgagaccatc    31380
tcaagggagc atatgaggtc aacactaatt tcacactaat aacatgtttg ttccctagtt    31440
caaaaacagt ggtaagaaaa ctactgcctc gtggcatgaa tcaagtcagc aatcccattg    31500
tttacagtta cattgtgaag ctcacattaa aggctggggc tgtttcctag gagcctctgc    31560
ttaaatctca gccttggagt gtattgctgt cccagctcct gtggcacatg gagagtacac    31620
actgtactca tctacattcc aaggtaatga aggatcaaaa cacttaaatg cttcagcaac    31680
cagaccagca gctcttttgt atgaagcaca aattttatac gaaggacaaa acacatacta    31740
gtagataatc acttatattt gaattgacaa agatttctca aggaaacatt tgttcttcca    31800
gtgaacatct gacaaggttt gcaccaggga tgttaacctc caggcagaat agagttttta    31860
acaatgtata tctacaacca taatttgcct tccaacgtag taagacttac cccaaaagga    31920
tccattgtga tattagcaaa aatggtggtt ttatgttaga aataaaaatc tgtgaagact    31980
tctgatgctt acatctcagt aaactagatt aaatatttttt tcaaatagcc tgagagtaat    32040
tacactaatc acataatcat atattatgta aaattatcat taattatcat gttaatgatg    32100
ttttgaaata tttatatgtg gtaagatggt tcagcagagc tatgaatgga tatattttttc    32160 acagatgttt ttgaactgac agtttcaaat ctgctctctt gtatattcca aaatatccct    32220 tttttttttct acccatttgt tcatcaaagg gcccaagttg atccatattt tggctacagt    32280
tatcatgatc aggcaaatgt atctttaaca tattaatctt atttccttgg gatataaatt    32340
attaataaaa aaatcactgg atcatatggt aactttagtt ttcattattg agtagcctct    32400
atactctttt cagttgttac tgtgccaatt tttatttcaa taaacaagtt agaaaagcca    32460
tcaacaatct caccctgcta tgaattcttc aagatactgg tcaggaaaca agcccactga    32520
ttgtagtatg aatactacag gaattactac ctactttcta gttagtttta aagccttcca    32580
cacaagatgg aacccatacc tgacatcatt aactgggcca aaacaacatg gctggctagg    32640
ttataagccc tataggagaa atcaatagat agacatagta gttaattgcc tcccccaagt    32700
tattaacact ctactcataa attaatacac ctcctgaccc tcattggaga agcttctctt    32760
ttcaacagag agtagttaat acagagaacc tcattcagtc agtatgcaga gcactcaaca    32820
ctgaatggaa tatccatatc ctacccactc cccccaagat taaaaggtta ttgaggaaga    32880
aatattagaa gtgtctaaag gcctcaatgg ctatagaaaa actatttact ggccacagac    32940
atgcagttac acacacagtt gctggaagtg catgagtaga aggtttacac aagatcatgg    33000
cagccaaatc ccagcatgtt tctgggagag ccttaggacg ctcctccctg cctgagaagc    33060
tcttgacatt gtcagagcta ctgggaagct gggagagact ggatttcttc agggatgtga    33120
gacctgagag gcattccatg ctccagcagg tggccccaca cctatgcaca taaaagcagt    33180
aaacactgag tattttaaaa gagagagaga gagagaaaga gagcagagcc agaacttgtg    33240
tgcctactct aagttgggga agaaaagtac tggataatta aggaaagaa tgggaggtgg    33300 gaggtggatt tgatcaaaca tagacattta tgaatactaa atataatttt tctcattttta    33360 tattagttgg ccattaaaag ccaagtttac aattaaataa aatattttaa aaatatcttt    33420
tctgtcaatc cttttcagta tgttctagt ttcacctgtt tctgctctga cacttgccac    33480
cccctccctt gcttcagtct cctttgagat ctgttttgac ttttactagt tcctagaggt    33540
atagtgattg gtccttgtct ggtgcagtta aaggttccct cagaaaactg aaagatagta    33600
gagaaagaca gagatgggag gggtcatagg ttgacttccg gggttcccta tggattatgt    33660
acaatgttag tgaaatcttt cactaatacc gatgacagtg gctgagaaac caagtcttgc    33720
```

```
tccaagcgtg aaacccaagt ttaaaaatga ctcaataaaa aacaagaaag tgtaaaattc    33780
agagtcctag tctaaagaaa acattttaaa catacaaatc ctggatatat tcagaggctc    33840
ctgtcaggag gcacacccct atcatatgcg catggcgggg aaaaaatact tgtgcataga    33900
aaccaagtgg agtgaaaaac aatttgtttc agatgttgag gtccagctcc taataaaaca    33960
aataatgggg tttatcgatg tgaaaatcta tgctgctgaa aaggtgaaga ttccactttg    34020
ttcttattaa caggaactag gagtcctact cataacatat aaaaaacata ttgagcacca    34080
cgagcatgag tgtttgacac agagcagtga ttttcaatgt tcctaatgct gcacagctcc    34140
tcatgtgtgg tgaccccccaa agatagaatt actttgttgc tattccatga gtgtaatgtt    34200
gctactgctt tgacttgtaa tgtaaatatc actgacttac tggaaaggac tgtgataatg    34260
cagaccttgg gtctgcctct ctaatagcaa tatcttatag agctaatcct cctacgctca    34320
cttcctttgt ctggagaaag ggactatcct aagtttcaaa tctgtgaaac acagatgttc    34380
agtgctcagg gtctccagtg attttctgtc atgtgcattt tcctggggag atgtgaccat    34440
ctagtccctc tagacagagt accaacaaca gatcaaccaa actgtcccac ccacttctag    34500
gttacagaac cagtgaggtg atccactgtc gaaaggagaa cacatgaggt ttacttacag    34560
gtgggctgcg agtgactcac tcgcagccca caagcaggag gatgagcaaa ggnnnnnnnn    34620
nnnnnnnnnn nnnnnnnnnn nnnnnnnnnn nnnnnnnnnn nnnnnnnnnn nnnnnnnnnn    34680
nnnnnnnnnn nnnnnnnnnn nnnnnnnnnn nnatccgtgt ctgcgattga tcacactcca    34740
gcccaccaag caggcaggat gactcacaaa gggtaccttc ctgttgctgc ctacagagtt    34800
cacaggaaga tcagctgatc agacagcctc ctctcctcag caacagttct gtacttgacc    34860
ttgtggaagg cccttgtgag tttattcagg tttctgaaac ctccagcctt ctgagctata    34920
ctgacttcct aagtctgaag attcttccag aaaagtgttt ctgttctgag gacatagcta    34980
cctcacaatt ttctatggac attcttgagc aacagactac tctgaggcaa gtttaagact    35040
tccggagtaa ataaagtgtg tagctgcttt caataaaagt ctttggcagt tcaagacaac    35100
tatggtattt tgaggactgt ttcaaattct gtgattatca ataaatgact tctgcccaga    35160
tttcccaggg aatacatatg ctacagataa atgatttgct tgtggccata atttgttttg    35220
gtgtggaaat atgaggtttc ctgtcctact atatcactcc atacaaaact ataataccccc    35280 agataaatag cataccaata tacctcttac agatctgcca tgcctaattc tattacgact    35340
tactcttagt tgactatttta agaccaaatg caaacatatg gctgcatttt tgatactaaa    35400
ataaatttga ggattattat tttaacaaaa ttatttacat aatttgtctc agtccatctt    35460
atttaatagc caattccttc taggtaggtt caaatattac tcactttcta gaaacccagt    35520
tcaaagagaa aaggaaaaac acttgtagaa tctgtgcatt gagttgttaa tgcctgaggc    35580
aatctgtttt ttatttttgtt ttgaaagatg ggccctatat ggttaacata ctgtccagtg    35640
tactcattga gaatggataa agaacatgaa gtgcgggtga gatccagaca acggagcttt    35700
gaaaagtaca gcgagttcag cgaagtcctc cgtgtaatat ttcctcagac gaacatattg    35760
gaagcatgtg aagaaggtag tgtgtgtgtg tgtgtgtgtg tgtgtgtgtg tgtgtgtgtg    35820
tgtgtgcgtg cgtgcgtgcg cgcgcgcgca tctaaatgac agctagcatg acttttggca    35880
atatatgcta acatatgcct ccacttgtta gtatattgtc taggtcaata tactgtagtt    35940
tcacatatca ggggcaagac attgaagtca ctatctggag aagatgtatg caatgaaaag    36000
gaaacaaaaa gagggggctgg agatatggct cagtggttaa gagcacttcc tgttcttcta    36060
```

```
caggaaccaa gtccaattct cagcacccac atcaagagat tgacaaccac ctgtatcacc    36120
agcttcagag gatccgccat ccctagcctt gtgggcacct gcattcatat gcacatacat    36180
gcatacgcat aattcaaaat aataaaataa aattttaaaa attaacaaca gaatttgttt    36240
ccaaattatt tgatttagga aaggtatcag ggcaggtgga aactcagaga gggtatacga    36300
tggttgtccc tgaacaacag aatttctggg gagttgggtt ttttttttct ttgtatgtct    36360
ctacattccc aattttttc ttcaatgtgg gtgttttgaa tttttatcca gaagaaacaa    36420
atttatctga ggtttgaaga aggaaatgtg atactcatgg gattggagga gtacaggtgt    36480
ggtgtttact tagagaatgc ctagctggaa gtataggaag tcatgtgttg gtcacattct    36540
ggggacacgg gacacacttg gaactcctac acaggagaac aacagagatg atgcagggtt    36600
tctccgtgtc tgtattaaaa agtagttaga ctctgcctct gtggtaagaa tattgggaaa    36660
cgacctcaag ggaactgggg ggacatttag tcctaaggaa aaagatagaa gtgtcataga    36720
caaattctcc cacagctcat aaagtacaga agtatctgaa cagcctcagc acagtgtaca    36780
caaacacaca gtattaaact ataaaaacgt gctctacatg cctaggtata gcacggtgac    36840
tctagcctca taactttgat atatcctcaa tgtggaaact gacagatatc attatgtctt    36900
aaagtattag atggacatcc tttacttagg tttaacaaac aacagttttt ttgttttttt    36960
tttttttttc tggtgctaaa gccctggtga tattccacag acatttggac atatgagaag    37020
cttagaggtt tcaggttttt gcaatgtgtt tgaaacttgc gcttttcatt ttgagttttt    37080 cttttttataa taatttttact ttttaaatta taatataatt acattgtctc cccttcagtt    37140
ttcttccttc aaccccccacc atgtaccgtc acgaccatag gatggccatc acctcacttt    37200
ctcttaaatt tttggcgtct tattctttaa ctgtttatat atatatataa aacatatatt    37260
tatatatatt aaatatgtta tatatgtata tttacacata taaaatatat gtatacacat    37320
gtgcttaaca tgtatataca tataggtaga tgtatacata tatacacgta tatatatata    37380
tgtatatata tatatatatg tgtgtgtgtg tttacatata tgtatttaaa aacagttaaa    37440
gaaaaagaga ccaaaaattt gagggaaagt gaggaagtga tcatcatcat atatatgtat    37500
atatgtgtga catatatatg cttaaatcta tatctacata tatagataga tagatataga    37560
tttaagcagt ggacaagcat gctgtatgct taggaaagaa aaatccgaag ccatcctact    37620
gtgtttccat ggttatgaag ttgaaacttt gccatatgaa ttcagattaa tggatatttt    37680
caagtgggga aggacagtgc cttgtaaact ttgcttgggt tattcatagt tctgtcagtg    37740
aaatattctt tcctgttta gatatccagt ttccatggtt cttaattatt atctttggaa    37800
tatttggagt agcagtgatg ctatttgtag ttatattttc aaagcagcaa aggtaggtgt    37860
gaagcactct ctttaatatg ttttttacaag ttctcatttc catgtgtact ctcgtgtgtt    37920
atttgaaatg ttctcttgta cagcacaagt ggctatctta attaactcag aaaagtttaa    37980
tttctggttt taccttttacc acatctgtac tcagtctgtt gtctgtcgtg tttacctttt    38040
tttaaaaaat ggatgattta aatcaggaag tttaggcaca tcctgtcata ctaaggcatc    38100
atttcacgga catttttgtc agtcttgttt ggttctatcc tagcctctct gagtctgtgg    38160
attttaacat gattatcctt tactttatat taatatccac tcataagtga gttcatacta    38220 cgttgtctt tctgggtgtg ggttacctca ctcaggatga tgttttttcta gttccatcca    38280 tttgcctgaa attttcatga tgtcattgtt tttagcagct gagcaataca ctccattgta    38340
tgaatgtacc acatttcctt tattaattct tctgtggaag gagccttcaa agtctaaaaa    38400
aaaaaaatta tattgtattc tcttggagtc tagagtctac agctattcag ccactgccat    38460
```

-continued

```
ttgaacttcc ttgtaccacc taacctctct gaaaatctac atctgtgtgc tcaacaggat    38520
cttctaaatc actttgaata acaaaatgcc attttcctc ttggaaaaaa acttagattg    38580
cagaaaatgt tttatgcagc atgctgcggg gggcggggggg cgtgggacat tgctatcatt    38640
tggcctttgt ttgcacttaa catagtttca acaccatttg tgatcatgag ctttctagga    38700
ataccacttt caagattcca gaattcagtt ggtctttgca ctataagccc tgtgtgtcct    38760
gggaagttcc tcagttctgg gccaccaata gttggttggt ctatctaaac ttgaaatcaa    38820
gctgttcaac tgaagtcaag aggcacttag tgactcaaaa tggaatgtag gaacaaatat    38880
atggtatagg cctttagttg ttgtagtaat ccagcattca cacatctcaa aattagccat    38940
tttaataaaa atgtgcagaa gaaattcagg taatgccatc aaccttcaac tgaataaact    39000
tcattttcat cagggtttca ccatcaatat cataaataaa tgaggggaa aaaactcgct    39060 gcataatttt atttgaact tagctttta gccacattct tgttttgca gaacatatac    39120 tacagttgaa acaacagggt tttcagttgt ttgaggaaag taaatttatc tttagagttt    39180
taagtaagac atgagcttga ataaggccaa ccagagtcaa attaattgat tttagttcat    39240
tagtctatag agctagtgaa attgcaaatt ttatatggaa ctgtagtaaa taaaattgct    39300
ttgtacataa aactattcac cctaataccg ttcatttcat gtcacaaagg ccggaccgag    39360
tgatgatctc nnnnnnnnn nnnnnnnnn nnnnnnnnn nnnnnnnnn nnnnnnnnn    39420 nnnnnnnnn nnnnnnnnn nnnnnnnnn nnnnnnnnn nnnnnnnnn agtaatgagc    39480 cggacccata gcagcataga gtggatagca tagtcagaca gctggcttgg agcatcactc    39540
tgggcctgaa ggcagcccac caagggtctg tataatggag agcacagata atatcatctc    39600
cctttcctgg tgtgtaagga ttgatgaaag tttaatgcaa gagccgatca tctgatctat    39660
aaataatcat gtggtgaggt tttagggacc atatctgtat cacaactgtt ccaatgacgt    39720
atagaagcat tcagagataa tgtgttgggt ttaaggataa acactggtta gctagtaaca    39780
gaaagatggt ttatgtaaat ttattcaaga aatgttatgg aacaacttcc atgtgctaag    39840
taatataatt ccaacaagag acaaatctgt agaataaaca ttgaaattaa ctacagtcaa    39900
aaacaattat ttcagggctg aaagcagtag ttcagcaagt gagagtgtat agcgctcttg    39960
tagaggagtc aagttcaatt cccagcacct atatggggtg gctcacatct gctgtaaccc    40020
tagctcgtct gccctcccta ggtacctact cattcatggg atataatcac agaaggacac    40080
ataaaataaa aataaaatga taaatcttga gggcggttac atggaagagg ctttatttag    40140
agagggcaac tgggagtggc tataggaaag aaaggagata attcaatttc agttaaaaat    40200
attagtaata gattttttaa agaaaaaata atttcaatat ttgaaagaga aaatgtcaat    40260
acatcttggt attatgcata caattctacc cttattagag atgattcagg ttagtctgtc    40320
ctattttaag taatacaggc actatcatgt tggctagaag ttatcatcaa tgcttttgg    40380 ttactatgga ctgtgtagtg cttagcccag tgtagtgctt agcccaaccc attttttca    40440 agtttgaaaa taattttggt tccattttat tgattgtctt gttttctatt tggtgttaca    40500
tgctttaaaa gtatcttatt tgtatcttat ttataagtta catgaaagct ggctttagac    40560
agaattagac tcctcactgc caagtactaa aattgaccac tcatcaatag cactaaaaaa    40620
aaaaaaagag ttaaccatg acttagctaa atgatcttaa acgaaggcct ttgggtgatg    40680
tttttctcct gaaactttg ccacctactt cctgcttaga actctccctc tcttttgaat    40740
attctgctta tacaagatat aagaatgcct agaataagtg atagtactgg caatatttca    40800
```

```
ttctaccttt ttgagataat ttttaagatg taaaataaag atgtagaaat aacactttat    40860
ttgtttccaa ggattaagat gctgatttta cccccagtcc cagttccaaa gattaaaggg    40920
attgatccag atcttctcaa ggtaactaag tctacattgt ggatcattca attaagtagt    40980
acctaaagaa tactatctat cttctgttgg gagggqtggt ggtggttggt tggttggttg    41040
ggtttgttgt tgactttggt ttttttgggt tttggagtgt tttgatttt ttgtgtttgg     41100 ttagttggtt tggtttagtt tgaaatcaca atgcatccta tctaaagtta tataatggtt    41160
ttttgagttg cttttcatag atctccactt tctctctgcc tcctaggaag ggaagttgga    41220
ggaggtgaac accatcttag gcattcatga taactacaaa cccgacttct acaatgatga    41280
ttcctgggtc gagttcattg agctagatat tgatgaagca gatgtggatg agaagactga    41340
agggtctgac acagacagac ttctaagcaa tgatcatgag aaatcagctg gtatccttgg    41400
agcaaaggat gatgattctg ggcgtaccag ctgttacgac cctgacattt tggatactga    41460
tttccatacc agtgacatgt gtgatggtac cttgaagttt gctcagtcac agaagttaaa    41520
tatggaagct gatctcttgt gccttgatca gaagaatctg aagaacttgc cttatgatgc    41580
ttcccttggc tctctgcatc cctccattac ccagacagta gaagaaaaca agccacagcc    41640
acttttgagc agcgaaactg aggcaaccca ccaactcgcc tctacaccga tgagtaatcc    41700
cacatcactg gcaaacattg actttatgc ccaagtaagc gacattacac cagcaggtgg     41760
tgtagtcctt tccccaggcc aaaagattaa ggcagggata gcccaaggca atacccagcg    41820
ggaggtggcc acgccctgcc aagaaaatta cagcatgaac agtgcctact tttgtgagtc    41880
agatgccaaa aaatgcatcg ctgtggcccc tcgcatggaa gccacgtctt gtataaaacc    41940
aagctttaac caagaggaca tttacatcac cacagaaagc cttaccacta ctgcccagat    42000
gtctgagaca gcagatattg ctccagatgc tgagatgtct gtcccagact acaccacggt    42060
tcacaccgtg cagtctccaa ggggcct tat actcaacgca actgctttgc ctttgcctga    42120
caaaaagaat tttccctcct cgtgtggtta tgtgagcaca gaccaactga acaaaatcat    42180
gcagtagcct ttcctatctt taatggcaag ggaaaggctg ggcacaaacg cttaaaccaa    42240
aactatgttt taaatctgtg ttgggagagc atgagagtgg atatggattc taaaatactt    42300
tttctggaaa tgtcaaaata tcataaagtg gaaaatcaag aattcgtaat cagataaatg    42360
ctcccattgt gaattataaa tatttaatg aattgtcttt aagactgtat agtggcagtg     42420
attgtctgta ctgtgggtct taattttgtg atactaagca ttaaatagct acgttttta    42480 tgtatgtaga tcatgctttt tgaaaaagca aacaatcagg tggcttttgc agttcaggaa    42540
attgaatgca gattatagca caggctgatt tttttttct ttttaaata actgggaact      42600 aaaactctag gtgagaaggt aaaactagtt tggatatgca aaacatttat tttgacatga    42660
aattgataaa gatatttta ataatttaca ctttaagcat gagtacttta taatatgcta     42720
cacacatatt gtagttcaga acaatccatc taaggatgta gcagctacag tgtaaagagg    42780
gtttcatgtt ttggtcaatg aacgtaaaga aaaccaaaca agttagattt ttacaaagcc    42840 ctttttataac ttccaaaact tcttaactct aaaaatgtct aataacctgc attattagaa    42900
aaaacatttt taaatttgta aacgaatatt tttttaattt tgaaaacttt attttttttt    42960
aatgttgaat caacgtatca tacaccaaac agtaaacaga aattataata atggaagaag    43020
tgctttcttc gacaaatttc cattcaagcc acacagctac atgtaagaga agtagaagtg    43080
atgtggtgtg attggctagg atgcagaaga gcttcaggaa tacaagaagt gagagcccaa    43140
ggattgggag gaggggctc tcacatctcc acagtgcagt ctgtcaaacc cagcttggtt     43200
```

```
tttatagtat tctaagaatt attgtgtaca aggaaaagtc tcacatgtat gaaatccagt    43260
atccagatgg ggtaaagtta gcagataata ggataggaaa ttaaagacct agatctttt     43320 tcacagacag acacaaattt ttaattcagg gagaagggac agaataaatg acttcccact    43380
cacaaagcac aactcagaag taattaaaca ggtaacagaa accttgccat caaacctttg    43440
ataagatgta ttttaagtag taagcagtat ttcaatgctt cttacttacc ctcccaggac    43500
aaccgatctc aaataaggga gataaggtag ataaaaatca cttttttgatt ctgtaataac   43560 ataaacatag ttctttgggt tagcaccccc cccaaaaaaa atttatggga gaagaggac     43620 tctcagctga ctgaagaata catctcattt aaatattttt tagatgcctg aaactttaaa    43680 attacccttta agttttaatg gtatttacca ttttgccaag acctttgtgg ggaaacaagc   43740
ttaatgttta gtgattttga aatctctttc atgcaggaga gacagtgaaa atctagcctt    43800
gggtgtttaa ggttcgcctt gttactttgt aatagatttt aataagtttt tctgctactt    43860
tgctgctatg gtttctccaa tggctacatg atttagttca tatgaagtat catcaactta    43920
gaatctattc agcttaaaga tgtgtgtttt gatgaactat cttaccattt caccataggc    43980
tgaccacgtt tctatagcca aaaatagcta aatacctcaa tcagttccag aatgtcattt    44040
tttggtactt tgctggccac acaagccgtt attcaccgtt taactagttg tgttctgcag    44100 tctatatttta actttctta tgtctgtgga ttttcccctt caaagttcaa taaatttatt    44160
ttcttggatt tctgatctta tgtttctaat agccttgaag cacaattacc tagacatgta    44220
ctgagactaa ctgtaaagga cgtagatgag ttcatttaaa tgcatcagtg aatagtggat    44280
cgtggatcac aaagcggcag aggagcaggg tgtggttaag atagtctttt tctttttatgg  44340 actctgcctt ctctttagga taacactcat gtggacagag acttacagat gctttgaaca   44400
catcctaaaa gttaaatggt gtgtccaagt tgatgggaa ttgtgggaaa tggaagagg     44460 agcgttgtct ctaaactaca tttctagctt gagtgtgtta tctgccattg ggaagagtgg   44520
ttctccctgg gcttatgtat tgacagagtt cttcattctg atgactcgtc atcataagag   44580
actgacaatg agtctctata ctagttgctt ttctaataat tgcctgaata agcaacttag   44640
ggacaagagg tttgtcatag ttcccagttt agagggtggg aaaggcaggg cacctggagt   44700
ggcctggctt gtaacagtgg gaacttgcaa catgacttgt ccacatcttg gaggataagg   44760
aaacagaaag ctccagctag aactaaaggc aaatatgact ttcagttccc accccagct    44820 acttggcttg tcagatatat ccctaaaccc aaaggttcca caactcctaa tacagagcca   44880
tcagcttgac accaggtctt caaacacggg agcctctgaa agacatttt ctattcaagc    44940 catatgtaag tttcttcctc ctgggaggaa ggttggttag gcaggttgtg tggctcagct   45000
cgagatggag aggcttagat tcttacttca ggtttcaagt ggtgaattac atgctctcag   45060
gcatgcatta aggcctagga ggtagaaggc tgacattgga attacccagc cactggacag   45120
ctgtttactg tttcagccag tttcccaagc tgccaagact gtagagaata cttggtgact   45180
acattctatt taaaaaaaaa caaaaaaaca cacaaaaagc tgagcagtgg ttgtgcacgc   45240
cttcaatccc agcacttggg aaacagaggc aggtggattt ctgagttcaa ggccagccta   45300
gtctacagag tgagttacag gacagccagg gctacagaga aaccctgtct acttcaagca   45360
cctgatatcg attgcctaca ggtgctagac aagacccaat cttctgaaga ggacctgtct   45420
atttcagaag attgatgact cgtgattatg tgtatctgtc tgttcttaaa tattgtgata   45480
attcgctcta ccaagatgtg tactaacaga aaatatttac atgttttat agaaaaaaaa    45540
```

```
gtttgacagt aaatttattc tagtaagaaa tcacatccaa gctgggtggt gtagtggcac  45600
acacctttaa tcccagcaca caggaggaag aggcagggag atctctgtga gttcaaggtc  45660
agcctgttct acaaggtgag tttcaggaca gccagaccta catctcaaca gaaaaaagaa  45720
aacgggaaag aaatcacaag cataaaagct agagatggtt tcaagctaaa ctcttgttta  45780
aaattcaagt tcttacataa tatgtcccca gttgcctttg ccaattttat atttatgagc  45840
tgggtataaa gggcaccatt tacaaataag aatttgagct ttgctaacat cactttcttt  45900
ggaaaactaa taggtatatt gtgtttacct tgttatatgg gtaaaacccc ttatggttaa  45960
aaggattcct cccaggtaag ttcagtttga atggactgaa acgataaaat ctagagatac  46020
gctagacttt agacttgagt acgactcttt tttttttttt ttttttttt gtaaaaaga   46080
tatttatttc tcattttgtt agcatttact gaggacaatc atgacacagt tctactttac  46140
aaaactatca ggaagtaaca atttgacgtt catgtgaact ataattacct actttcttc   46200
ttctacaaca tgtacctcag agacaggatg acaggccaag aagaacatga tataccacct  46260
gacattaata gcaagcacat gctttcaaaa gaatttcaca ataacactta ttcaaaaata  46320
tcattttttga ttctttgact atttttataac acctcagaaa ggattgtcta tttttacagca 46380
aaggtgtgac aagaatttat tgggtaaatg aattcaaaat tttaatcaca agtaagtagt  46440
ctagagttag catgtacaaa gcttcatttc tgcccatgag tcccaaagtg attcccatga  46500
ttccaaagtt gtccctctgg cagagtcatg attgttcttt ttttaatatt tttattacat  46560
attttcctca attacatttc caatgctata accaaaagtc ccccataccc tccccccac   46620
ttccctaccc acccattccc attttttttgg cctggcattc ccctgtactg gggcatatac  46680
agtttgcatg tccaatgggc ctctctttcc agtgatggcc gactaggcca tcttttgata  46740
catatgcagc tagagacacg agttctgggg gtactgatta gttcatattg ttgttccacc  46800
tataggggttg cagacccctt cagctccttg ggtactttct ctagctcctc cattgggagc  46860
cctgtgatcc atccaatagc tgactgtgag catccactta tgtgtttgct aggccccagc  46920
atagtctcac aagagacagc tacatctgag tcctttcaat aaaatcttgc tagtgtatgc  46980
aatggtgtca gtgtttggaa gctgattatg gggtggatcc ctggatatgg cagtctctag  47040
atggtccatc ctttcctctc agctccaatc tttgtctctg taactccttc catgggtgtt  47100
tgttcccaat tctaagaagg ggcaaagtgt ccacacttca gtcttcattc ttcttgagtt  47160
tcatgtgttt agcaaattgt atcttatatc ttgggtatcc taggttttgg gctaatatcc  47220
acttatcagt gagtacgtat tgtgtgagtt cctttgtgaa tgtgttacct cactcaggat  47280
gatgccctcc aggtccatcc atttggctag gaatttcata aattcattct ttttaatagc  47340
tgagtagtac tccgttgtgt agatgtacca catttctgt attcattcct ctgttgaggg  47400
gcatctgggt tctttccagc ttctggctat tataaataag gctgctatga acatagtgga  47460
gcatgtgtcc ttcttaccag ttggggcttc ttctggtat atgcccagga gaggtattgc  47520
tggatcctcc ggtagtacta tgtccaattt tctgaggaac cgccagactg atttccagag  47580
tggttgtaca agcctgcaat cccaccaaca atggaggagt gttcctcttt ctccacatcc  47640
tcgccagcat ctgctgtcac ctgaattttt gatcttagcc attctcactg gtgtgaggtg  47700
gaatctcagg gttgttttga tttgcatttc cctaatgatt aaggatgttg aacatttttt  47760
caggtgcttc tctgccattc ggtattcctc aggtgagaat tctttgttca gttctgagcc  47820
ccatttttta aggggttat ttgatttct gaggtccacc ttcttgagtt ctttatatat   47880
gttggatatt agtcccctat ctgatttagg ataggtaaag atcctttccc agtctgttgg  47940
```

-continued

```
tggtcttttt gtcttataga cagtgtcttt tgccttgcag aaactttgga gtttcattag    48000
gtcccatttg tcaattctcg atcttacagc acaagccatt gctgttctgt tcaggaattt    48060
ttccctgtg  cccatatctt caaggctttt ccccactttc tcctctataa gtttcagtgt    48120
ctctggtttt atgtgaagtt ccttgatcca cttagatttg accttagtac aaggagataa    48180
gtatggatcg attcgcattc ttctacatga taacaaccag ttgtgccagc accaattgtt    48240
gaaaatgctg tctttcttcc actggatggt tttggctccc ttgtcgaaga tcaagtgacc    48300
ataggtgtgt gggttcattt ctgggtcttc aattctattc cattggtcca cttgtctgtc    48360
tctataccag taccatgcag tttttatcac aattgctctg tagtaaagct ttaggtcagg    48420
catggtgatt ccaccagagg ttcttttatc cttgagaaga gtttttgcta tcctcggttt    48480
tttgttattc cagatgaatt tgcaaattgc tccttctaat tcgttgaaga attgagttgg    48540
aattttaatg gggattgcat tgaatctgta gattgctttt ggcaagatag ccattttac    48600
aatgttggtc ctgccaatcc atgagcatgg gagatctttc catcttctga gatcttcttt    48660
aatttctttc ttcagggact tgaagttttt atcatacaga tctttcactt ccttcgttag    48720
agtcacgccg agatatttta tattatttgt ggctattgag aagggtgttg tttccctaat    48780
ttctttctca gcctgtttat tctttgtgta gagaaaggcc attgacttgt ttgagttaat    48840
tttatatcca gctacttcac cgaagctgtt tatcaggttt aggagttctc tgttggaatt    48900
tttagggtca cttatatata ctatcatatc atctgcaaaa agtgatattt tgacttcctc    48960
ttttccaatt tgtatcccct tgatctcctt ttgttgtcga attgctctgg ctaatacttc    49020
aagtactatg ttgaaaaggt agggagaaag agggcagcct tgtctagtcc ctgattttag    49080
tgggattgct tccagcttct ctccatttac tttgatgttg gctactggtt tgctgtagat    49140
tgcttttatc atgtttaggt attggccttg aattcctgat cttccagaa  cttttatcat    49200
gaatgggtgt tggatcttgt caaatgcttt ttctgcatct aacgagatga tcatgtggtt    49260
tttgtctttg agtttgttta tataatggat tacattgatg gattttcgta tattaaacca    49320
tccctgcatc cctggaataa aacctacttg gtcaggatgg atgattgctt taatgtgttc    49380
ttggattcgg ttagcgagaa ttttattaag aatttttgca tcgatgttca taagagaaat    49440
tggtctgaag ttctctatct ttgttggatc tttctgtggt ttaggtatca gagtaatagt    49500
ggcttcatag aatgagttgg gtagagtacc ttctacttct atcttgtgaa aaagtttgtg    49560
cagaactgga gttagatctt ctttgaaggt ctgatagaac tctgcactaa acccatctgg    49620
tcctgggctt ttttggctg  ggagactatt aataactgct tctatttctt taggggatat    49680
gggactgttt agaaggtcaa cttgatcctg attcaacttt ggtacctggt atctgtccag    49740
aaatttgtcc atttcgtcca ggttttccag ttttgttgag tatagccttt tgtagaagga    49800
tctgatggtg ttttggattt cttcaggatc tgttgttatg tctccctttt catttctgat    49860
tttgttaatt aggattttgt ccctgtgccc tttagtgagt ctagctaagg gtttatctat    49920
cttgttgatt ttctcaaaga accaactcct cgtttggtta attctttgaa tagttcttct    49980
tgtttccact tggttgattt cacccctgag tttgattatt tcctgccgtc tactcctctt    50040
gggtgaattt gcttcctttt tttctagagc ttttagatgt gttgtcaagc tgctagtatg    50100
tgctctctcc cgttttttct tgaaggctca taactatgag tttccctctt agaaatgctt    50160
tcattgtgtc ccaaaggttg ggtacgttgt ggcttcattt tcattaaact ctaaaaagtc    50220
tttaatttct ttctttattc cttccttgac caaggtatca ttgagaagag tgttgttcag    50280
```

```
tttccacgtg aatgtggctt tccattatta tgttgttatt gaagatcagt cttaggccat    50340
ggtggtctga taggatacat gggacaatct caatatttt ttgttaattt tttaatgatt    50400
aattgtgaat ttcacatcat gtaccccaat tacactcatc tcccccatcc cttcatatct    50460
gccttgcatc cctcctaagg aaaacaaaat ataaaaataa aaacaacaaa aaggagaaaa    50520
acaccatttt aaacaaacta agaaaaagtc atctcgctgt agtgtgataa gtatactctt    50580
ctgtctgtac attttaactt gaaatgttca tggaatgagt cattggtctg gttccctctg    50640
aactccctct tatttgaatt ttattcttaa gattctctct attctaatgt ctttagtact    50700
ctttagtgat taacacaggc ttttaatata tactctgaat ttttctttat ctttataaaa    50760
ttatcatgta taacattttc cttttttct gagttgaata aaattctttc ttactggaac    50820
ttctatgaga tatatgttga agattatcaa cctgtattcc attaatggta actgctcatt    50880
cagatgtttc attgaaattg tcctcatttt gaaataggaa ataaacctat aattgcagtg    50940
tctggtacaa agaagcagat caaattctaa gcttccagtg tcacattgtc cagcagctct    51000
ggcactggtt atattttaaa gtcatttta aggtacactt tattattgga tattttcttt    51060
atttacattt caaatagtct ccccttccc tatccccccc agaaactccc tatcccatcc    51120 cccttctcc tgtttctatg agggtgtgcc cccacccact cactctctcc tgcctaccct    51180
catattcccc tactcggggg aaacaaacct tcatgggacc aagggtgtct tctcccattg    51240
atgcctgaca aggccatcct ctgctacata tgcagttgaa gccatgggtc cttctatgtg    51300
tactccttgg ttggtggttt agaccctgga agctctggtt ggttaatatt gttgttcttt    51360
ttatggggtt gcaaacccca tcagctcctt cagtccttta actaacacct ccattgggga    51420
cccagagatc agtttaatgg tcagctggga gcatccgcct ctgtataggt caggctctgg    51480
cagagccata cacttttttat tgggtaccta gtttgaacca agagaaatat aaaatcctaa    51540
agtattctga cctcagcata acaagatcaa ttcagctgat taaaatgtct tctattgttt    51600
cttctgtttt cctcatctct agcaactata aataacagat ccctaaaatg aaatgtgtac    51660
aaatccagag aacaaaagga gggactgtca acaatgagga gtccaacaaa gagtgacagc    51720
aagcagtttt agatagttta caagaaatgt ctaaaagaat atccagctca acaacccta    51780 aatttctgcc cactaaaaca atgtcagatc attatttctt taaatgtcaa taaggagag    51840 gggtaattga gatagcaact gtaactgtga aattgagata tcctgttagt atgacatgag    51900
tagagatttg tacagatgaa tgacctgagg aaaacgtctc atcaattcta cctctttgtg    51960
cagtgatatt gcttctggaa aacaactgtt agagaagaag tagaaataca ccagaactcc    52020
atcctccacc accccagaga tgattattgt gataatcctc atgttactga aaaactggca    52080
atactcaata tcaataaacc cacaaaagtt ttaattatca gatcctaaca tgaaaaccta    52140
agtgcaaata gacacacagg cattcaaggt ttcacgtgaa gaaactgatt gttctcttcc    52200
attcatttaa atacatgaag aacaacagat gttgggttta acccgttgaa agatgagttg    52260
tggctcacag ttgaaaaatg actgtcctaa atagcaggtg gtcaatacat cgtgaaatat    52320
tagttaatat ggtcattcaa tgttatgtcc ttagttttct gtttatatgg tggcatgagt    52380
gggagatgct acatttcttc ctccagtgag aaggagaatg ctttcaggca tataatgacg    52440
attttttttt tcctgtaaga tacataactc tttgcatctc ctacctccca caccagccta    52500
tcatggatca ttaacggatt ctgtgcattc ttcttaaatc ctctccccat atcctttgca    52560
agttctgcaa gtagatagga tgttttttagg tgatccagtc tgcagcatcc cttttttaatc    52620 agccttttcat gttaagattt tattcttggc atattcagat aatatcaaca aagctgagct    52680
```

```
gatttcactt gaattaacaa agaacaaaag gcctttcta gaaatgaggg tgacaatata    52740
tccagtatgt attgaggaga ttctaataaa aatgaaacaa aaatcaaaat aaaaaggaaa    52800
actatttaat ataaagccct tctttcaatt ttctttacac attttattag aaaatacctc    52860
ctctgcctcc tcaccttcct tcctctctcc ccatacatcc acaaatgtga ttgctaaatt    52920
tctgtgtacc caagtgtgca tttataatga taaaaagatc aaaattgact ctggaaaaaa    52980
atgataggtt tgtaaacaga tttcttatat ttctattata atttagctca tcttcttgaa    53040
atgtgcccaa ggctacaatt ctgtttgaaa ctggagatat cagtttgcac tgctcaggtt    53100
gtctcagagt acactacttc atgttcaagt ggtttgtagg gagccagtac agaaacctaa    53160
aaggagctac agaccaggct cattttcttg atgtcttctt tcttgttctt ctagtctaat    53220
ttttgtgtaa tttgatgaag ccactagtag cttcagattt aaatctgcca tttggggtaa    53280
tgtggggcag aatgtcatct attttcttta ttaagccaaa gtaacattct tatctaacaa    53340
gaactttgcc tctgtgaagt ctaataattt cccctaataa aactagtccc tgaccaaaaa    53400
aaaccctact gagaagttct aactaatcca actatatctg acttcaacac tataatggga    53460
tttatctctc ccttgaaaca aatgttattc ttgaagattt attaaaatgc agatgcaaac    53520
acttaggtgc attgtctttc aatgagtatt tgggcaacat tcttttaaat tttttattag    53580
gtattttctt tatttacatt tcaaatgcta tcccaaaagt cccccatacc ctcccccacc    53640
cactctccta cccacccact cccacttctt ggccctggtg tttccctgta ctgaggcata    53700
taaagtttgc aagaccaagg ggcctctctt cccaatgatg gctgacgagg ccatcttctg    53760
ctacatatgc agctagagac acgagctctg ggggtactgg ttagttcata ttgttgttcc    53820
accaataggg ttgcagaccc ctttagatcc ttgggtacgg tattagtcag ggttctctag    53880
agtcacagaa tttatggata gtctctatat agtaaaagaa tttattgatg acttacagtt    53940
ggcagcccaa ttcccaacaa tggttcagtc gcaggtatga atggaagtcc aaggatctag    54000
cagttactca gtctcacaca gcaagcaggc gaaggagcaa gagcaagacg cccttcttcc    54060
aagcagaagg tgtagcccag attaaaggtg tgttctacca cacgcttaat tccagatgac    54120
cttgaactca gagatttaat cttctggaat ccactatgcc tcaagatctc cataccaaga    54180
tccagatcag aatcttctat ctccaagcct ccagataagg gtcactggtg agccttccaa    54240
ttctgtattg tagttcattc caaatacagt caagttgaca accaggaata gccactacag    54300
gtactttctc tagctcctcc attgggggcc ctgagttcca tccaatagct gactgtgagc    54360
atccacttct gtgtttgcca ggcaccggca tagcctcaca agagacagct atatcacggt    54420
cctttcagca aaatcttgct ggtgtatgca atggtgtcag catttggagg tggactccag    54480
aaaatcaaat aaccccccaa aatggggatc agagctaaac aaagaattct catcttgagt    54540
aacattttaa ggtatgttgt tacacaaatt tttgcactcc tttctcctta tcttacactg    54600
gaatctaaaa aggagagaaa gttcccttc aaggataaat taggaagatc tagaactaca    54660
tagtagatta tctaagatca cataacatcc aatccagtag gagaagagaa ggagatgcgc    54720
agtctacaaa attatatgcc acttgtactc atgacttgct agcttggatg tagtcttatg    54780
actacagtca gctacaaggt tctctgtgaa atggcttta ctgggtccta ttgctaattc    54840
aaattagaaa gtgtcaataa aactggcaat tagtaactta gagcatgtca tagacggcta    54900
tatcaatcct atgagtaaag tcatttaaat gtttattcaa aaggttgtca tgttaataac    54960
tgtgattcat gtgtgtgtgt gtgtgtgtgt gtgtgtgtgt gtgtgtaaaa atatgaattg    55020
```

```
gagaggatta ggaaagcatt cttcaagtcc aatttagaat gttggctagg acttgggcat    55080
ttctagtaga gaagataaca aaaatataat ggactcaaaa ttagctgaaa tggcaacttg    55140
aagatatgat aggcaatgga ggcaaagcct cttgataaca tgtagacttc tgatatgtaa    55200
tgcaaactct ggagacaggt atttatgggt acttgagttt tgttttagaa ttgtgtttca    55260
gaggcctcta ccatgctatc ggtttctgtc tttccaaaac atgatttgaa aaacaatcaa    55320
tcacaattct caatgctatc actgttaact attcccatga acactctttt tgaggctatc    55380
cttaggctct tcgttctatc cttagggagt ttgaatgtat caaacatcac agaatgctga    55440
atttcatact tcaaaaaggt aagctgcatg aacaggtcta atacccagca cattaattct    55500
gtcaacagga atggatcaca actgtcttcc tgtggtatta gtgtggacag gactgtcact    55560
cacatagtga aatgttcgtc tcacagtctt ctgtgtggag ttatttagtc ctaatgacaa    55620
ccatgaatgt tctaactaca tgagtagtta aagaaccat agcaaaattc cagaccgggg     55680
aagtcatcct tttcatttgt attgctcata tatgtatttc actaactact tggtcctttg    55740
taacatttct tgactcatga cctttttta aaatctgaaa tagctcaatc ataacataat      55800
ttaaaaaaac atccaacagg caaagcatgc tggtgcacat ctgtatttag agcatgctgg    55860
tgcacatctg tatttagagc actcagcaac tggaggctga agccagagga tgaggagttc    55920
aaggtcattc tgggctacag aacaaacact ttcttgggaa attttctcag agagagagag    55980
aactaaatca aataaaaaac atattatcta agtgtatgct cctcaattaa ttattcttta   56040
attaacattg gtgcactgaa cattggtgca ctgaaatgaa gaagaaacc aatgtttaca     56100 gaacatacta caggtattcc agtaaaagac actgctacaa tgaatggtta aatgtatacc    56160
atagaatgaa atagactagg attttttaatg catattggta tttcagaatt tgttttgca    56220 tttatttctt ctttaaaaaa tattcaatgt tctgcactct gaggccttgg taaacttaaa    56280
ttcagtggac ttctcttctt actcttctta gagatgtcac aggaccagat taaaattaca    56340
cagttatacc taggtggtgt tggtacaccc ctttaatctc aatatttgag acaaagacag    56400
gtggatcttt gagtttgagg ccagcctatt ctacagagtt ctagaacagc cagggctac     56460 aaagagaaac ccaatcttaa aaacacaagc aaaaaaaaaa aatccaaata ttatattcaa    56520
tttacttaga tgaaaagcat aatctgcctt gagtttaaca ttcaagtctc ttaaatgatc    56580
ttgtggtctc aggtagactc tagcccaggg gtggccttca cttcagctgg aagcctctaa    56640
aaatattctg ggcaaagagc agcagctgca ttagatgaag caatcatctg ggacaattga    56700
tacactcttc tggaaccagg tgtgtgtgag agagtgggag agaccacaag atagaggatt    56760
attaatttat ggggattttg gggagattta tatacccaca caacaacttc tagaagctac    56820
tgaccaagac gcaccaagaa ataaccagga aacgtctaca aaatttcaac cctagcttct    56880
ctaccagatt ttaactaaac gagatcttct tgcaaaggta aaataactgg agggaaaaaa   56940
aaagattctt gacatacatt ctgaaaaaaa ttataagaat atccagcctt gatttcagag    57000
gtatctatag gactatggtt tgtattcttg tgtagttacc tttgattaag tctaagttaa    57060
ttttttgatt gtctctaagt caagtcaggt ctctgcacta ctcctatgtg cttttacatt    57120
tttgaaaaat aaatttctaa ccaagctaag cttggattta tgcgctgttg ttgttccagt    57180
tgttgacttc tcctttaacg agatctctct gtatccttcc tccctcttag tcaactcttt    57240
tccaagtgtt agagaagcct ttgactgctt gctccttta tcactgaatt tgggcttcta    57300
aaatctatcc aacagaagaa gggtgagttt cttgagcatt actctgtgaa actggtccac    57360
ttgaagagat taaggtttga aatgcctccc tttggtcctt tagcattagt gaatcttatt    57420
```

```
gtgtgaacag cttcttgtaa tatcttgtaa gttaggttga caagttgtgt gagacatagc    57480
ttttaccag                                                             57489

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
tgcttggcag ctcgtgggtt                                                    20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
atggctgcgc ctgcttggca                                                    20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
tacctgagac ctcggagttt                                                    20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
acaaagatcc atacctgaga                                                    20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
gctggtgtag cctcacttcc                                                    20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
tttgccaaga gtagctggtg                                                    20

<210> SEQ ID NO 107
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
acgacacttg gtgaatcgag                                                 20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
tggctttccc ttttagcata                                                 20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
atgagcaatt cttgcagctt                                                 20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
agttgaagta acagctgttt                                                 20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
agtagggtat ccaaatggag                                                 20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
gtccagttga ggccaatggg                                                 20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
```

-continued

```
gaattatcca tcccttcaga                                           20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gtactgaatt tcatactcca                                           20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
ctgaactcgc tgtactttc                                            20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
aactggatat cttcttcaca                                           20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
tgctactcca aatattccaa                                           20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
gctttgaaaa tataactaca                                           20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
atcagcatct taatcctttg                                           20

<210> SEQ ID NO 120
<211> LENGTH: 20
<212> TYPE: DNA
```

-continued

```
<213> ORGANISM: Artificial Sequence
<220> FEATURE:
<223> OTHER INFORMATION: Antisense Oligonucleotide

<400> SEQUENCE: 120
tgagaagatc tggatcaatc                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
ttgtagttat catgaatgcc                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
catcattgta gaagtcgggt                                              20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
ctccaaggat accagctgat                                              20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
aggcacaaga gatcagcttc                                              20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
agagccaagg gaagcatcat                                              20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
aagtcaatgt ttgccagtga                                              20
```

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
tgtcgcttac ttgggcataa                                              20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
gtaattttct tggcagggcg                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
cactgttcat gctgtaattt                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
tttttggcat ctgactcaca                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
atgtcctctt ggttaaagct                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
cgtggtgtag tctgggacag                                              20

<210> SEQ ID NO 133
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 133
cggtgtgaac cgtggtgtag                                                    20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
tcaggcaaag gcaaagcagt                                                    20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
taggaaaggc tactgcatga                                                    20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
taaaacatag ttttggttta                                                    20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
tcccaacaca gatttaaaac                                                    20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
caaaagccac ctgattgttt                                                    20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
tcctgaactg caaaagccac                                                    20
```

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
gcattcaatt tcctgaactg                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
taaatgtttt gcatatccaa                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
ttgtaaaaat ctaacttgtt                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tacctgagac cccagttcat                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
tacctgagac cccgcgcagc                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
tacctgagac ccacaagcgg                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 146
cctccagtac ctcggagttt                                              20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
gtccttgctc caggttagca                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
ttccactcac cccagttcat                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
gcagttctat cagaactttg                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
ctccagacgt gacccgactc                                              20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
ccacgcaccc acaagcggat                                              20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
taacctatgg tgactatgtc                                              20

<210> SEQ ID NO 153
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 153
tacctgagac ctgcaagaca                                               20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
atgctcacgt cagctattgg                                               20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
aaattcttac ttgtccccag                                               20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
ttggctttcc ctggaggttc                                               20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
cttcactaac cttgcagctt                                               20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
cacggcttac ctatttcgtc                                               20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
```

```
tcacacctac ctttgctgct                                               20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
catcttaatc cttggaaaca                                               20

<210> SEQ ID NO 161
<211> LENGTH: 20
<212> TYPE: DNA
<213> ORGANISM: H. sapiens
<220> FEATURE:

<400> SEQUENCE: 161
gaatggaaag aatgccctga                                               20

<210> SEQ ID NO 162
<211> LENGTH: 20
<212> TYPE: DNA
<213> ORGANISM: H. sapiens
<220> FEATURE:

<400> SEQUENCE: 162
gaaagaatgc cctgattatg                                               20

<210> SEQ ID NO 163
<211> LENGTH: 20
<212> TYPE: DNA
<213> ORGANISM: H. sapiens
<220> FEATURE:

<400> SEQUENCE: 163
ccagttccaa agattaaagg                                               20

<210> SEQ ID NO 164
<211> LENGTH: 20
<212> TYPE: DNA
<213> ORGANISM: H. sapiens
<220> FEATURE:

<400> SEQUENCE: 164
attgagctag atattgatga                                               20

<210> SEQ ID NO 165
<211> LENGTH: 20
<212> TYPE: DNA
<213> ORGANISM: H. sapiens
<220> FEATURE:

<400> SEQUENCE: 165
gacacagaca gacttctaag                                               20

<210> SEQ ID NO 166
<211> LENGTH: 20
<212> TYPE: DNA
<213> ORGANISM: H. sapiens
<220> FEATURE:

<400> SEQUENCE: 166
agcgacatta caccagcagg                                               20
```

```
<210> SEQ ID NO 167
<211> LENGTH: 20
<212> TYPE: DNA
<213> ORGANISM: H. sapiens
<220> FEATURE:

<400> SEQUENCE: 167
aaccaagagg acatttacat                                                    20

<210> SEQ ID NO 168
<211> LENGTH: 20
<212> TYPE: DNA
<213> ORGANISM: H. sapiens
<220> FEATURE:

<400> SEQUENCE: 168
agaggacatt tacatcacca                                                    20

<210> SEQ ID NO 169
<211> LENGTH: 20
<212> TYPE: DNA
<213> ORGANISM: H. sapiens
<220> FEATURE:

<400> SEQUENCE: 169
acatttacat caccacagaa                                                    20

<210> SEQ ID NO 170
<211> LENGTH: 20
<212> TYPE: DNA
<213> ORGANISM: H. sapiens
<220> FEATURE:

<400> SEQUENCE: 170
tacatcacca cagaaagcct                                                    20

<210> SEQ ID NO 171
<211> LENGTH: 20
<212> TYPE: DNA
<213> ORGANISM: H. sapiens
<220> FEATURE:

<400> SEQUENCE: 171
caccacagaa agccttacca                                                    20

<210> SEQ ID NO 172
<211> LENGTH: 20
<212> TYPE: DNA
<213> ORGANISM: H. sapiens
<220> FEATURE:

<400> SEQUENCE: 172
tatgtgagca cagaccaact                                                    20

<210> SEQ ID NO 173
<211> LENGTH: 20
<212> TYPE: DNA
<213> ORGANISM: H. sapiens
<220> FEATURE:

<400> SEQUENCE: 173
gagcacagac caactgaaca                                                    20
```

```
<210> SEQ ID NO 174
<211> LENGTH: 20
<212> TYPE: DNA
<213> ORGANISM: H. sapiens
<220> FEATURE:

<400> SEQUENCE: 174
ccaactgaac aaaatcatgc                                               20

<210> SEQ ID NO 175
<211> LENGTH: 20
<212> TYPE: DNA
<213> ORGANISM: H. sapiens
<220> FEATURE:

<400> SEQUENCE: 175
tctgctactt tgctgctatg                                               20

<210> SEQ ID NO 176
<211> LENGTH: 20
<212> TYPE: DNA
<213> ORGANISM: H. sapiens
<220> FEATURE:

<400> SEQUENCE: 176
tttctatagc caaaaatagc                                               20

<210> SEQ ID NO 177
<211> LENGTH: 20
<212> TYPE: DNA
<213> ORGANISM: H. sapiens
<220> FEATURE:

<400> SEQUENCE: 177
aatagctaaa tacctcaatc                                               20

<210> SEQ ID NO 178
<211> LENGTH: 20
<212> TYPE: DNA
<213> ORGANISM: H. sapiens
<220> FEATURE:

<400> SEQUENCE: 178
aggtcctaca ggtatggatc                                               20

<210> SEQ ID NO 179
<211> LENGTH: 20
<212> TYPE: DNA
<213> ORGANISM: H. sapiens
<220> FEATURE:

<400> SEQUENCE: 179
ctacaggtat ggatctctgg                                               20

<210> SEQ ID NO 180
<211> LENGTH: 20
<212> TYPE: DNA
<213> ORGANISM: H. sapiens
<220> FEATURE:

<400> SEQUENCE: 180
cacagcagct atccttagca                                               20

<210> SEQ ID NO 181
<211> LENGTH: 20
```

-continued

```
<212> TYPE: DNA
<213> ORGANISM: H. sapiens
<220> FEATURE:

<400> SEQUENCE: 181
taatccaggc ctaaagacaa                                               20

<210> SEQ ID NO 182
<211> LENGTH: 20
<212> TYPE: DNA
<213> ORGANISM: H. sapiens
<220> FEATURE:

<400> SEQUENCE: 182
tctaaggagc ctaaattcac                                               20

<210> SEQ ID NO 183
<211> LENGTH: 20
<212> TYPE: DNA
<213> ORGANISM: H. sapiens
<220> FEATURE:

<400> SEQUENCE: 183
gaacctagga cccatacagc                                               20

<210> SEQ ID NO 184
<211> LENGTH: 20
<212> TYPE: DNA
<213> ORGANISM: H. sapiens
<220> FEATURE:

<400> SEQUENCE: 184
gctggggaaa acagctgtta                                               20

<210> SEQ ID NO 185
<211> LENGTH: 20
<212> TYPE: DNA
<213> ORGANISM: H. sapiens
<220> FEATURE:

<400> SEQUENCE: 185
tggtggtaca gtggatgaaa                                               20

<210> SEQ ID NO 186
<211> LENGTH: 20
<212> TYPE: DNA
<213> ORGANISM: H. sapiens
<220> FEATURE:

<400> SEQUENCE: 186
ctgttgatga aatagtgcaa                                               20

<210> SEQ ID NO 187
<211> LENGTH: 20
<212> TYPE: DNA
<213> ORGANISM: H. sapiens
<220> FEATURE:

<400> SEQUENCE: 187
tagtgcaacc agatccaccc                                               20

<210> SEQ ID NO 188
<211> LENGTH: 20
<212> TYPE: DNA
<213> ORGANISM: H. sapiens
```

```
<220> FEATURE:

<400> SEQUENCE: 188
gatgggaagc accacgcaat                                               20

<210> SEQ ID NO 189
<211> LENGTH: 20
<212> TYPE: DNA
<213> ORGANISM: H. sapiens
<220> FEATURE:

<400> SEQUENCE: 189
atggaaaatg atggaccta                                                20

<210> SEQ ID NO 190
<211> LENGTH: 20
<212> TYPE: DNA
<213> ORGANISM: H. sapiens
<220> FEATURE:

<400> SEQUENCE: 190
cagttccagt gtactcattg                                               20

<210> SEQ ID NO 191
<211> LENGTH: 20
<212> TYPE: DNA
<213> ORGANISM: H. sapiens
<220> FEATURE:

<400> SEQUENCE: 191
tctggaaatt atggcgagtt                                               20

<210> SEQ ID NO 192
<211> LENGTH: 20
<212> TYPE: DNA
<213> ORGANISM: H. sapiens
<220> FEATURE:

<400> SEQUENCE: 192
atctttggaa tatttgggct                                               20

<210> SEQ ID NO 193
<211> LENGTH: 20
<212> TYPE: DNA
<213> ORGANISM: H. sapiens
<220> FEATURE:

<400> SEQUENCE: 193
gcaaaggatt aaaatgctga                                               20

<210> SEQ ID NO 194
<211> LENGTH: 20
<212> TYPE: DNA
<213> ORGANISM: H. sapiens
<220> FEATURE:

<400> SEQUENCE: 194
tctcctcaag gaaggaaaat                                               20

<210> SEQ ID NO 195
<211> LENGTH: 20
<212> TYPE: DNA
<213> ORGANISM: H. sapiens
<220> FEATURE:
```

```
<400> SEQUENCE: 195
agaggaggtg aacacaatct                                               20

<210> SEQ ID NO 196
<211> LENGTH: 20
<212> TYPE: DNA
<213> ORGANISM: H. sapiens
<220> FEATURE:

<400> SEQUENCE: 196
acagtgatga ctcttgggtt                                               20

<210> SEQ ID NO 197
<211> LENGTH: 20
<212> TYPE: DNA
<213> ORGANISM: H. sapiens
<220> FEATURE:

<400> SEQUENCE: 197
gctagatatt gatgagccag                                               20

<210> SEQ ID NO 198
<211> LENGTH: 20
<212> TYPE: DNA
<213> ORGANISM: H. sapiens
<220> FEATURE:

<400> SEQUENCE: 198
agactgagga atcagacaca                                               20

<210> SEQ ID NO 199
<211> LENGTH: 20
<212> TYPE: DNA
<213> ORGANISM: H. sapiens
<220> FEATURE:

<400> SEQUENCE: 199
atttcaatgc caatgacata                                               20

<210> SEQ ID NO 200
<211> LENGTH: 20
<212> TYPE: DNA
<213> ORGANISM: H. sapiens
<220> FEATURE:

<400> SEQUENCE: 200
aagcagatct cttatgcctt                                               20

<210> SEQ ID NO 201
<211> LENGTH: 20
<212> TYPE: DNA
<213> ORGANISM: H. sapiens
<220> FEATURE:

<400> SEQUENCE: 201
tcctactgaa ggagctgagt                                               20

<210> SEQ ID NO 202
<211> LENGTH: 20
<212> TYPE: DNA
<213> ORGANISM: H. sapiens
<220> FEATURE:

<400> SEQUENCE: 202
```

-continued

```
agaataaggc agggatgtcc                                          20

<210> SEQ ID NO 203
<211> LENGTH: 20
<212> TYPE: DNA
<213> ORGANISM: H. sapiens
<220> FEATURE:

<400> SEQUENCE: 203
acttccttat ggacaatgcc                                          20

<210> SEQ ID NO 204
<211> LENGTH: 20
<212> TYPE: DNA
<213> ORGANISM: H. sapiens
<220> FEATURE:

<400> SEQUENCE: 204
tgaggcagat gccaaaaagt                                          20

<210> SEQ ID NO 205
<211> LENGTH: 20
<212> TYPE: DNA
<213> ORGANISM: H. sapiens
<220> FEATURE:

<400> SEQUENCE: 205
cagatgccaa aaagtgcatc                                          20

<210> SEQ ID NO 206
<211> LENGTH: 20
<212> TYPE: DNA
<213> ORGANISM: H. sapiens
<220> FEATURE:

<400> SEQUENCE: 206
cctcatactc aatgcgactg                                          20

<210> SEQ ID NO 207
<211> LENGTH: 20
<212> TYPE: DNA
<213> ORGANISM: H. sapiens
<220> FEATURE:

<400> SEQUENCE: 207
tgcccttgcc tgacaaagag                                          20

<210> SEQ ID NO 208
<211> LENGTH: 20
<212> TYPE: DNA
<213> ORGANISM: H. sapiens
<220> FEATURE:

<400> SEQUENCE: 208
tcatgtggct atgtgagcac                                          20

<210> SEQ ID NO 209
<211> LENGTH: 20
<212> TYPE: DNA
<213> ORGANISM: H. sapiens
<220> FEATURE:

<400> SEQUENCE: 209
atcatgcctt agcctttctt                                          20
```

```
<210> SEQ ID NO 210
<211> LENGTH: 20
<212> TYPE: DNA
<213> ORGANISM: H. sapiens
<220> FEATURE:

<400> SEQUENCE: 210
ttcccaagag ctacgtattt                                            20

<210> SEQ ID NO 211
<211> LENGTH: 20
<212> TYPE: DNA
<213> ORGANISM: H. sapiens
<220> FEATURE:

<400> SEQUENCE: 211
ctgtttagta gcagtgattg                                            20

<210> SEQ ID NO 212
<211> LENGTH: 20
<212> TYPE: DNA
<213> ORGANISM: H. sapiens
<220> FEATURE:

<400> SEQUENCE: 212
ttgaatgcaa accatagcac                                            20

<210> SEQ ID NO 213
<211> LENGTH: 20
<212> TYPE: DNA
<213> ORGANISM: H. sapiens
<220> FEATURE:

<400> SEQUENCE: 213
atagtttgga tatgtaaaac                                            20

<210> SEQ ID NO 214
<211> LENGTH: 20
<212> TYPE: DNA
<213> ORGANISM: H. sapiens
<220> FEATURE:

<400> SEQUENCE: 214
tcaccaaatc ttggttgatg                                            20

<210> SEQ ID NO 215
<211> LENGTH: 20
<212> TYPE: DNA
<213> ORGANISM: H. sapiens
<220> FEATURE:

<400> SEQUENCE: 215
gagataagat ctatagcctc                                            20

<210> SEQ ID NO 216
<211> LENGTH: 20
<212> TYPE: DNA
<213> ORGANISM: H. sapiens
<220> FEATURE:

<400> SEQUENCE: 216
agaaactttc tttctcacta                                            20

<210> SEQ ID NO 217
```

```
-continued

<211> LENGTH: 20
<212> TYPE: DNA
<213> ORGANISM: H. sapiens
<220> FEATURE:

<400> SEQUENCE: 217
acatcattct tgagagcatt                                               20

<210> SEQ ID NO 218
<211> LENGTH: 20
<212> TYPE: DNA
<213> ORGANISM: H. sapiens
<220> FEATURE:

<400> SEQUENCE: 218
gaaaagctag aattgagtgt                                               20

<210> SEQ ID NO 219
<211> LENGTH: 20
<212> TYPE: DNA
<213> ORGANISM: H. sapiens
<220> FEATURE:

<400> SEQUENCE: 219
gctatggttt tctccaagag                                               20

<210> SEQ ID NO 220
<211> LENGTH: 20
<212> TYPE: DNA
<213> ORGANISM: H. sapiens
<220> FEATURE:

<400> SEQUENCE: 220
taaagtatca tcagtgtaga                                               20

<210> SEQ ID NO 221
<211> LENGTH: 20
<212> TYPE: DNA
<213> ORGANISM: H. sapiens
<220> FEATURE:

<400> SEQUENCE: 221
taattcaatt caaagctgtg                                               20

<210> SEQ ID NO 222
<211> LENGTH: 20
<212> TYPE: DNA
<213> ORGANISM: H. sapiens
<220> FEATURE:

<400> SEQUENCE: 222
agctgtgtgt ttggaagact                                               20

<210> SEQ ID NO 223
<211> LENGTH: 20
<212> TYPE: DNA
<213> ORGANISM: H. sapiens
<220> FEATURE:

<400> SEQUENCE: 223
ttactatttc acaacagcct                                               20

<210> SEQ ID NO 224
<211> LENGTH: 20
<212> TYPE: DNA
```

```
<213> ORGANISM: H. sapiens
<220> FEATURE:

<400> SEQUENCE: 224
cagcctgaca acatttctat                                               20

<210> SEQ ID NO 225
<211> LENGTH: 20
<212> TYPE: DNA
<213> ORGANISM: H. sapiens
<220> FEATURE:

<400> SEQUENCE: 225
gtctcagaat gtcattttgg                                               20

<210> SEQ ID NO 226
<211> LENGTH: 20
<212> TYPE: DNA
<213> ORGANISM: H. sapiens
<220> FEATURE:

<400> SEQUENCE: 226
gtggccacat aagccattat                                               20

<210> SEQ ID NO 227
<211> LENGTH: 20
<212> TYPE: DNA
<213> ORGANISM: H. sapiens
<220> FEATURE:

<400> SEQUENCE: 227
tcaatcaggg tcacataact                                               20

<210> SEQ ID NO 228
<211> LENGTH: 20
<212> TYPE: DNA
<213> ORGANISM: H. sapiens
<220> FEATURE:

<400> SEQUENCE: 228
tttgaacctc cagcctccat                                               20

<210> SEQ ID NO 229
<211> LENGTH: 20
<212> TYPE: DNA
<213> ORGANISM: H. sapiens
<220> FEATURE:

<400> SEQUENCE: 229
gtcttgaaag atggacccta                                               20

<210> SEQ ID NO 230
<211> LENGTH: 20
<212> TYPE: DNA
<213> ORGANISM: H. sapiens
<220> FEATURE:

<400> SEQUENCE: 230
gtttagattc tatctggaga                                               20

<210> SEQ ID NO 231
<211> LENGTH: 20
<212> TYPE: DNA
<213> ORGANISM: H. sapiens
<220> FEATURE:
```

<400> SEQUENCE: 231
aaagtaccag aatatttgga                                             20

<210> SEQ ID NO 232
<211> LENGTH: 20
<212> TYPE: DNA
<213> ORGANISM: M. musculus
<220> FEATURE:

<400> SEQUENCE: 232
tgccaagcag gcgcagccat                                             20

<210> SEQ ID NO 233
<211> LENGTH: 20
<212> TYPE: DNA
<213> ORGANISM: M. musculus
<220> FEATURE:

<400> SEQUENCE: 233
aaactccgag gtctcaggta                                             20

<210> SEQ ID NO 234
<211> LENGTH: 20
<212> TYPE: DNA
<213> ORGANISM: M. musculus
<220> FEATURE:

<400> SEQUENCE: 234
tctcaggtat ggatctttgt                                             20

<210> SEQ ID NO 235
<211> LENGTH: 20
<212> TYPE: DNA
<213> ORGANISM: M. musculus
<220> FEATURE:

<400> SEQUENCE: 235
ggaagtgagg ctacaccagc                                             20

<210> SEQ ID NO 236
<211> LENGTH: 20
<212> TYPE: DNA
<213> ORGANISM: M. musculus
<220> FEATURE:

<400> SEQUENCE: 236
caccagctac tcttggcaaa                                             20

<210> SEQ ID NO 237
<211> LENGTH: 20
<212> TYPE: DNA
<213> ORGANISM: M. musculus
<220> FEATURE:

<400> SEQUENCE: 237
ctcgattcac caagtgtcgt                                             20

<210> SEQ ID NO 238
<211> LENGTH: 20
<212> TYPE: DNA
<213> ORGANISM: M. musculus
<220> FEATURE:

<400> SEQUENCE: 238

-continued tatgctaaaa gggaaagcca                              20

<210> SEQ ID NO 239
<211> LENGTH: 20
<212> TYPE: DNA
<213> ORGANISM: M. musculus
<220> FEATURE:

<400> SEQUENCE: 239
aaacagctgt tacttcaact                              20

<210> SEQ ID NO 240
<211> LENGTH: 20
<212> TYPE: DNA
<213> ORGANISM: M. musculus
<220> FEATURE:

<400> SEQUENCE: 240
cccattggcc tcaactggac                              20

<210> SEQ ID NO 241
<211> LENGTH: 20
<212> TYPE: DNA
<213> ORGANISM: M. musculus
<220> FEATURE:

<400> SEQUENCE: 241
tctgaaggga tggataattc                              20

<210> SEQ ID NO 242
<211> LENGTH: 20
<212> TYPE: DNA
<213> ORGANISM: M. musculus
<220> FEATURE:

<400> SEQUENCE: 242
tggagtatga aattcagtac                              20

<210> SEQ ID NO 243
<211> LENGTH: 20
<212> TYPE: DNA
<213> ORGANISM: M. musculus
<220> FEATURE:

<400> SEQUENCE: 243
gaaaagtaca gcgagttcag                              20

<210> SEQ ID NO 244
<211> LENGTH: 20
<212> TYPE: DNA
<213> ORGANISM: M. musculus
<220> FEATURE:

<400> SEQUENCE: 244
ttggaatatt tggagtagca                              20

<210> SEQ ID NO 245
<211> LENGTH: 20
<212> TYPE: DNA
<213> ORGANISM: M. musculus
<220> FEATURE:

<400> SEQUENCE: 245
gattgatcca gatcttctca                              20

<210> SEQ ID NO 246
<211> LENGTH: 20
<212> TYPE: DNA
<213> ORGANISM: M. musculus
<220> FEATURE:

<400> SEQUENCE: 246
ggcattcatg ataactacaa                                                  20

<210> SEQ ID NO 247
<211> LENGTH: 20
<212> TYPE: DNA
<213> ORGANISM: M. musculus
<220> FEATURE:

<400> SEQUENCE: 247
atcagctggt atccttggag                                                  20

<210> SEQ ID NO 248
<211> LENGTH: 20
<212> TYPE: DNA
<213> ORGANISM: M. musculus
<220> FEATURE:

<400> SEQUENCE: 248
gaagctgatc tcttgtgcct                                                  20

<210> SEQ ID NO 249
<211> LENGTH: 20
<212> TYPE: DNA
<213> ORGANISM: M. musculus
<220> FEATURE:

<400> SEQUENCE: 249
tcactggcaa acattgactt                                                  20

<210> SEQ ID NO 250
<211> LENGTH: 20
<212> TYPE: DNA
<213> ORGANISM: M. musculus
<220> FEATURE:

<400> SEQUENCE: 250
ttatgcccaa gtaagcgaca                                                  20

<210> SEQ ID NO 251
<211> LENGTH: 20
<212> TYPE: DNA
<213> ORGANISM: M. musculus
<220> FEATURE:

<400> SEQUENCE: 251
aaattacagc atgaacagtg                                                  20

<210> SEQ ID NO 252
<211> LENGTH: 20
<212> TYPE: DNA
<213> ORGANISM: M. musculus
<220> FEATURE:

<400> SEQUENCE: 252
tgtgagtcag atgccaaaaa                                                  20

```
<210> SEQ ID NO 253
<211> LENGTH: 20
<212> TYPE: DNA
<213> ORGANISM: M. musculus
<220> FEATURE:

<400> SEQUENCE: 253
agctttaacc aagaggacat                                           20

<210> SEQ ID NO 254
<211> LENGTH: 20
<212> TYPE: DNA
<213> ORGANISM: M. musculus
<220> FEATURE:

<400> SEQUENCE: 254
tcatgcagta gcctttccta                                           20

<210> SEQ ID NO 255
<211> LENGTH: 20
<212> TYPE: DNA
<213> ORGANISM: M. musculus
<220> FEATURE:

<400> SEQUENCE: 255
gttttaaatc tgtgttggga                                           20

<210> SEQ ID NO 256
<211> LENGTH: 20
<212> TYPE: DNA
<213> ORGANISM: M. musculus
<220> FEATURE:

<400> SEQUENCE: 256
aaacaatcag gtggcttttg                                           20

<210> SEQ ID NO 257
<211> LENGTH: 20
<212> TYPE: DNA
<213> ORGANISM: M. musculus
<220> FEATURE:

<400> SEQUENCE: 257
cagttcagga aattgaatgc                                           20

<210> SEQ ID NO 258
<211> LENGTH: 20
<212> TYPE: DNA
<213> ORGANISM: M. musculus
<220> FEATURE:

<400> SEQUENCE: 258
ttggatatgc aaaacattta                                           20

<210> SEQ ID NO 259
<211> LENGTH: 20
<212> TYPE: DNA
<213> ORGANISM: M. musculus
<220> FEATURE:

<400> SEQUENCE: 259
aaactccgag gtactggagg                                           20

<210> SEQ ID NO 260
<211> LENGTH: 20
```

```
<212> TYPE: DNA
<213> ORGANISM: M. musculus
<220> FEATURE:

<400> SEQUENCE: 260
tgctaacctg gagcaaggac                                          20

<210> SEQ ID NO 261
<211> LENGTH: 20
<212> TYPE: DNA
<213> ORGANISM: M. musculus
<220> FEATURE:

<400> SEQUENCE: 261
atgaactggg gtgagtggaa                                          20

<210> SEQ ID NO 262
<211> LENGTH: 20
<212> TYPE: DNA
<213> ORGANISM: M. musculus
<220> FEATURE:

<400> SEQUENCE: 262
caaagttctg atagaactgc                                          20

<210> SEQ ID NO 263
<211> LENGTH: 20
<212> TYPE: DNA
<213> ORGANISM: M. musculus
<220> FEATURE:

<400> SEQUENCE: 263
gagtcgggtc acgtctggag                                          20

<210> SEQ ID NO 264
<211> LENGTH: 20
<212> TYPE: DNA
<213> ORGANISM: M. musculus
<220> FEATURE:

<400> SEQUENCE: 264
atccgcttgt gggtgcgtgg                                          20

<210> SEQ ID NO 265
<211> LENGTH: 20
<212> TYPE: DNA
<213> ORGANISM: M. musculus
<220> FEATURE:

<400> SEQUENCE: 265
gaacctccag ggaaagccaa                                          20

<210> SEQ ID NO 266
<211> LENGTH: 20
<212> TYPE: DNA
<213> ORGANISM: M. musculus
<220> FEATURE:

<400> SEQUENCE: 266
aagctgcaag gttagtgaag                                          20

<210> SEQ ID NO 267
<211> LENGTH: 20
<212> TYPE: DNA
<213> ORGANISM: M. musculus
```

```
<220> FEATURE:

<400> SEQUENCE: 267
agagagctac ctaactaaca                                               20

<210> SEQ ID NO 268
<211> LENGTH: 20
<212> TYPE: DNA
<213> ORGANISM: Artificial sequence
<220> FEATURE:
<223> OTHER INFORMATION: Scrambled control oligonucleotide

<400> SEQUENCE: 268
ttaccgtatg gttcctcact                                               20
```